(12) United States Patent
Reddy et al.

(10) Patent No.: US 10,188,654 B2
(45) Date of Patent: Jan. 29, 2019

(54) USES OF PYRIMIDO-PYRIDAZINONES TO TREAT CANCER

(71) Applicant: Asana Biosciences, LLC, Lawrenceville, NJ (US)

(72) Inventors: Sanjeeva P. Reddy, Chester Springs, PA (US); Sandeep Gupta, Plainsboro, NJ (US); Roger Astbury Smith, Chester Springs, PA (US)

(73) Assignee: Asana BioSciences, LLC, Lawrenceville, NJ (US)

( * ) Notice: Subject to any disclaimer, the term of this patent is extended or adjusted under 35 U.S.C. 154(b) by 0 days.

(21) Appl. No.: 15/365,222

(22) Filed: Nov. 30, 2016

(65) Prior Publication Data

US 2017/0157126 A1   Jun. 8, 2017

Related U.S. Application Data

(60) Provisional application No. 62/263,398, filed on Dec. 4, 2015.

(51) Int. Cl.
| | |
|---|---|
| *A61K 31/519* | (2006.01) |
| *A61K 31/551* | (2006.01) |
| *A61K 31/55* | (2006.01) |
| *A61K 31/5377* | (2006.01) |
| *A61K 9/00* | (2006.01) |
| *A61K 31/541* | (2006.01) |
| *A61K 31/675* | (2006.01) |

(52) U.S. Cl.
CPC .......... *A61K 31/519* (2013.01); *A61K 9/0019* (2013.01); *A61K 9/0053* (2013.01); *A61K 31/5377* (2013.01); *A61K 31/541* (2013.01); *A61K 31/55* (2013.01); *A61K 31/551* (2013.01); *A61K 31/675* (2013.01)

(58) Field of Classification Search
CPC combination set(s) only.
See application file for complete search history.

(56) References Cited

U.S. PATENT DOCUMENTS

| | | | | |
|---|---|---|---|---|
| 8,729,079 | B2 * | 5/2014 | Venkatesan | C07D 487/04 514/210.02 |
| 9,382,277 | B2 * | 7/2016 | Venkatesan | C07D 487/04 |
| 2013/0023523 | A1 | 1/2013 | Zhu et al. | |
| 2013/0053346 | A1 | 2/2013 | Venkatesan et al. | |

FOREIGN PATENT DOCUMENTS

| | | |
|---|---|---|
| WO | 2009145856 A1 | 12/2009 |
| WO | 2010019637 A1 | 2/2010 |
| WO | 2011053861 A1 | 5/2011 |

OTHER PUBLICATIONS

Hao et al. Clinical Cancer Research (2014), 20(10), p. 2674-2683.*
Sanjeeva Reddy et al. Cancer Research, (2015), vol. 75, No. Suppl. 15, p. 792, Aug. 2015, accessible to public at 106th Annual Meeting of the American-Association-For-Cancer-Research (AACR); Philadelphia, PA, USA; Apr. 18-22, 2015.*
Zhang et al., Br. J. Haematol. 170(4):445-56 (2015).
Sinha, JNCI News, vol. 106, Issue 11, Nov. 12, 2014, downloaded from JNCI.Oxfordjournals.org.
Rao et al., Blood 2015, 126:4009.
Reddy, Sanjeeva et al., ASN002: A novel dual SYK/JAK inhibitor with strong antitumor activity, Proceedings of the 106th Annual Meeting of the American Association for Cancer Research, Apr. 18-22, 2015, Abstract nr 792.
International Search Report and the Written Opinion of the International Searching Authority, or the Declaration, International application No. PCT/US2016/064178, dated Mar. 31, 2017.
Examination Report from corresponding Taiwanese Application No. 105138865; dated Nov. 6, 2017, along with its English translation.
International Preliminary Report on Patentability from corresponding International Application No. PCT/US2016/064178, dated Jun. 14, 2018.

* cited by examiner

*Primary Examiner* — Yong L Chu
(74) *Attorney, Agent, or Firm* — DLA Piper LLP (US)

(57) ABSTRACT

Disclosed are methods of treating cancer, which include administering a therapeutically effective amount of a compound of Formula (I), or a pharmaceutically acceptable salt or ester thereof, to a subject in need thereof.

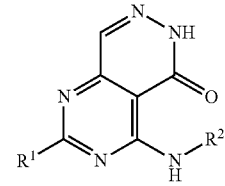

Also disclosed are methods of inhibiting growth and proliferation of cancer cells in vitro or in vivo, which include contacting the cells with an amount of the compound of formula (I) effective to inhibit the growth or proliferation of the cancer cells. Further disclosed are methods of inhibiting tumor growth, which include contacting the tumor with an amount of the compound of formula (I) effective to inhibit the growth of the tumor.

17 Claims, 6 Drawing Sheets

USES OF PYRIMIDO-PYRIDAZINONES TO TREAT CANCER

CROSS REFERENCE TO RELATED APPLICATIONS

The present application claims the benefit of the filing date of U.S. Provisional Application No. 62/263,398, filed Dec. 4, 2015, the disclosure of which is incorporated herein by reference.

BACKGROUND OF THE INVENTION

The challenges of identifying clinically useful anti-cancer drugs and obtaining FDA approval for marketing can often be exacerbated by incidences of resistance of the drug in cancer patients. For example, ibrutinib is an orally bioavailable and highly specific inhibitor of Bruton tyrosine kinase (BTK) that was recently approved for treatment of patients with recurrent chronic lymphocytic leukemia (CLL) and mantle cell lymphoma (MCL). Ibrutinib has also shown efficacy in subsets of patients with diffuse large B cell lymphoma (DLBCL) and Waldenstrom macroglobulinaemia (WM). However, despite activity in multiple B-cell malignancies, cases of primary and secondary resistance have emerged along with predictions that the incidence of observed resistance will increase as clinical use expands over time. Zhang et al., Br. J. Haematol. 170(4):445-56 (2015). Although the suspected mechanism of resistance has been elucidated (a C481→S mutation in the BTK gene), further studies have shown that at least two other cellular mechanisms appear to override the inhibitory action of ibrutinib in resistant cancer cells, leading to proposals of using ibrutinib in combination with palbociclib or palbociclib followed by idelalisib. See, Sinha, "Overcoming Mantle Cell Lymphoma's Ibrutinib Resistance," in JNCI, 106(11), 2014.

In view of the foregoing, a need remains for anti-cancer drugs that are efficacious and which could treat cancer patients, such as patients whose cancer has proven resistant or refractory to FDA-approved front-line therapy.

BRIEF SUMMARY OF THE INVENTION

In one aspect, the present invention provides a method of treating cancer, which includes administering a therapeutically effective amount of a compound of Formula (I), or a pharmaceutically acceptable salt or ester thereof, wherein $R^1$ and $R^2$ are defined herein, to a subject in need thereof.

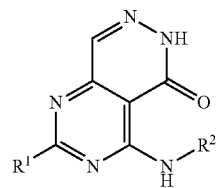

Another aspect of the present invention is directed to a method of inhibiting growth and proliferation of cancer cells in vitro or in vivo, which includes contacting the cells with an amount of the compound of formula (I) effective to inhibit the growth or proliferation of the cancer cells.

A further aspect of the present invention is directed to a method of inhibiting tumor growth, which includes contacting the tumor with an amount of the compound of formula (I) effective to inhibit the growth of the tumor.

In some embodiments of the inventive methods, cancers, cancer cells and tumors treatable in accordance with the methods of the present invention include non-solid tumors, e.g., hematopoietic cancers such as leukemias, multiple myelomas and lymphomas, and solid tumors. In certain embodiments, the hematopoietic cancer is a B-cell lymphoma, e.g., diffuse large B-cell lymphoma, mantle cell lymphoma, or follicular lymphoma. In some embodiments, the leukemia is acute myeloid leukemia (AML), e.g., human erythroleukemia. In some embodiments, the subject with hematopoietic cancer is or has become refractory to treatment with Ibrutinib. In certain embodiments, the solid tumor is a tumor of the bladder, colon, liver, kidney, lung, breast, ovary or cervix. In some embodiments, the compound of formula (I) is 2-(1-(4-((4-(4-hydroxypiperidin-1-yl)phenyl)amino)-5-oxo-5,6-dihydropyrimido[4,5-d]pyridazin-2-yl)piperidin-4-yl)acetonitrile (also described herein as ASN002 or compound 189) or a pharmaceutically acceptable salt or ester thereof.

Other aspects and advantages of the invention will be readily apparent from the following detailed description of the invention.

DETAILED DESCRIPTION

Figure 1:
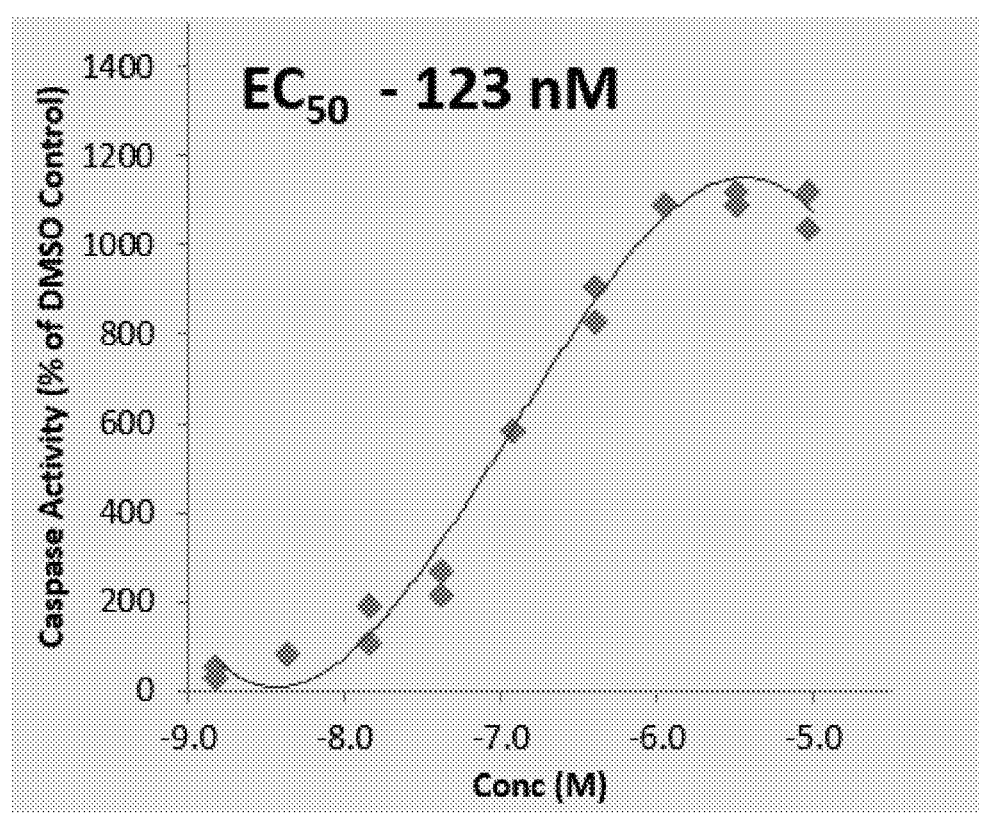
FIG. 1 is a graph that shows that ASN002 induced apoptosis in a DLBCL cell line, Pfeiffer, using a caspase 3/7 assay. The data show that after a 24-hour treatment, the $EC_{50}$ of ASN002 was 120 nM.
Figure 2:
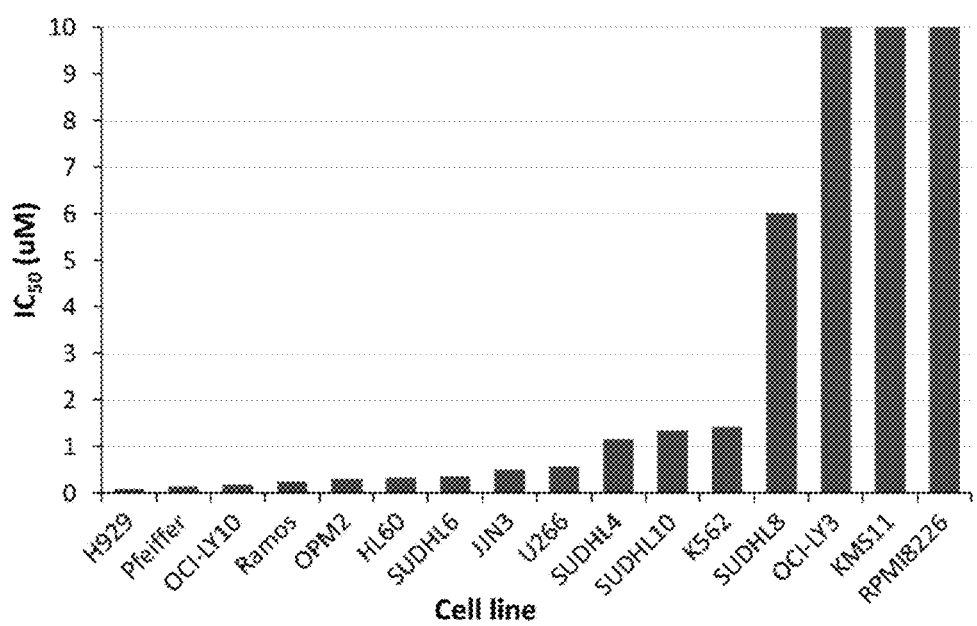
FIG. 2 is a bar graph showing that ASN002 exhibited strong antiproliferative activity in several hematological malignant cell lines, wherein the data were generated in a cell line panel representing leukemia, lymphoma, and multiple myelomas.
Figure 3:
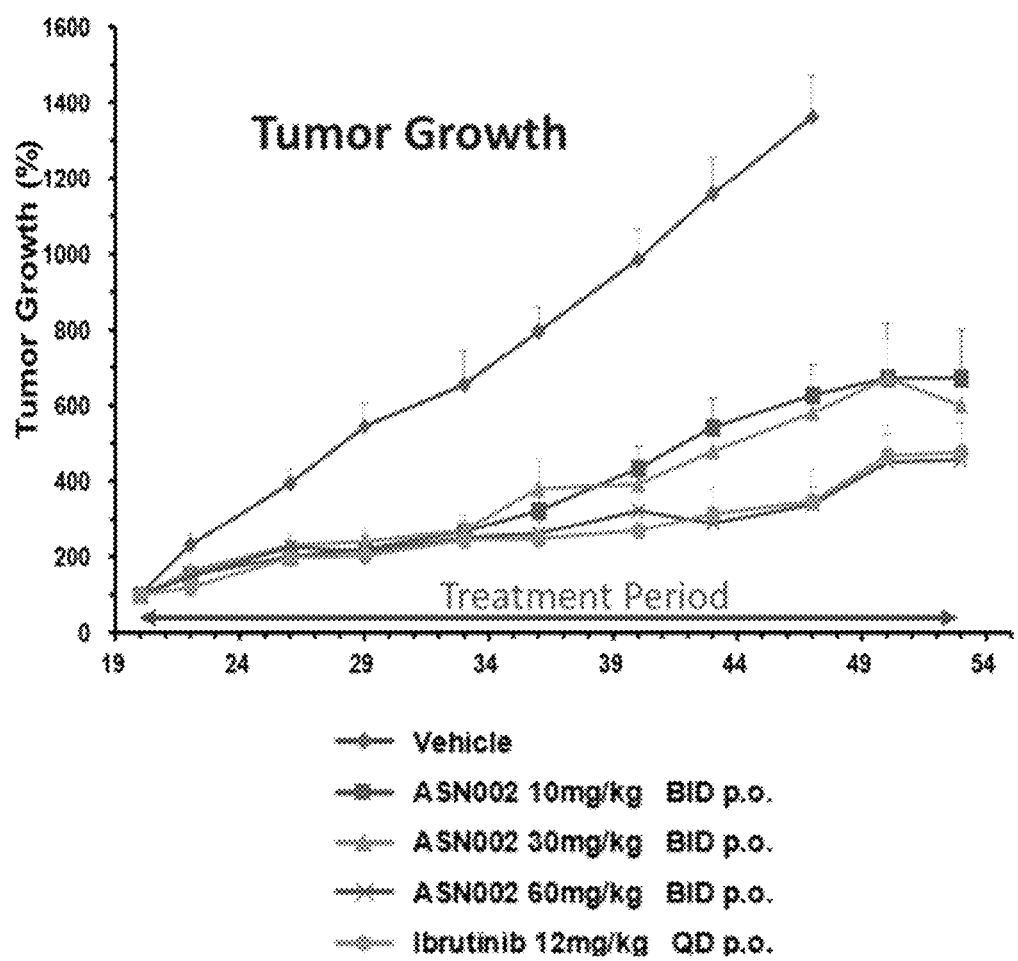
FIG. 3 is a graph showing that ASN002 inhibited tumor growth in a DLBCL xenograft mouse model (derived from Pfeiffer cell line).
Figure 4:
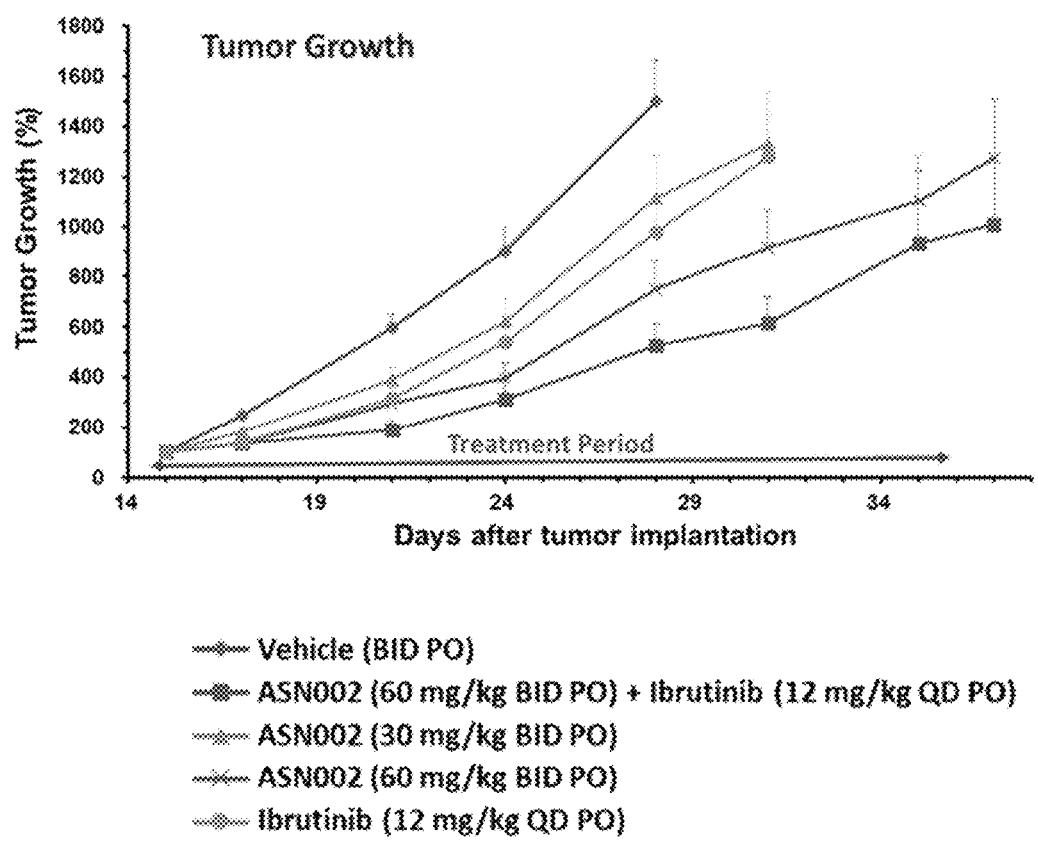
FIG. 4 is a graph showing that compound ASN002 inhibited tumor growth in another DLBCL xenograft mouse model (derived from SU-DHL-6 cell line).
Figure 5:
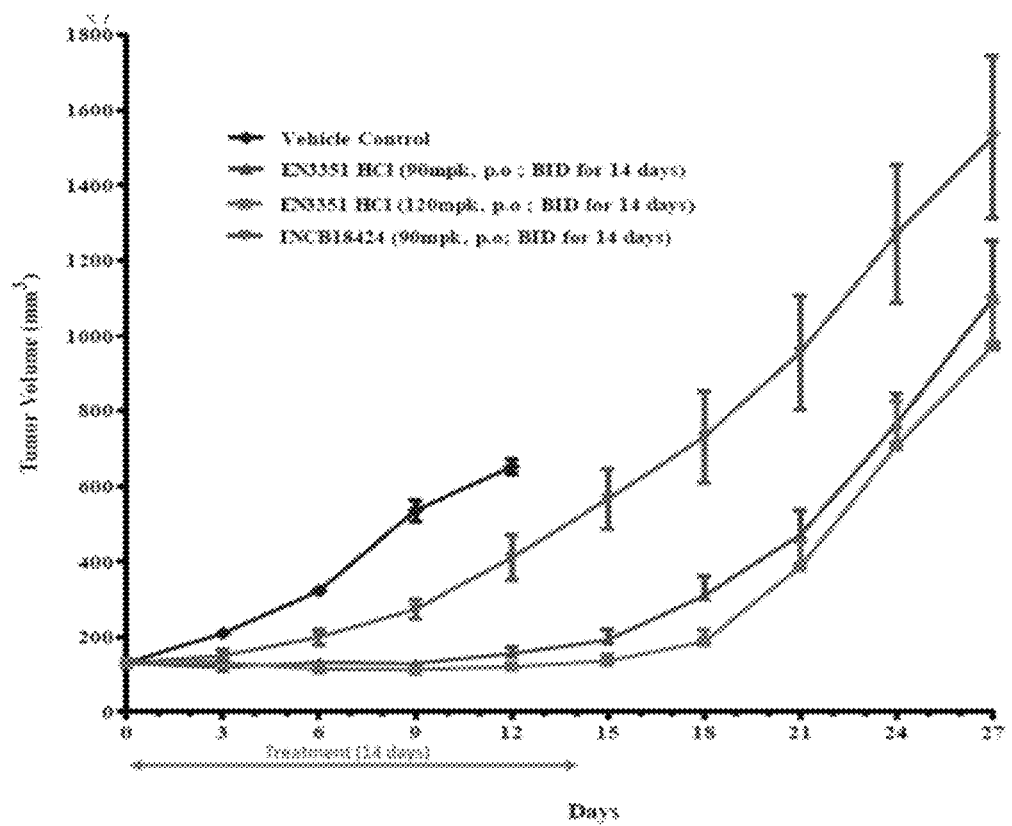
FIG. 5 is a graph showing that ASN002 inhibited tumor growth in a mouse model of multiple myeloma (derived from H929 cell line).
Figure 6:
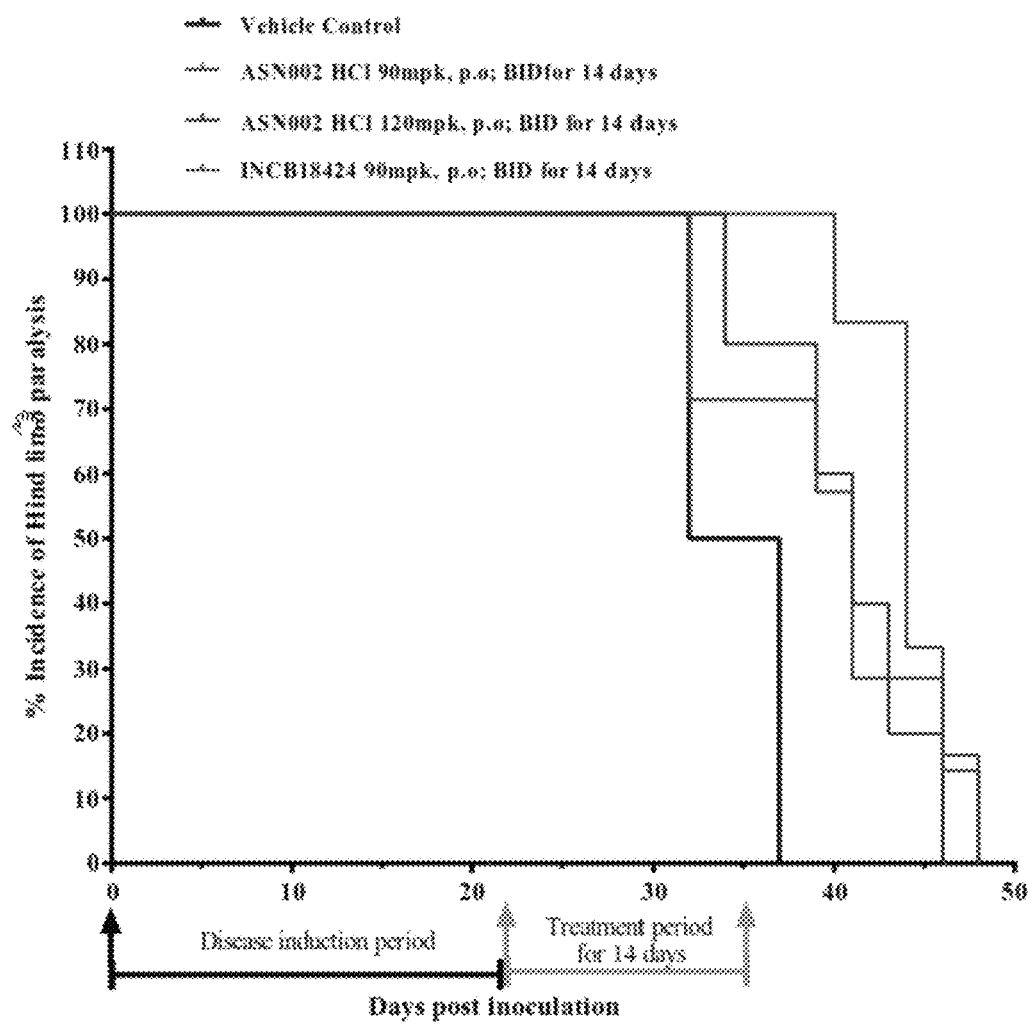
FIG. 6 is a graph showing that ASN002 delayed the hind limb paralysis in a mouse model of human erythroleukemia (derived from HEL cell line).

Compounds useful in the practice of the inventive methods may be represented by Formula (I):

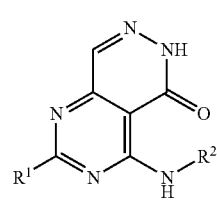

In this formula, $R^1$ is $NR^4R^5$, optionally substituted $C_1$ to $C_6$ alkoxy, optionally substituted $C_6$ to $C_{14}$ aryl, optionally substituted heteroaryl, optionally substituted 3-10 membered monocyclic or bicyclic cycloalkyl, or optionally substituted 3-10 membered monocyclic or bicyclic heterocyclyl. In one aspect, the 3-4 membered cycloalkyl and heterocyclyl are saturated. In another aspect, the hydrogen atoms on the same carbon atom of the cycloalkyl or heterocyclyl are optionally replaced with an optionally substituted 3-6 membered cycloalkyl or heterocyclyl to form a spirocycloalkyl or spiroheterocyclyl. In a further aspect, the hydrogen atoms on the same atom of the cycloalkyl or heterocyclyl are optionally replaced with O to form an oxo substituent.

i. In another embodiment, $R^1$ is $N(C_1$ to $C_6$ alkyl)($C_1$ to $C_6$ alkyl) or $C_1$ to $C_6$ alkoxy.

ii. In still a further embodiment, $R^1$ is $N(CH(CH_3)_2)_2$, $N(CH_3)_2$, $OCH_2CH_3$, or $OCH_3$.

iii. In another embodiment, $R^1$ is optionally substituted phenyl.

iv. In still another embodiment, $R^1$ is of the structure:

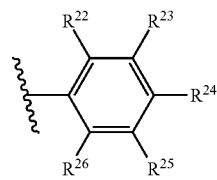

wherein, $R^{22}$, $R^{23}$, $R^{24}$, $R^{25}$, and $R^{26}$ are, independently, H, $C(O)(C_1$ to $C_6$ alkoxy), $C(O)OH$, $O(C_1$ to $C_3$ perfluoroalkyl), $O(C_1$ to $C_6$ perfluoroalkoxy), $C_1$ to $C_6$ alkoxy, halogen, ($C_1$ to $C_6$ alkyl)heterocyclyl, or ($C_1$ to $C_6$ alkyl)CN.

v. In a further embodiment, $R^1$ is:

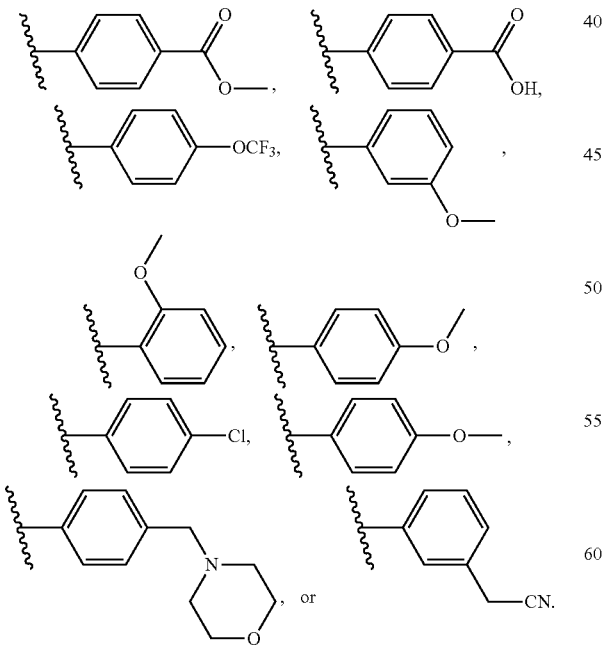

vi. In yet another embodiment, $R^1$ is optionally substituted 5-9 membered saturated heterocyclyl.

vii. In still a further embodiment, $R^1$ is of the structure:

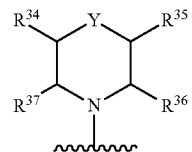

wherein, $R^{34}$, $R^{35}$, $R^{36}$, and $R^{37}$ are, independently, H, $C_1$ to $C_6$ alkyl, or CN; Y is $(C(R^8)_2)_x$, $NR^7(C(R^8)_2)_x$, O, (S=O), $SO_2$, or $NR^7$; $R^7$ and $R^8$ are, independently, H, $C_1$ to $C_6$ alkyl, $C(O)OH$, ($C_1$ to $C_6$ alkyl) CN, ($C_1$ to $C_6$ alkyl)$C(O)OH$, $C(O)(C_1$ to $C_6$ alkyl) CN, or CN; and x is 0 to 2.

viii. In another embodiment, $R^1$ is:

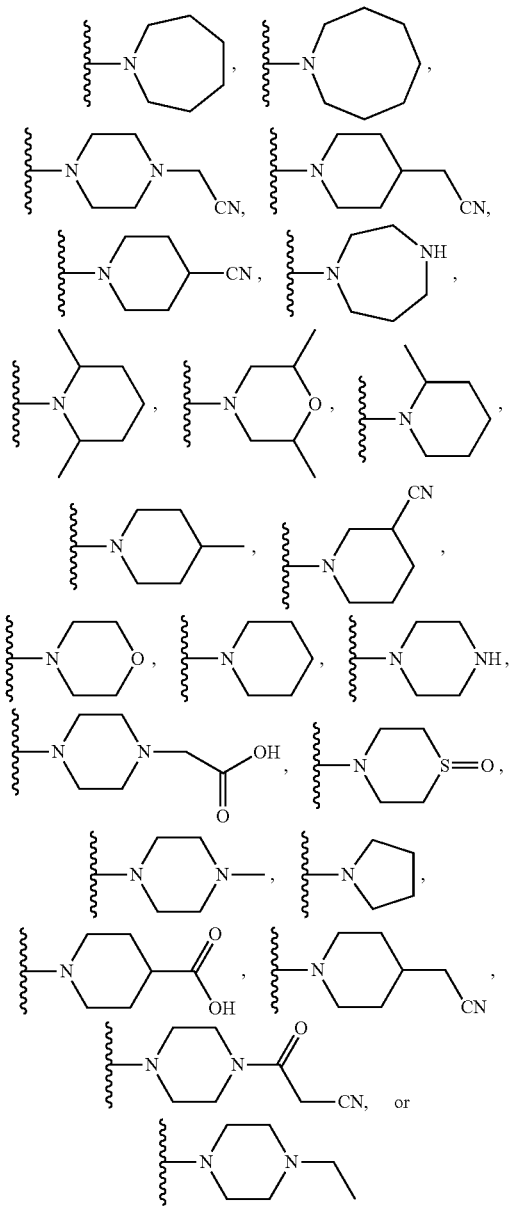

ix. In still a further embodiment, $R^1$ is of the structure:

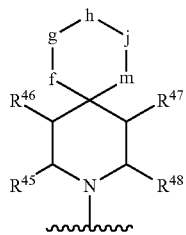

wherein, f, g, h, j, and m are, independently, absent, (CH$_2$), CH($R^3$), Z, or C=O; $R^3$ is H, C(O)OH, or C(O)O(C$_1$ to C$_6$ alkyl); $R^{45}$, $R^{46}$, $R^{47}$, and $R^{48}$ are, independently, H or C$_1$ to C$_6$ alkyl; and Z is O, S, SO, SO$_2$, or NH.

x. In yet another embodiment, $R^1$ is:

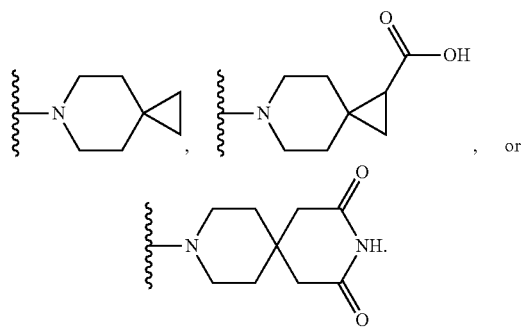

xi. In a further embodiment, $R^1$ is a heteroaryl.
xii. In yet another embodiment, $R^1$ is thiophene, benzo-oxole, or pyridine.
xiii. In still another embodiment, $R^1$ is a monocyclic C$_3$ to C$_8$ cycloalkyl.
xiv. In yet a further embodiment, $R^1$ is cycloheptyl or cyclohexyl, both optionally substituted with —N(C$_1$ to C$_6$ alkyl)(C$_1$ to C$_6$ alkyl).
xv. In another embodiment, $R^1$ is piperidine substituted with C(O)(C$_1$ to C$_6$ alkyl)CN.
xvi. In still a further embodiment, $R^1$ is:

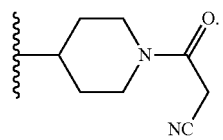 [SMILES: *C1CCN(C(=O)CC#N)CC1]

a. In one embodiment, $R^2$ is phenyl substituted with C(O)NR$^4$R$^5$.
b. In another embodiment, $R^2$ is phenyl substituted with

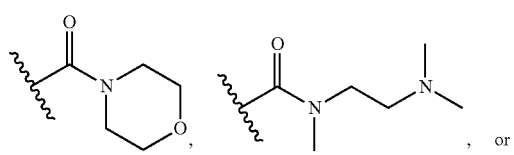

-continued

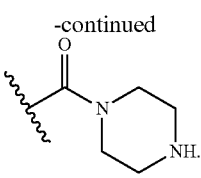

c. In a further embodiment, $R^2$ is phenyl substituted with NR$^4$R$^5$.
d. In yet another embodiment, $R^2$ is phenyl substituted with (C$_1$ to C$_6$ alkyl)NR$^4$R$^5$.
e. In another embodiment, $R^2$ is phenyl substituted with NR$^4$R$^5$ or (C$_1$ to C$_6$ alkyl)NR$^4$R$^5$ and R$^4$ and R$^5$ are taken together with the nitrogen atom to which they are attached to form a 6-membered ring.
f. In still a further embodiment, $R^2$ is phenyl substituted with NR$^4$R$^5$ or (C$_1$ to C$_6$ alkyl)NR$^4$R$^5$ and R$^4$ and R$^5$ are joined to form a heterocyclyl of the structure:

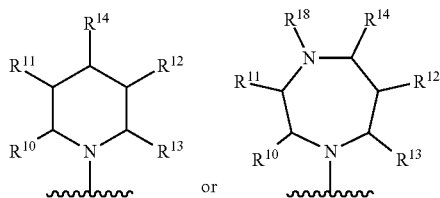

wherein, $R^{10}$, $R^{11}$, $R^{12}$, and $R^{13}$ are, independently, H or C$_1$ to C$_6$ alkyl; $R^{14}$ is halogen, OH, C(O)OH, C$_1$ to C$_6$ alkoxy, (C$_1$ to C$_6$ alkyl)halogen, (C$_1$ to C$_6$ alkyl)C(O)OH, C$_1$ to C$_6$ hydroxyalkyl, C$_3$ to C$_8$ cycloalkyl, (C$_1$ to C$_6$ alkyl)C(O)NH$_2$, (C$_1$ to C$_6$ alkyl)C(O)NH(C$_1$ to C$_6$ hydroxyalkyl), (C$_1$ to C$_6$ alkyl)C(O)N(C$_1$ to C$_6$ hydroxyalkyl)$_2$, (C$_1$ to C$_6$ alkyl)CN, (C$_1$ to C$_6$ alkyl)heteroaryl, or heteroaryl; and $R^{18}$ is C$_1$ to C$_6$ hydroxyalkyl or (C$_1$ to C$_6$ alkyl)C(O)OH.

g. In yet a further embodiment, $R^2$ is phenyl substituted with NR$^4$R$^5$ or (C$_1$ to C$_6$ alkyl)NR$^4$R$^5$ and wherein R$^4$ and R$^5$ are joined to form an optionally substituted piperidine or diazepane.
h. In another embodiment, $R^2$ is phenyl substituted with NR$^4$R$^5$ or (C$_1$ to C$_6$ alkyl)NR$^4$R$^5$ and R$^4$ and R$^5$ are joined to form:

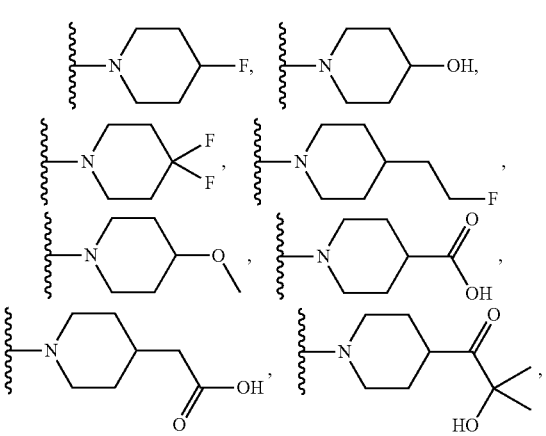

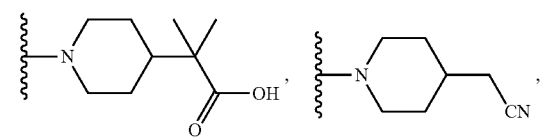
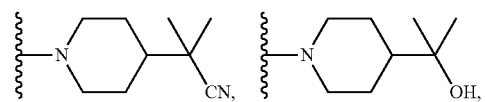
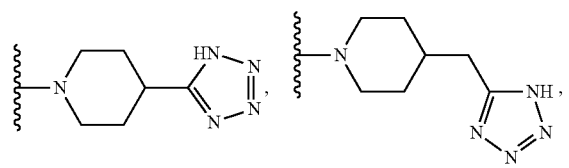
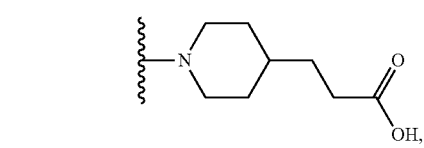
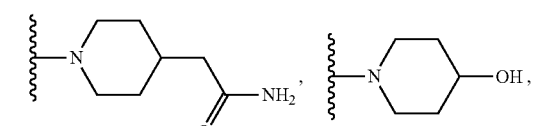
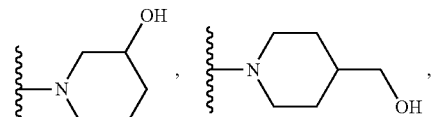
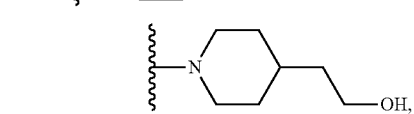
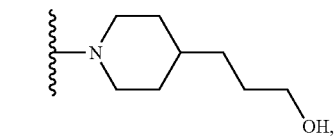
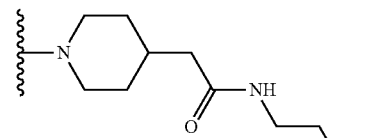
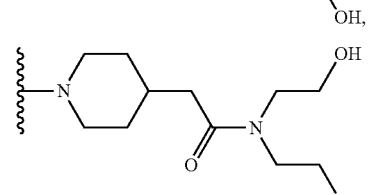
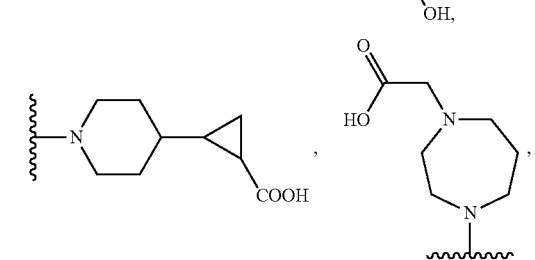

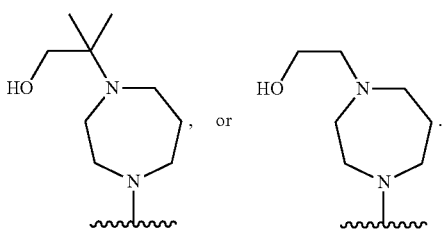

i. In still a further embodiment, $R^2$ is phenyl substituted with $NR^4R^5$ or ($C_1$ to $C_6$ alkyl)$NR^4R^5$ and $R^4$ and $R^5$ are joined to form a heterocyclyl of the structure:

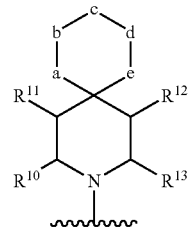

wherein, a, b, c, d, and e are, independently, absent, (CH$_2$), CH($R^3$), Z, or C=O; $R^3$ is H, C(O)OH, $C_1$ to $C_6$ hydroxyalkyl, or C(O)O($C_1$ to $C_6$ alkyl); $R^{10}$, $R^{11}$, $R^{12}$, and $R^{13}$ are, independently, H or $C_1$ to $C_6$ alkyl; and Z is O, S, or NH.

j. In yet another embodiment, $R^2$ is phenyl substituted with $NR^4R^5$ or ($C_1$ to $C_6$ alkyl)$NR^4R^5$ and $R^4$ and $R^5$ are joined to form:

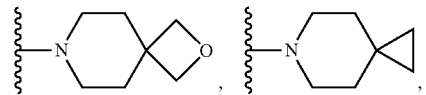
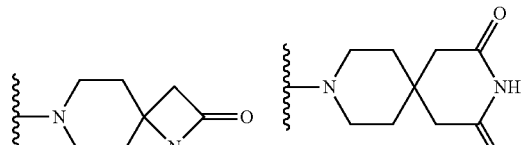
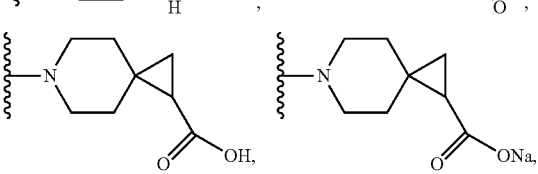
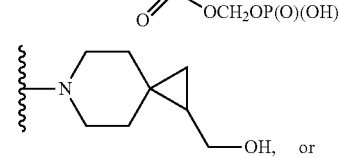

-continued

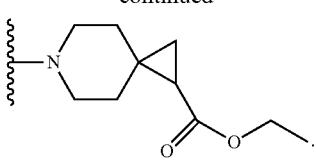

k. In a further embodiment, $R^2$ is phenyl substituted with $NR^4R^5$ or $(C_1$ to $C_6$ alkyl$)NR^4R^5$ and $R^4$ and $R^5$ are taken together to form a heterocyclyl of the structure:

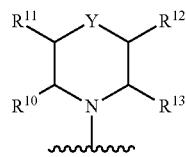

wherein, $R^{10}$, $R^{11}$, $R^{12}$, and $R^{13}$ are, independently, H or $C_1$ to $C_6$ alkyl; Y is O or $NR^9$; and $R^9$ is H, $C_1$ to $C_6$ alkyl, OH, C(O)OH, $C_1$ to $C_6$ hydroxyalkyl, $(C_1$ to $C_6$ alkyl$)NH_2$, $(C_1$ to $C_6$ alkyl$)N(C_1$ to $C_6$ alkyl$)(C_1$ to $C_6$ alkyl$)$, $(C_1$ to $C_6$ alkyl$)(C_1$ to $C_6$ alkoxy$)$, $C(O)(C_1$ to $C_6$ alkyl$)NH_2$, $(C_1$ to $C_6$ alkyl$)C(O)OH$, $C(O)(C_1$ to $C_6$ hydroxyalkyl$)$, $C(O)(C_1$ to $C_6$ alkyl$)CN$, $(C_1$ to $C_6$ alkyl$)CN$, $(C_1$ to $C_6$ alkyl$)$halogen, or $(C_1$ to $C_6$ alkyl$)O(C_1$ to $C_6$ alkyl$)C(O)(C_1$ to $C_6$ alkyl$)NH_2$; wherein 2 hydrogen atoms attached to the same carbon atom are optionally replaced with =O.

l. In yet another embodiment, $R^2$ is phenyl substituted with $NR^4R^5$ or $(C_1$ to $C_6$ alkyl$)NR^4R^5$ and $R^4$ and $R^5$ are taken together to form an optionally substituted morpholine or piperazine.

m. In still a further embodiment, $R^2$ is phenyl substituted with $NR^4R^5$ or $(C_1$ to $C_6$ alkyl$)NR^4R^5$ and $R^4$ and $R^5$ are taken together to form:

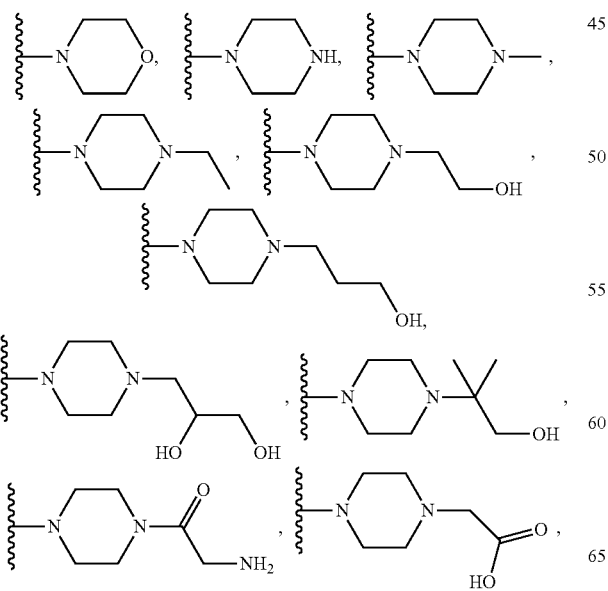

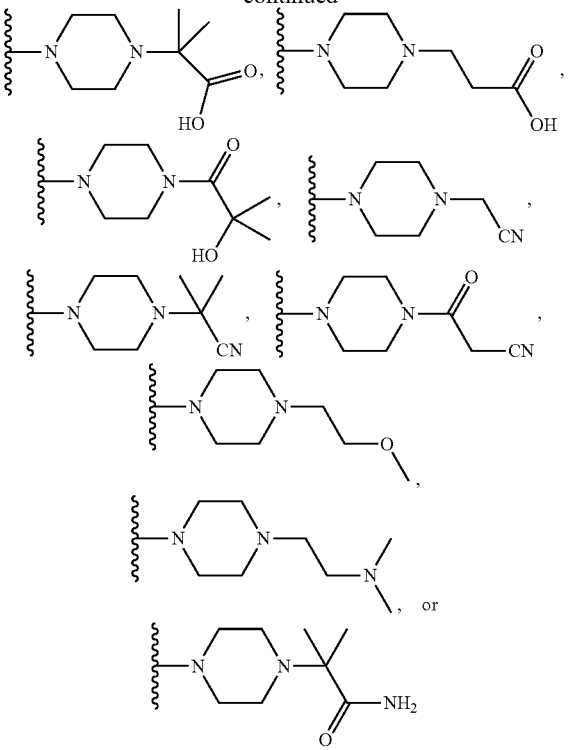

n. In another embodiment, $R^2$ is phenyl substituted with $(C_1$ to $C_6$ alkyl$)NR^4R^5$.
o. In yet a further embodiment, $R^2$ is phenyl substituted with $(C_1$ to $C_6$ alkyl$)NR^4R^5$ and $R^4$ and $R^5$ are $(C_1$ to $C_6$ hydroxyalkyl$)$.
p. In still another embodiment, $R^2$ is phenyl substituted with $(C_1$ to $C_6$ alkyl$)NR^4R^5$ and $NR^4R^5$ is:

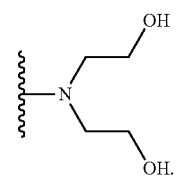

q. In a further embodiment, $R^2$ is phenyl substituted with $(C_1$ to $C_6$ alkyl$)NR^4R^5$ and $R^4$ and $R^5$ are joined to form an optionally substituted 6-membered ring.
r. In yet another embodiment, $R^2$ is phenyl substituted with $(C_1$ to $C_6$ alkyl$)NR^4R^5$ and $NR^4R^5$ are joined to form the 6-membered ring:

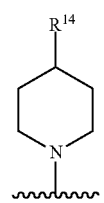

wherein, 1e is H, OH, C(O)OH, $C_1$ to $C_6$ alkyl, or $(C_1$ to $C_6$ alkyl$)CN$.

s. In another embodiment, $R^2$ is phenyl substituted with $(C_1$ to $C_6$ alkyl)$NR^4R^5$ and $NR^4R^5$ are joined to form the 6-membered ring:

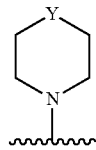

wherein, Y is O or $NR^9$; and $R^9$ is H, $C_1$ to $C_6$ alkyl, OH, $C_1$ to $C_6$ hydroxyalkyl, $C(O)(C_1$ to $C_6$ hydroxyalkyl), $C(O)(C_1$ to $C_6$ alkyl)CN, $(C_1$ to $C_6$ alkyl)CN, $(C_1$ to $C_6$ alkyl)$NH_2$, $(C_1$ to $C_6$ alkyl)halogen, $C(O)(C_1$ to $C_6$ alkyl)CN or $(C_1$ to $C_6$ alkyl)O$(C_1$ to $C_6$ alkyl)C(O)$(C_1$ to $C_6$ alkyl)$NH_2$.

t. In still a further embodiment, $R^2$ is phenyl substituted with $(C_1$ to $C_6$ alkyl)$NR^4R^5$ and $NR^4R^5$ are joined to form the 6-membered ring

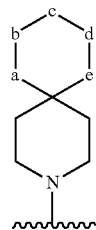

wherein, a, b, c, d, and e are, independently, absent, $(CH_2)$, $CH(R^3)$, or O; and $R^3$ is H or C(O)OH.

u. In yet another embodiment, $R^2$ is a heteroaryl substituted with $(C_1$ to $C_6$ alkyl)$NR^4R^5$.

v. In still another embodiment, $R^2$ is:

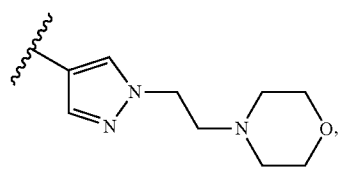

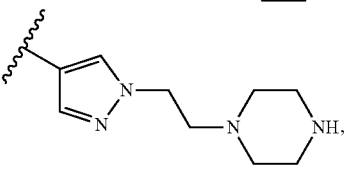

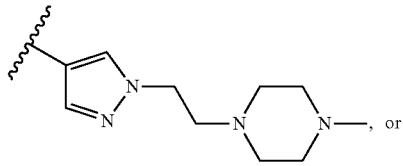, or

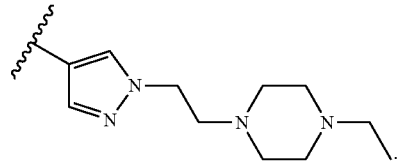.

w. In a further embodiment, $R^2$ is a heteroaryl substituted with $NR^4R^5$.

x. In still another embodiment, $R^2$ is a heteroaryl substituted with $NR^4R^5$ and the heteroaryl is pyridine.

y. In yet a further embodiment, $R^2$ is of the structure:

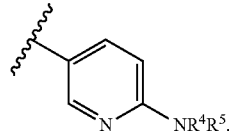

z. In another embodiment, $R^2$ is of the structure:

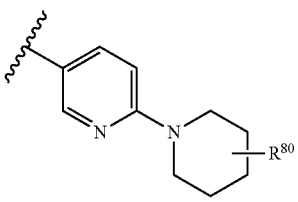

wherein, $R^{80}$ is OH, —$(C_1$ to $C_6$ alkyl)CN, $C_1$ to $C_6$ hydroxyalkyl, $(C_1$ to $C_6$ alkyl)C(O)$NH_2$, $(C_1$ to $C_6$ alkyl)heterocycle or —$(C_1$ to $C_6$ alkyl) C(O)OH.

aa. In still a further embodiment, $R^2$ is of the structure:

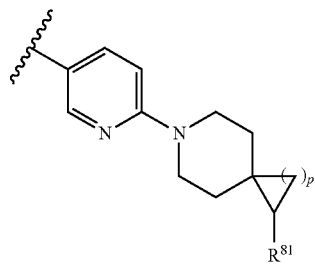

wherein, p is 1 to 6; and $R^{81}$ is H or C(O)OH.

bb. In another embodiment, $R^2$ is of the structure:

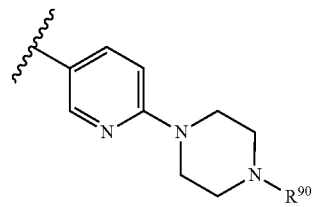

wherein, $R^{90}$ is H, $C_1$ to $C_6$ alkyl, $C(O)(C_1$ to $C_6$ alkyl)CN, $(C_1$ to $C_6$ alkyl)C(O)OH, or $C(O)C_1$ to $C_6$ hydroxyalkyl.

cc. In yet another embodiment, wherein $R^2$ is phenyl substituted with one or more $C_1$ to $C_6$ alkoxy, $(C_1$ to $C_6$ alkyl)halogen, $C_1$ to $C_6$ trifluoroalkoxy, $(C_1$ to $C_6$ alkyl)C(O)OH, halogen, optionally substituted $C_3$ to $C_8$ cycloalkyl, optionally substituted heterocyclyl, optionally substituted heteroaryl, —O—$(C_1$ to $C_6$ alkyl)C(O)OH, —O—$(C_1$ to $C_6$ alkyl)$NR^4R^5$, —O(optionally substituted heterocycle), —O$(C_1$ to $C_6$ alkyl)N$(C_1$ to $C_6$ alkyl)($C_1$ to $C_6$ alkyl), —O($C_1$ to $C_6$ alkyl)NH$_2$, $C_1$ to $C_6$ hydroxyalkyl, —O($C_1$ to $C_6$ hydroxyalkyl), —O($C_1$ to $C_6$ alkyl)C(O)OH, —$C_1$ to $C_6$ alkoxy-$C_1$ to $C_6$ alkoxy, —O(heterocycle)($C_1$ to $C_6$ hydroxyalkyl), —SO$_2$($C_1$ to $C_6$ alkyl), or —($C_1$ to $C_6$ alkyl)($C_1$ to $C_6$ alkoxy)halogen.

dd. In a further embodiment, wherein $R^2$ is of the structure:

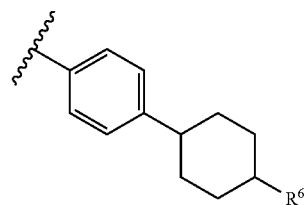

wherein, $R^6$ is H, ($C_1$ to $C_6$ alkyl)C(O)OH, or ($C_1$ to $C_6$ alkyl)CN.

ee. In still another embodiment, $R^2$ is of the structure:

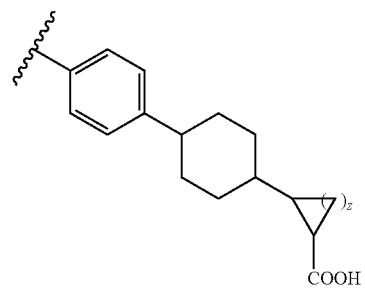

wherein, z is 1, 2, 3, 4, 5, or 6.

ff. In another embodiment, $R^2$ is of the structure:

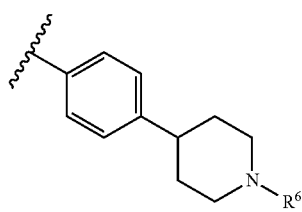

wherein, $R^6$ is H or ($C_1$ to $C_6$ alkyl)C(O)OH.

gg. In yet a further embodiment, $R^2$ is —O($C_1$ to $C_6$ alkyl)NR$^4$R$^5$.

hh. In still another embodiment, $R^2$ is of the structure:

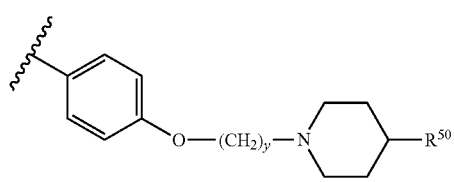

wherein, y is 2 to 6; and $R^{50}$ is H, OH, $C_1$ to $C_6$ alkyl, $C_1$ to $C_6$ hydroxyalkyl, or —($C_1$ to $C_6$ alkyl)C(O)OH.

ii. In further embodiment, $R^2$ is of the structure:

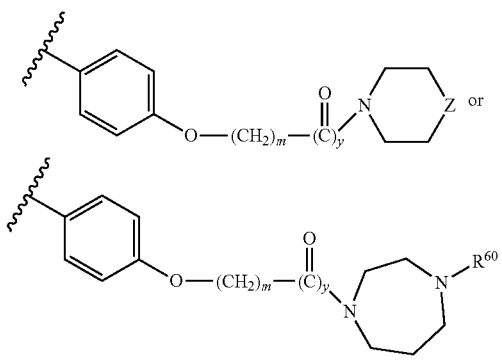

wherein, m is 2 to 6; y is 0 or 1; Z is O or NR$^{60}$; and $R^{60}$ is H, $C_1$ to $C_6$ alkyl, $C_1$ to $C_6$ hydroxyalkyl, —($C_1$ to $C_6$ alkyl)CN, —($C_1$ to $C_6$ alkyl)C(O)OH, —($C_1$ to $C_6$ alkyl)CONH$_2$, or —C(O)($C_1$ to $C_6$ alkyl)OH; wherein 2 hydrogen atoms attached to one carbon atom of the nitrogen-ring are replaced with an oxo or optionally substituted 3-8 membered spirocyclic ring.

jj. In yet another embodiment, $R^2$ is of the structure:

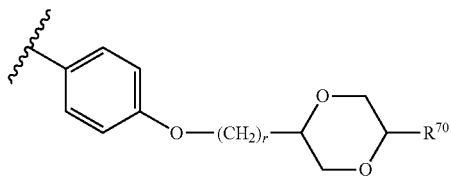

wherein, r is 2 to 6; and $R^{70}$ is H, C(O)OH or $C_1$ to $C_6$ hydroxyalkyl.

kk. In still a further embodiment, $R^2$ is:

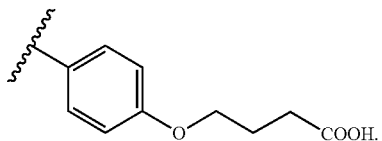 [SMILES: *c1ccc(OCCCC(=O)O)cc1]

ll. In another embodiment, $R^2$ is aryl substituted with —O—($C_1$ to $C_6$ alkyl)-heterocycle.

mm. In a further embodiment, $R^2$ is:

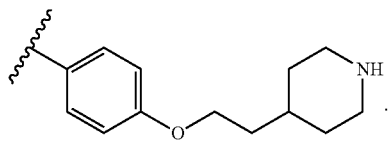 [SMILES: *c1ccc(OCCC2CCNCC2)cc1]

In some embodiments, the compound of Formula (I) is provided wherein $R^1$ is NR$^4$R$^5$, optionally substituted $C_1$ to $C_6$ alkoxy, optionally substituted $C_6$ to $C_{14}$ aryl, optionally substituted heteroaryl, optionally substituted 3-10 membered monocyclic or bicyclic cycloalkyl, or optionally substituted 3-10 membered monocyclic or bicyclic heterocyclyl. The 3-4 membered cycloalkyl and heterocyclyl rings are saturated. Hydrogen atoms on the same carbon atom of the cycloalkyl or heterocyclyl are optionally replaced with an optionally substituted 3-6 membered cycloalkyl or heterocyclyl to form a spirocycloalkyl or spiroheterocyclyl. In addition or alternatively, hydrogen atoms on the same atom of the cycloalkyl or heterocyclyl are optionally replaced with O to form an oxo substituent. $R^2$ is phenyl or 5-6 membered heteroaryl containing at least one N or NH in the backbone, wherein $R^2$ is optionally substituted with one or more $R^{19}$ and when $R^2$ is 4-pyridyl, the 4-pyridyl lacks a carbonyl substituent at the $2^{nd}$ position. $R^{19}$ is $NR^4R^5$, ($C_1$ to $C_6$ alkyl)$NR^4R^5$, $C_1$ to $C_6$ alkyl, $C(O)NR^4R^5$, $C_3$ to $C_8$ cycloalkyl substituted with one or more $R^{21}$, or heterocyclyl substituted with one or more $R^{21}$. $R^{21}$ is ($C_1$ to $C_6$ alkyl)CN, ($C_1$ to $C_6$ alkyl)C(O)OH, ($C_1$ to $C_6$ alkyl)C(O)NH$_2$, ($C_1$ to $C_6$ alkyl)C(O)NHCH$_2$CH$_2$OH, or ($C_1$ to $C_6$ alkyl)C(O)N(CH$_2$CH$_2$OH)$_2$. $R^4$ and $R^5$ are independently selected from among H, $C_1$ to $C_6$ alkyl, $C_1$ to $C_6$ hydroxyalkyl, and ($C_1$ to $C_6$ alkyl)N($C_1$ to $C_6$ alkyl)($C_1$ to $C_6$ alkyl). Alternatively, $R^4$ and $R^5$ are joined to form an optionally substituted 3-8 membered heterocyclyl optionally further containing one or more O, S(O)$_n$, or $NR^9$. $R^9$ is H, OH, ($C_1$ to $C_6$ alkyl)C(O)OH, ($C_1$ to $C_6$ alkyl)C(O)NH$_2$, ($C_1$ to $C_6$ alkyl)C(O)NHCH$_2$CH$_2$OH, ($C_1$ to $C_6$ alkyl)C(O)N(CH$_2$CH$_2$OH)$_2$, C(O)($C_1$ to $C_6$ alkyl)NH$_2$, C(O)($C_1$ to $C_6$ alkyl)OH, $C_1$ to $C_6$ hydroxyalkyl, or $C_1$ to $C_6$ alkyl and n is 0 to 2. In one embodiment, $R^9$ is CH$_2$CH$_2$OH. Hydrogen atoms on the same carbon atom of the heterocyclyl are optionally replaced with a 3-6 membered cycloalkyl or heterocyclyl optionally substituted with one or more $R^{20}$ to form a spirocycloalkyl or spiroheterocyclyl. $R^{20}$ is C(O)O($C_1$ to $C_6$ alkyl), C(O)OH, ($C_1$ to $C_6$ alkyl)C(O)OH, ($C_1$ to $C_6$ alkyl)C(O)NH$_2$, ($C_1$ to $C_6$ alkyl)C(O)NHCH$_2$CH$_2$OH, or ($C_1$ to $C_6$ alkyl)C(O)N(CH$_2$CH$_2$OH)$_2$. Alternatively, or in addition, hydrogen atoms on the same atom of any of the heterocyclyls or cycloalkyls of $R^9$ are optionally replaced with O to form an oxo substituent; or a pharmaceutically acceptable salt or ester thereof.

In some embodiments, the compound of Formula (I) is provided wherein $R^1$ is $NR^4R^5$, $C_1$ to $C_6$ alkoxy, optionally substituted phenyl, heteroaryl, optionally substituted 3-10 membered cycloalkyl, or optionally substituted 3-10 membered monocyclic or bicyclic heterocyclyl. Hydrogen atoms on the same carbon atom of the cycloalkyl or heterocyclyl are optionally replaced with an optionally substituted 3-6 membered cycloalkyl or heterocyclyl to form a spirocycloalkyl or spiroheterocyclyl. In addition or alternatively, hydrogen atoms on the same atom of the cycloalkyl or heterocyclyl are optionally replaced with O to form an oxo substituent. $R^2$ is phenyl or pyrazole, wherein $R^2$ is optionally substituted with one or more $R^{19}$. $R^{19}$ is $NR^4R^5$, ($C_1$ to $C_6$ alkyl)$NR^4R^5$, $C_1$ to $C_6$ alkyl, $C(O)NR^4R^5$, $C_3$ to $C_8$ cycloalkyl substituted with one or more $R^{21}$, or heterocyclyl substituted with one or more $R^{21}$. $R^{21}$ is ($C_1$ to $C_6$ alkyl)CN, ($C_1$ to $C_6$ alkyl)C(O)OH, ($C_1$ to $C_6$ alkyl)C(O)NH$_2$, ($C_1$ to $C_6$ alkyl)C(O)NHCH$_2$CH$_2$OH, or ($C_1$ to $C_6$ alkyl)C(O)N(CH$_2$CH$_2$OH)$_2$. $R^4$ and $R^5$ are (a) independently selected from among H, $C_1$ to $C_6$ alkyl, $C_1$ to $C_6$ hydroxyalkyl, and ($C_1$ to $C_6$ alkyl)N($C_1$ to $C_6$ alkyl)($C_1$ to $C_6$ alkyl) or (b) joined to form an optionally substituted 3-8 membered heterocyclyl optionally further containing one or more O, S(O)$_n$, or $NR^9$. $R^9$ is H, OH, $C_1$ to $C_6$ hydroxyalkyl, ($C_1$ to $C_6$ alkyl)C(O)OH, ($C_1$ to $C_6$ alkyl)C(O)NH$_2$, ($C_1$ to $C_6$ alkyl)C(O)NHCH$_2$CH$_2$OH, ($C_1$ to $C_6$ alkyl)C(O)N(CH$_2$CH$_2$OH)$_2$, C(O)($C_1$ to $C_6$ alkyl)NH$_2$, C(O)($C_1$ to $C_6$ alkyl)OH, or $C_1$ to $C_6$ alkyl and n is 0 to 2. In one embodiment, $R^9$ is CH$_2$CH$_2$OH. Hydrogen atoms on the same carbon atom of the heterocyclyl are optionally replaced with a 3-6 membered cycloalkyl or heterocyclyl to form a spirocycloalkyl or spiroheterocyclyl optionally substituted with one or more $R^{20}$. $R^{20}$ is C(O)O($C_1$ to $C_6$ alkyl), C(O)OH, ($C_1$ to $C_6$ alkyl)C(O)OH, ($C_1$ to $C_6$ alkyl)C(O)NH$_2$, ($C_1$ to $C_6$ alkyl)C(O)NHCH$_2$CH$_2$OH, or ($C_1$ to $C_6$ alkyl)C(O)N(CH$_2$CH$_2$OH)$_2$. Alternatively, or in addition, hydrogen atoms on the same atom of the heterocyclyl (b) or cycloalkyl are optionally replaced with O to form an oxo substituent; or a pharmaceutically acceptable salt or ester thereof.

In some embodiments, the compound of Formula (I) is provided wherein $R^1$ is $NR^4R^5$, $C_1$ to $C_6$ alkoxy, phenyl optionally substituted with C(O)O($C_1$ to $C_6$ alkyl), C(O)OH, O($C_1$ to $C_3$ perfluoroalkyl), $C_1$ to $C_6$ alkoxy, halogen, CH$_2$-heterocyclyl, or CH$_2$CN, 5-8 membered cycloalkyl, heteroaryl, or 3-10 membered monocyclic or bicyclic heterocyclyl optionally substituted with ($C_1$ to $C_6$ alkyl)C(O)OH, $C_1$ to $C_6$ alkyl, CN, C(O)OH, or ($C_1$ to $C_6$ alkyl)CN. Hydrogen atoms on the same carbon atom of the cycloalkyl or heterocyclyl are optionally replaced with an optionally substituted 3-6 membered cycloalkyl or heterocyclyl to form a spirocycloalkyl or spiroheterocyclyl. In addition or alternatively, hydrogen atoms on the same atom of the cycloalkyl or heterocyclyl are optionally replaced with O to form an oxo substituent. $R^2$ is phenyl or pyrazole, wherein $R^2$ is optionally substituted with one $R^{19}$. $R^{19}$ is $NR^4R^5$, ($C_1$ to $C_6$ alkyl)$NR^4R^5$, $C_1$ to $C_6$ alkyl, $C(O)NR^4R^5$, $C_3$ to $C_8$ cycloalkyl substituted with one or more $R^{21}$, or heterocyclyl substituted with one or more $R^{21}$. $R^{21}$ is ($C_1$ to $C_6$ alkyl)CN, ($C_1$ to $C_6$ alkyl)C(O)OH, ($C_1$ to $C_6$ alkyl)C(O)NH$_2$, ($C_1$ to $C_6$ alkyl)C(O)NHCH$_2$CH$_2$OH, or ($C_1$ to $C_6$ alkyl)C(O)N(CH$_2$CH$_2$OH)$_2$. $R^4$ and $R^5$ are (a) independently selected from among H, $C_1$ to $C_6$ alkyl, $C_1$ to $C_6$ hydroxyalkyl, and ($C_1$ to $C_6$ alkyl)N($C_1$ to $C_6$ alkyl)($C_1$ to $C_6$ alkyl). $R^4$ and $R^5$ may also be (b) joined to form a 5-8 membered heterocyclyl optionally further containing one or two O, S(O)$_n$, or $NR^9$. $R^9$ is H, OH, $C_1$ to $C_6$ hydroxyalkyl ($C_1$ to $C_6$ alkyl)C(O)OH, C(O)($C_1$ to $C_6$ alkyl)NH$_2$, C(O)($C_1$ to $C_6$ alkyl)OH, ($C_1$ to $C_6$ alkyl)C(O)NH$_2$, ($C_1$ to $C_6$ alkyl)C(O)NHCH$_2$CH$_2$OH, ($C_1$ to $C_6$ alkyl)C(O)N(CH$_2$CH$_2$OH)$_2$, or $C_1$ to $C_6$ alkyl and n is 0 to 2. In one embodiment, $R^9$ is CH$_2$CH$_2$OH. Hydrogen atoms on the same carbon atom of the heterocyclyl are optionally replaced with a 3-5 membered cycloalkyl optionally substituted with one or more $R^{20}$ to form a spirocycloalkyl. $R^{20}$ is C(O)O($C_1$ to $C_6$ alkyl), C(O)OH, ($C_1$ to $C_6$ alkyl)C(O)OH, ($C_1$ to $C_6$ alkyl)C(O)NH$_2$, ($C_1$ to $C_6$ alkyl)C(O)NHCH$_2$CH$_2$OH, or ($C_1$ to $C_6$ alkyl)C(O)N(CH$_2$CH$_2$OH)$_2$. Alternatively, or in addition, hydrogen atoms on the same atom of the heterocyclyl (b) or cycloalkyl (b) are optionally replaced with O to form an oxo substituent; or a pharmaceutically acceptable salt or ester thereof.

Some compounds useful in the practice of the invention possess one or more chiral centers, and the present invention includes use of each separate enantiomer of such compounds as well as mixtures of the enantiomers. Where multiple chiral centers exist in compounds of the present invention, the invention includes uses of compound(s) with each possible combination of chiral centers within a compound, as well as all possible enantiomeric and diastereomeric mixtures thereof. All chiral, diastereomeric, and racemic forms of a structure are intended, unless the specific stereochemistry or isomeric form is specifically indicated. It is well known in the art how to prepare optically active forms, such as by resolution of racemic forms or by synthesis from optically active starting materials.

The following definitions are used in connection with the compounds useful in the present invention unless the context indicates otherwise. In general, the number of carbon atoms present in a given group is designated "$C_x$-$C_y$", where x and y are the lower and upper limits, respectively. For example, a group designated as "$C_1$-$C_6$" contains from 1 to 6 carbon atoms. The carbon number as used in the definitions herein refers to carbon backbone and carbon branching, but does not include carbon atoms of the substituents, such as alkoxy substitutions and the like. Unless indicated otherwise, the nomenclature of substituents that are not explicitly defined herein are arrived at by naming from left to right the terminal portion of the functionality followed by the adjacent functionality toward the point of attachment. For example, the substituent "arylalkyloxycabonyl" refers to the group ($C_6$-$C_{14}$ aryl)-($C_1$-$C_6$ alkyl)-O—C(O)—. Terms not defined herein have the meaning commonly attributed to them by those skilled in the art.

"Alkyl" refers to a hydrocarbon chain that may be a straight chain or branched chain, containing the indicated number of carbon atoms, for example, a $C_1$-$C_{12}$ alkyl group may have from 1 to 12 (inclusive) carbon atoms in it. Examples of $C_1$-$C_6$ alkyl groups include, but are not limited to, methyl, ethyl, propyl, butyl, pentyl, hexyl, isopropyl, isobutyl, sec-butyl, tert-butyl, isopentyl, neopentyl, and isohexyl. Examples of $C_1$-$C_8$ alkyl groups include, but are not limited to, methyl, propyl, pentyl, hexyl, heptyl, 3-methylhex-1-yl, 2,3-dimethylpent-2-yl, 3-ethylpent-1-yl, octyl, 2-methylhept-2-yl, 2,3-dimethylhex-1-yl, and 2,3,3-trimethylpent-1-yl. An alkyl group can be unsubstituted or substituted with one or more of halogen, NH₂, (alkyl)NH, (alkyl)(alkyl)N—, —N(alkyl)C(O)(alkyl), —NHC(O)(alkyl), —NHC(O)H, —C(O)NH₂, —C(O)NH(alkyl), —C(O)N(alkyl)(alkyl), CN, OH, alkoxy, alkyl, C(O)OH, —C(O)O(alkyl), —C(O)(alkyl), aryl, heteroaryl, heterocyclyl, cycloalkyl, haloalkyl, aminoalkyl-, —OC(O)(alkyl), carboxyamidoalkyl-, and NO₂.

"Alkoxy" refers to the group R—O— where R is an alkyl group, as defined above. Exemplary $C_1$-$C_6$ alkoxy groups include but are not limited to methoxy, ethoxy, n-propoxy, 1-propoxy, n-butoxy and t-butoxy. An alkoxy group can be unsubstituted or substituted with one or more of halogen, OH, alkoxy, NH₂, (alkyl)amino-, di(alkyl)amino-, (alkyl)C(O)N($C_1$-$C_3$ alkyl)-, (alkyl)carboxyamido-, HC(O)NH—, H₂NC(O)—, (alkyl)NHC(O)—, di(alkyl)NC(O)—, CN, C(O)OH, (alkoxy)carbonyl-, (alkyl)C(O)—, aryl, heteroaryl, cycloalkyl, haloalkyl, amino($C_1$-$C_6$alkyl)-, (alkyl)carboxyl-, carboxyamidoalkyl-, or NO₂.

Aryl refers to an aromatic 6 to 14 membered hydrocarbon group. Examples of a $C_6$-$C_{14}$ aryl group include, but are not limited to, phenyl, α-naphthyl, β-naphthyl, biphenyl, anthryl, tetrahydronaphthyl, fluorenyl, indanyl, biphenylenyl, and acenanaphthyl. Examples of a $C_6$-$C_{10}$ aryl group include, but are not limited to, phenyl, α-naphthyl, β-naphthyl, biphenyl, and tetrahydronaphthyl. An aryl group can be unsubstituted or substituted with one or more of alkyl, halogen, haloalkyl, alkoxy, haloalkoxy, OH, hydroxyalkyl, —O-(hydroxyalkyl), —O-(alkyl)C(O)OH, -(alkyl)-(alkoxy)-halogen, NH₂, aminoalkyl-, dialkylamino-, C(O)OH, —C(O)O-(alkyl), —OC(O)(alkyl), —O-(alkyl)-N(alkyl)(alkyl), N-alkylamido-, —C(O)NH₂, (alkyl)amido-, NO₂, (aryl)alkyl, alkoxy, aryloxy, heteroaryloxy, (aryl)amino, (alkoxy)carbonyl-, (alkyl)amido-, (alkyl)amino, aminoalkyl-, alkylcarboxyl-, (alkyl)carboxyamido-, (aryl)alkyl-, (aryl)amino-, cycloalkenyl, di(alkyl)amino-, heteroaryl, (heteroaryl)alkyl-, heterocyclyl, —O-(heterocyclyl), heterocyclyl(alkyl)-, (hydroxyalkyl)NH—, (hydroxyalkyl)₂N, —SO₂(alkyl) or a spiro substituent.

The term "bicycle" or "bicyclic" as used herein refers to a molecule that features two fused rings, which rings are a cycloalkyl, heterocyclyl, or heteroaryl. In one embodiment, the rings are fused across a bond between two atoms. The bicyclic moiety formed therefrom shares a bond between the rings. In another embodiment, the bicyclic moiety is formed by the fusion of two rings across a sequence of atoms of the rings to form a bridgehead. Similarly, a "bridge" is an unbranched chain of one or more atoms connecting two bridgeheads in a polycyclic compound. In another embodiment, the bicyclic molecule is a "spiro" or "spirocyclic" moiety. The spirocyclic group is a carbocyclic or heterocyclic ring which bound through a single carbon atom of the spirocyclic moiety to a single carbon atom of a carbocyclic or heterocyclic moiety. In one embodiment, the spirocyclic group is a cycloalkyl and is bound to another cycloalkyl. In another embodiment, the spirocyclic group is a cycloalkyl and is bound to a heterocyclyl. In a further embodiment, the spirocyclic group is a heterocyclyl and is bound to another heterocyclyl. In still another embodiment, the spirocyclic group is a heterocyclyl and is bound to a cycloalkyl.

"(Aryl)alkyl" refers to an alkyl group, as defined above, wherein one or more of the alkyl group's hydrogen atoms has been replaced with an aryl group as defined above. ($C_6$-$C_{14}$ aryl)alkyl-moieties include benzyl, benzhydryl, 1-phenylethyl, 2-phenylethyl, 3-phenylpropyl, 2-phenylpropyl, 1-naphthylmethyl, 2-naphthylmethyl and the like. An (aryl)alkyl group can be unsubstituted or substituted with one or more of of halogen, CN, NH₂, OH, (alkyl)amino-, di(alkyl)amino-, (alkyl)C(O)N(alkyl)-, (alkyl)carboxyamido-, HC(O)NH—, H₂NC(O)—, (alkyl)NHC(O)—, di(alkyl)NC(O)—, CN, OH, alkoxy, alkyl, C(O)OH, (alkoxy)carbonyl-, (alkyl)C(O)—, aryl, heteroaryl, cycloalkyl, haloalkyl, amino(alkyl)-, (alkyl)carboxyl-, carboxyamidoalkyl, or NO₂.

"(Alkoxy)carbonyl-" refers to the group alkyl-O—C(O)—. Exemplary ($C_1$-$C_6$ alkoxy)carbonyl- groups include but are not limited to methoxy, ethoxy, n-propoxy, 1-propoxy, n-butoxy and t-butoxy. An (alkoxy)carbonyl group can be unsubstituted or substituted with one or more of halogen, OH, NH₂, (alkyl)amino-, di(alkyl)amino-, (alkyl)C(O)N(alkyl)-, (alkyl)carboxyamido-, HC(O)NH—, H₂NC(O)—, (alkyl)NHC(O)—, di(alkyl)NC(O)—, CN, alkoxy, C(O)OH, (alkoxy)carbonyl-, (alkyl)C(O)—, aryl, heteroaryl, cycloalkyl, haloalkyl, amino(alkyl)-, (alkyl)carboxyl-, carboxyamidoalkyl, or NO₂.

"(Alkyl)amido-" refers to a —C(O)NH— group in which the nitrogen atom of said group is attached to a $C_1$-$C_6$ alkyl group, as defined above. Representative examples of a ($C_1$-$C_6$ alkyl)amido- group include, but are not limited to, —C(O)NHCH₃, —C(O)NHCH₂CH₃, —C(O)NHCH₂CH₂CH₃, —C(O)NHCH₂CH₂CH₂CH₃, —C(O)NHCH₂CH₂CH₂CH₂CH₃, —C(O)NHCH(CH₃)₂, —C(O)NHCH₂CH(CH₃)₂, —C(O)NHCH(CH₃)CH₂CH₃, —C(O)NH—C(CH₃)₃ and —C(O)NHCH₂C(CH₃)₃.

"(Alkyl)amino-" refers to an —NH group, the nitrogen atom of said group being attached to a alkyl group, as defined above. Representative examples of an ($C_1$-$C_6$ alkyl) amino- group include, but are not limited to CH₃NH—, CH₃CH₂NH—, CH₃CH₂CH₂NH—, CH₃CH₂CH₂CH₂NH—, (CH₃)₂CHNH—, (CH₃)₂CHCH₂NH—, CH₃CH₂CH(CH₃)NH— and (CH₃)₃CNH—. An (alkyl)amino group can be unsubstituted or substituted on the alkyl moiety with one or more of halogen, NH₂, (alkyl)amino-, di(alkyl)amino-, (alkyl)C(O)N(alkyl)-, (alkyl)carboxyamido-, HC(O)NH—, H₂NC(O)—, (alkyl)NHC(O)—, di(alkyl)NC(O)—, CN, OH, alkoxy, alkyl, C(O)OH, (alkoxy)carbonyl-, (alkyl)C(O)—, aryl, heteroaryl, cycloalkyl, haloalkyl, amino(alkyl)-, (alkyl)carboxyl-, carboxyamidoalkyl-, or NO₂.

"Aminoalkyl-" refers to an alkyl group, as defined above, wherein one or more of the alkyl group's hydrogen atoms has been replaced with —NH₂; one or both H of the NH₂ may be replaced by a substituent.

"Alkylcarboxyl-" refers to an alkyl group, defined above that is attached to the parent structure through the oxygen atom of a carboxyl (C(O)—O—) functionality. Examples of (C₁-C₆alkyl)carboxyl- include acetoxy, propionoxy, propylcarboxyl, and isopentylcarboxyl.

"(Alkyl)carboxyamido-" refers to a —NHC(O)— group in which the carbonyl carbon atom of said group is attached to a C₁-C₆ alkyl group, as defined above. Representative examples of a (C₁-C₆ alkyl)carboxyamido- group include, but are not limited to, —NHC(O)CH₃, —NHC(O)CH₂CH₃, —NHC(O)CH₂CH₂CH₃, —NHC(O)CH₂CH₂CH₂CH₃, —NHC(O)CH₂CH₂CH₂CH₂CH₃, —NHC(O)CH(CH₃)₂, —NHC(O)CH₂CH(CH₃)₂, —NHC(O)CH(CH₃)CH₂CH₃, —NHC(O)—C(CH₃)₃ and —NHC(O)CH₂C(CH₃)₃.

"(Aryl)amino" refers to a radical of formula (aryl)-NH—, wherein aryl is as defined above. "(Aryl)oxy" refers to the group Ar—O— where Ar is an aryl group, as defined above.

"Cycloalkyl" refers to a non-aromatic, saturated, partially saturated, monocyclic, bicyclic or polycyclic hydrocarbon 3 to 12 membered ring system. Representative examples of a C₃-C₁₂ cycloalkyl include, but are not limited to, cyclopropyl, cyclopentyl, cycloheptyl, cyclooctyl, decahydronaphthalen-1-yl, octahydro-1H-inden-2-yl, decahydro-1H-benzo[7]annulen-2-yl, and dodecahydros-indacen-4-yl. Representative examples of a C₃-C₁₀ cycloalkyl include, but are not limited to, cyclopropyl, cyclobutyl, cyclopentyl, cyclohexyl, cycloheptyl, cyclooctyl, decahydronaphthalen-1-yl, and octahydro-1H-inden-2-yl. Representative examples of a C₃-C₈ cycloalkyl include, but are not limited to, cyclopropyl, cyclobutyl, cyclopentyl, cyclohexyl, cycloheptyl, cyclooctyl, and octahydropentalen-2-yl. A cycloalkyl can be unsubstituted or substituted with one or more of halogen, NH₂, (alkyl)NH, (alkyl)(alkyl)N—, —N(alkyl)C(O)(alkyl), —NHC(O)(alkyl), —NHC(O)H, —C(O)NH₂, —C(O)NH(alkyl), —C(O)N(alkyl)(alkyl), CN, OH, alkoxy, alkyl, C(O)OH, —C(O)O(alkyl), —C(O) alkyl), aryl, heteroaryl, cycloalkyl, haloalkyl, aminoalkyl-, —OC(O)(alkyl), carboxyamidoalkyl-, and NO₂. Additionally, each of any two hydrogen atoms on the same carbon atom of the carbocyclic ring can be replaced by an oxygen atom to form an oxo (=O) substituent.

"Halo" or "halogen" refers to —F, —Cl, —Br and —I.

"C₁-C₆ haloalkyl" refers to a C₁-C₆ alkyl group, as defined above, wherein one or more of the C₁-C₆ alkyl group's hydrogen atoms has been replaced with F, Cl, Br, or I. Each substitution can be independently selected from F, Cl, Br, or I. Representative examples of an C₁-C₆ haloalkyl-group include, but are not limited to, —CH₂F, —CCl₃, —CF₃, CH₂CF₃, —CH₂Cl, —CH₂CH₂Br, —CH₂CH₂I, —CH₂CH₂CH₂F, —CH₂CH₂CH₂Cl, —CH₂CH₂CH₂CH₂Br, —CH₂CH₂CH₂CH₂I, —CH₂CH₂CH₂CH₂CH₂Br, —CH₂CH₂CH₂CH₂CH₂I, —CH₂CH(Br)CH₃, —CH₂CH(Cl)CH₂CH₃, —CH(F)CH₂CH₃ and —C(CH₃)₂(CH₂Cl).

"Heteroaryl" refers to a monocyclic, bicyclic, or polycyclic aromatic ring system containing at least one ring atom selected from the heteroatoms oxygen, sulfur and nitrogen. Examples of C₁-C₉ heteroaryl groups include furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, benzoxazole, benzothiazole, benzofuran, benzisoxazole, benzimidazole, N-methylbenzimidazole, azabenzimidazole, indazole, quinazoline, quinoline, and isoquinoline. Bicyclic C₁-C₉ heteroaryl groups include those where a phenyl, pyridine, pyrimidine or pyridazine ring is fused to a 5 or 6-membered monocyclic heteroaryl ring having one or two nitrogen atoms in the ring, one nitrogen atom together with either one oxygen or one sulfur atom in the ring, or one O or S ring atom. Examples of monocyclic C₁-C₄ heteroaryl groups include 2H-tetrazole, 3H-1,2,4-triazole, furan, thiophene, oxazole, thiazole, isoxazole, isothiazole, imidazole, and pyrrole. A heteroaryl group can be unsubstituted or substituted with one or more of C₁-C₆ alkyl, halogen, haloalkyl, OH, CN, hydroxyalkyl, NH₂, aminoalkyl-, dialkylamino-, C(O)OH, —C(O)O-(alkyl), —OC(O)(alkyl), N-alkylamido-, —C(O)NH₂, (alkyl)amido-, —NO₂, (aryl) alkyl, alkoxy, aryloxy, heteroaryloxy, (aryl)amino, (alkoxy) carbonyl-, (alkyl)amido-, (alkyl)amino, aminoalkyl-, alkylcarboxyl-, (alkyl)carboxyamido-, (aryl)alkyl-, (aryl)amino-, cycloalkenyl, di(alkyl)amino-, heteroaryl, (heteroaryl) alkyl-, heterocyclyl, heterocyclyl(alkyl)-, (hydroxyalkyl) NH—, (hydroxyalkyl)₂N or a Spiro substituent.

"Heterocycle" or "heterocyclyl" refers to monocyclic, bicyclic, polycyclic, or bridged head molecules in which at least one ring atom is a heteroatom. A heterocycle may be saturated or partially saturated. Exemplary C₁-C₉ heterocyclyl groups include but are not limited to aziridine, oxirane, oxirene, thiirane, pyrroline, pyrrolidine, dihydrofuran, tetrahydrofuran, dihydrothiophene, tetrahydrothiophene, dithiolane, piperidine, 1,2,3,6-tetrahydropyridine-1-yl, tetrahydropyran, pyran, thiane, thiine, piperazine, azepane, diazepane, oxazine, 5,6-dihydro-4H-1,3-oxazin-2-yl, 2,5-diazabicyclo[2.2.1]heptane, 2,5-diazabicyclo[2.2.2]octane, 3,6-diazabicyclo[3.1.1]heptane, 3,8-diazabicyclo[3.2.1]octane, 6-oxa-3,8-diazabicyclo[3.2.1]octane, 7-oxa-2,5-diazabicyclo[2.2.2]octane, 2,7-dioxa-5-azabicyclo[2.2.2]octane, 2-oxa-5-azabicyclo[2.2.1]heptane-5-yl, 2-oxa-5-azabicyclo[2.2.2]octane, 3,6-dioxa-8-azabicyclo[3.2.1]octane, 3-oxa-6-azabicyclo[3.1.1]heptane, 3-oxa-8-azabicyclo[3.2.1]octan-8-yl, 5,7-dioxa-2-azabicyclo[2.2.2]octane, 6,8-dioxa-3-azabicyclo[3.2.1]octane, 6-oxa-3-azabicyclo[3.1.1]heptane, 8-oxa-3-azabicyclo[3.2.1]octan-3-yl, 2-methyl-2,5-diazabicyclo[2.2.1]heptane-5-yl, 1,3,3-trimethyl-6-azabicyclo[3.2.1]oct-6-yl, 3-hydroxy-8-azabicyclo[3.2.1]octan-8-yl-, 7-methyl-3-oxa-7,9-diazabicyclo[3.3.1]nonan-9-yl, 9-oxa-3-azabicyclo[3.3.1]nonan-3-yl, 3-oxa-9-azabicyclo[3.3.1]nonan-9-yl, 3,7-dioxa-9-azabicyclo[3.3.1]nonan-9-yl, 4-methyl-3,4-dihydro-2H-1,4-benzoxazin-7-yl, thiazine, dithiane, and dioxane. The contemplated heterocycle rings or ring systems have a minimum of 3 members. Therefore, for example, C₁ heterocyclyl radicals would include but are not limited to oxaziranyl, diaziridinyl, and diazirinyl, C₂ heterocyclyl radicals include but are not limited to aziridinyl, oxiranyl, and diazetidinyl, C₉ heterocyclyl radicals include but are not limited to azecanyl, tetrahydroquinolinyl, and perhydroisoquinolinyl. A heterocyclyl group can be unsubstituted or substituted with one or more of alkyl, halogen, alkoxy, haloalkyl, OH, hydroxyalkyl, —C(O)-(hydroxyalkyl), NH₂, aminoalkyl-, dialkylamino-, C(O)OH, —C(O)O-(alkyl), —OC(O)(alkyl), N-alkylamido-, —C(O)NH₂, (alkyl)amido-, —C(O)-(alkyl)-CN, (alkyl)-CN, or NO₂.

"Heterocyclyl(alkyl)-" refers to an alkyl group, as defined above, wherein one or more of the alkyl group's hydrogen atoms has been replaced with a heterocycle group as defined above. Heterocyclyl(C₁-C₆ alkyl)- moieties include 1-piperazinylethyl, 4-morpholinylpropyl, 6-piperazinylhexyl, and the like. A heterocyclyl(alkyl) group can be unsubstituted or substituted with one or more of halogen, NH₂, (alkyl)amino-, di(alkyl)amino-, (alkyl)C(O)N(alkyl)-, (alkyl)carboxyamido-, HC(O)NH—, H₂NC(O)—, (alkyl)NHC(O)—, di(alkyl)NC(O)—, CN, OH, alkoxy, alkyl, C(O)OH, (alkoxy)carbonyl-, (alkyl)C(O)—, 4- to 7-membered monocyclic heterocycle, aryl, heteroaryl, or cycloalkyl.

"Heteroaryl(alkyl)" refers to a heteroaryl which is attached to an alkyl group and the heteroaryl is defined above.

"Hydroxyalkyl" refers to a alkyl group, as defined above, wherein one or more of the alkyl group's hydrogen atoms has been replaced with OH groups. Examples of $C_1$-$C_6$ hydroxyalkyl moieties include, for example, —CH₂OH, —CH₂CH₂OH, —CH₂CH₂CH₂OH, —CH₂CH(OH)CH₂OH, —CH₂CH(OH)CH₃, —CH(CH₃)CH₂OH and higher homologs.

"Perfluoroalkyl-" refers to alkyl group, defined above, having two or more fluorine atoms. Examples of a $C_1$-$C_6$ perfluoroalkyl- group include CF₃, CH₂CF₃, CF₂CF₃ and CH(CF₃)₂.

Representative "pharmaceutically acceptable salts" include, e.g., water-soluble and water-insoluble salts, such as the acetate, benzenesulfonate, benzoate, bicarbonate, bisulfate, bitartrate, bromide, butyrate, calcium, chloride, choline, citrate, edisylate (camphorsulfonate), fumarate, gluconate, glucuronate, glutamate, hydrobromide, hydrochloride, lauryl sulfate, malate, maleate, mandelate, mesylate, palmitate, pantothenate, phosphate, potassium, propionate, p-toluenesulfonate, salicylate, sodium, stearate, succinate, and sulfate salts. Representative pharmaceutically acceptable esters include acetyl, propionyl, benzoyl, nicotinoyl and phenylacetyl ester derivatives of compounds of Formula (I) that have a hydroxyl group.

Examples of specific compounds falling within Formula (I) that may be useful in the methods of the present invention are set forth in Table I, below.

TABLE 1

| Structure | IUPAC Name |
|---|---|
| 1 | 4-(4-morpholinophenylamino)-2-phenylpyrimido[4,5-d]pyridazin-5(6H)-one |
| 2 | methyl 4-(5-oxo-4-(4-(piperazin-1-ylmethyl)phenylamino)-5,6-dihydropyrimido[4,5-d]pyridazin-2-yl)benzoate hydrochloride |

TABLE 1-continued
| Structure | IUPAC Name |
|---|---|
| 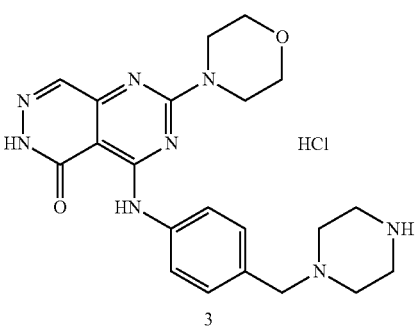 [SMILES: O=c1[nH]ncc2nc(N3CCOCC3)nc(Nc3ccc(CN4CCNCC4)cc3)c12 ; Cl] 3 | 2-morpholino-4-(4-(piperazin-1-ylmethyl)phenylamino)pyrimido[4,5-d]pyridazin-5(6H)-one hydrochloride |
| 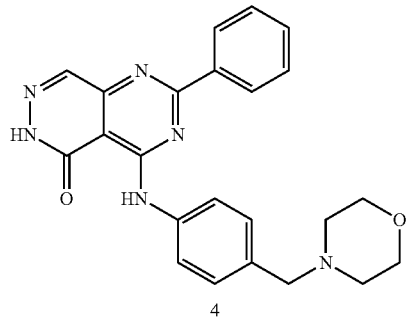 [SMILES: O=c1[nH]ncc2nc(-c3ccccc3)nc(Nc3ccc(CN4CCOCC4)cc3)c12] 4 | 4-(4-(morpholinomethyl)phenylamino)-2-phenylpyrimido[4,5-d]pyridazin-5(6H)-one |
| 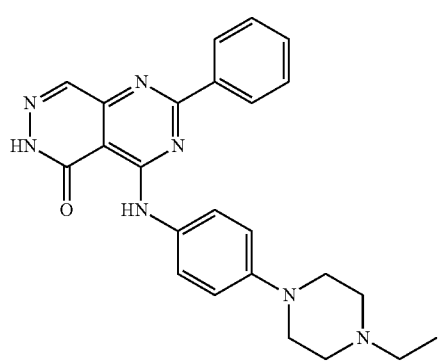 5 | 4-(4-(4-ethylpiperazin-1-yl)phenylamino)-2-phenylpyrimido[4,5-d]pyridazin-5(6H)-one |
| 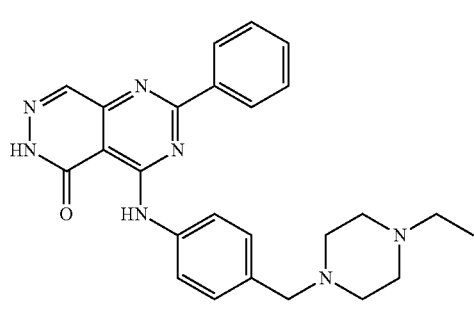 6 | 4-(4-((4-ethylpiperazin-1-yl)methyl)phenylamino)-2-phenylpyrimido[4,5-d]pyridazin-5(6H)-one |

TABLE 1-continued
| Structure | IUPAC Name |
|---|---|
| 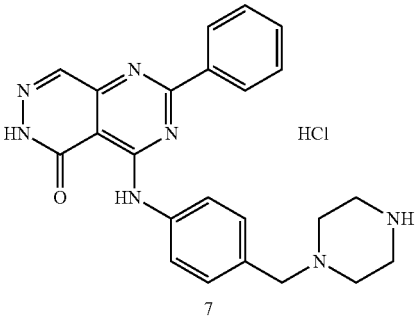 [SMILES: O=c1[nH]ncc2nc(-c3ccccc3)nc(Nc3ccc(CN4CCNCC4)cc3)c12 ; Cl] 7 | 2-phenyl-4-(4-(piperazin-1-ylmethyl)phenylamino)pyrimido[4,5-d]pyridazin-5(6H)-one hydrochloride |
| 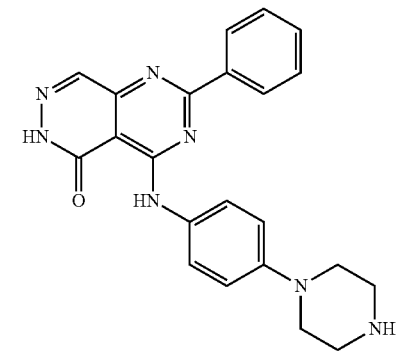 8 | 2-phenyl-4-(4-(piperazin-1-yl)phenylamino)pyrimido[4,5-d]pyridazin-5(6H)-one |
| 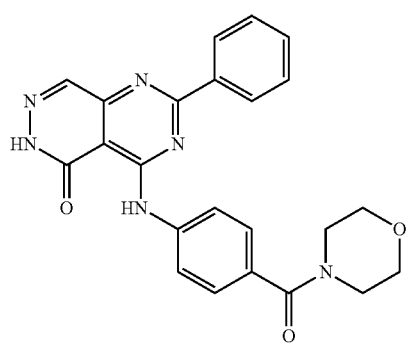 9 | 4-(4-(morpholine-4-carbonyl)phenylamino)-2-phenylpyrimido[4,5-d]pyridazin-5(6H)-one |
| 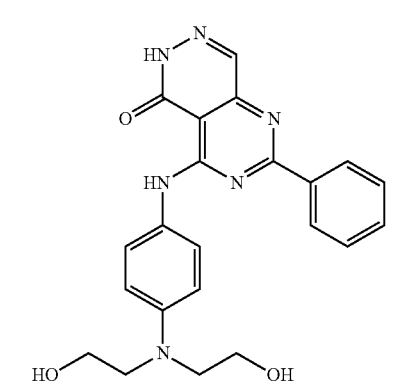 10 | 4-(4-(bis(2-hydroxyethyl)amino)phenylamino)-2-phenylpyrimido[4,5-d]pyridazin-5(6H)-one |

TABLE 1-continued
| Structure | IUPAC Name |
|---|---|
| 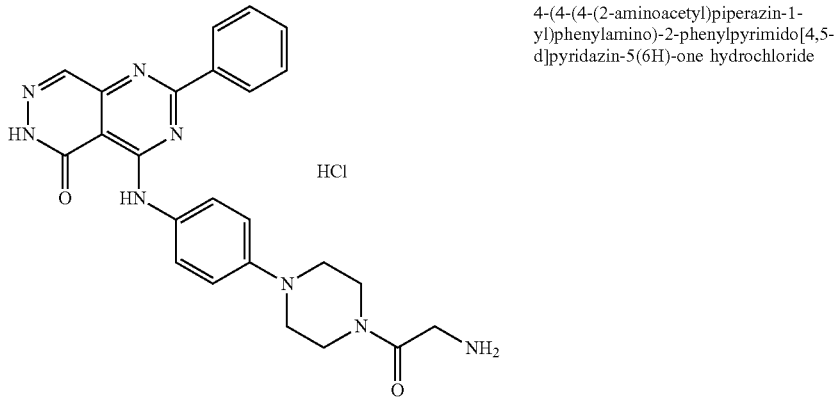 11 | 4-(4-(4-(2-aminoacetyl)piperazin-1-yl)phenylamino)-2-phenylpyrimido[4,5-d]pyridazin-5(6H)-one hydrochloride |
| 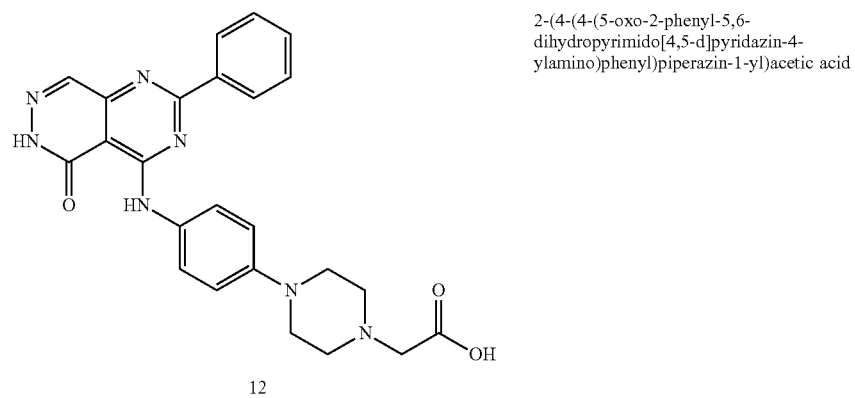 12 | 2-(4-(4-(5-oxo-2-phenyl-5,6-dihydropyrimido[4,5-d]pyridazin-4-ylamino)phenyl)piperazin-1-yl)acetic acid |
| 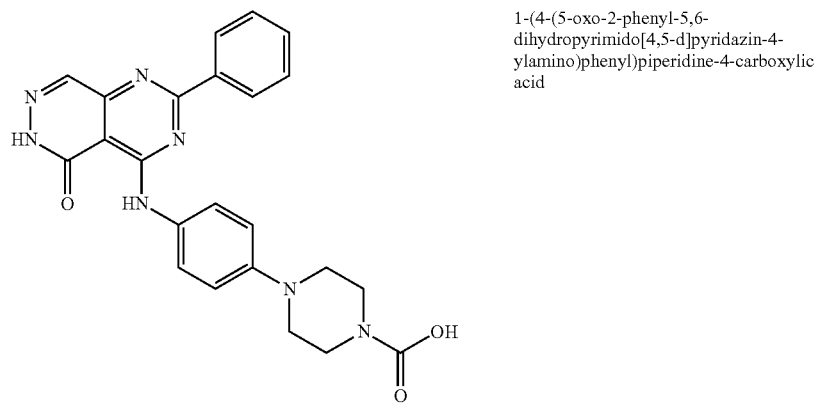 13 | 1-(4-(5-oxo-2-phenyl-5,6-dihydropyrimido[4,5-d]pyridazin-4-ylamino)phenyl)piperidine-4-carboxylic acid |

TABLE 1-continued
| Structure | IUPAC Name |
|---|---|
| 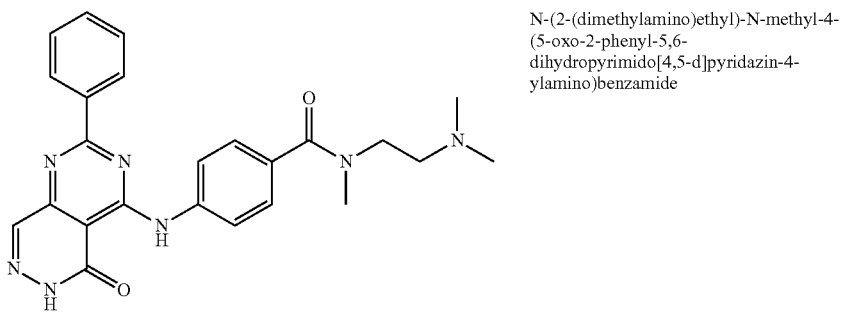 14 | 4-(4-(4-(2-aminoacetyl)piperazin-1-yl)phenylamino)-2-phenylpyrimido[4,5-d]pyridazin-5(6H)-one |
| 15 | N-(2-(dimethylamino)ethyl)-N-methyl-4-(5-oxo-2-phenyl-5,6-dihydropyrimido[4,5-d]pyridazin-4-ylamino)benzamide |
| 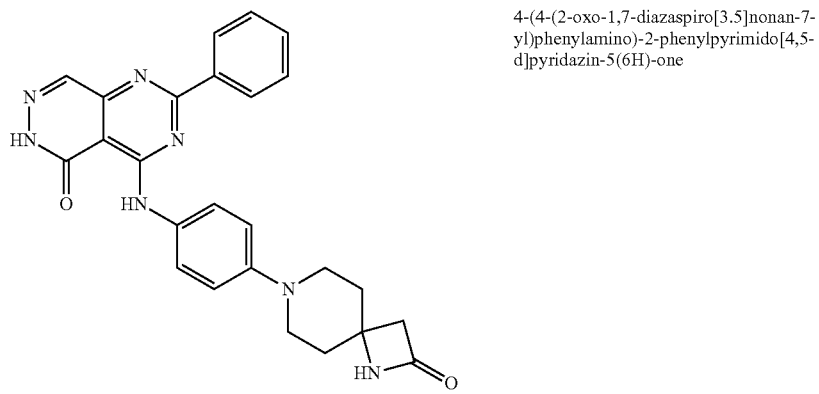 16 | 4-(4-(2-oxo-1,7-diazaspiro[3.5]nonan-7-yl)phenylamino)-2-phenylpyrimido[4,5-d]pyridazin-5(6H)-one |

TABLE 1-continued

| Structure | IUPAC Name |
|---|---|
| 17 | 4-(4-(2-oxa-7-azaspiro[3.5]nonan-7-yl)phenylamino)-2-phenylpyrimido[4,5-d]pyridazin-5(6H)-one |
| 18 | 4-(4-morpholinophenylamino)-2-(6-azaspiro[2.5]octan-6-yl)pyrimido[4,5-d]pyridazin-5(6H)-one |
| 19 | 6-(4-(5-oxo-2-phenyl-5,6-dihydropyrimido[4,5-d]pyridazin-4-ylamino)phenyl)-6-azaspiro[2.5]octane-1-carboxylic acid |

TABLE 1-continued
| Structure | IUPAC Name |
|---|---|
| 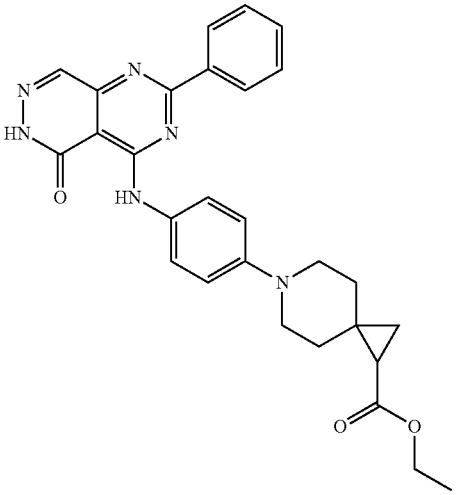 20 | ethyl 6-(4-(5-oxo-2-phenyl-5,6-dihydropyrimido[4,5-d]pyridazin-4-ylamino)phenyl)-6-azaspiro[2.5]octane-1-carboxylate |
| 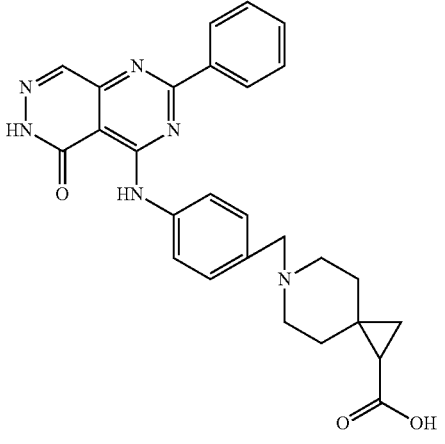 21 | 6-(4-(5-oxo-2-phenyl-5,6-dihydropyrimido[4,5-d]pyridazin-4-ylamino)benzyl)-6-azaspiro[2.5]octane-1-carboxylic acid |
| 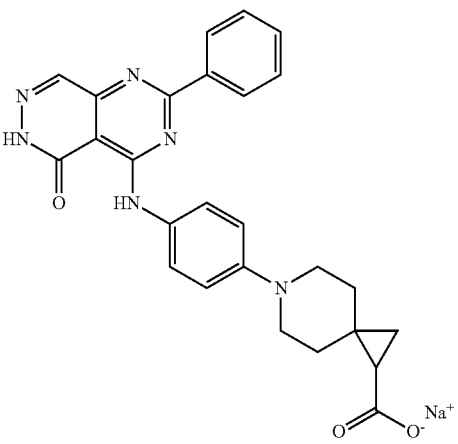 22 | sodium 6-(4-(5-oxo-2-phenyl-5,6-dihydropyrimido[4,5-d]pyridazin-4-ylamino)phenyl)-6-azaspiro[2.5]octane-1-carboxylate |

TABLE 1-continued

| Structure | IUPAC Name |
| --- | --- |
| 23 | 4-(4-(2-oxa-7-azaspiro[3.5]nonan-7-ylmethyl)phenylamino)-2-phenylpyrimido[4,5-d]pyridazin-5(6H)-one |
| 24 | 4-(4-(piperazin-1-ylmethyl)phenylamino)-2-(thiophen-3-yl)pyrimido[4,5-d]pyridazin-5(6H)-one hydrochloride |
| 25 | 6-(5-oxo-4-(4-(piperazin-1-ylmethyl)phenylamino)-5,6-dihydropyrimido[4,5-d]pyridazin-2-yl)-6-azaspiro[2.5]octane-1-carboxylic acid hydrochloride |
| 26 | 4-(4-(4-ethylpiperazin-1-yl)phenylamino)-2-morpholinopyrimido[4,5-d]pyridazin-5(6H)-one |

TABLE 1-continued

| Structure | IUPAC Name |
|---|---|
| 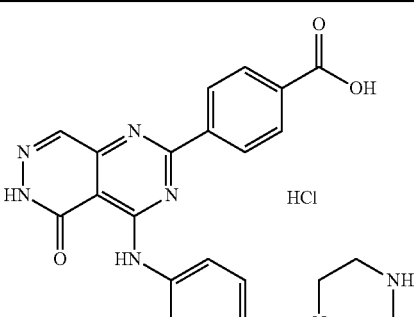 27 | 4-(5-oxo-4-(4-(piperazin-1-ylmethyl)phenylamino)-5,6-dihydropyrimido[4,5-d]pyridazin-2-yl)benzoic acid hydrochloride |
| 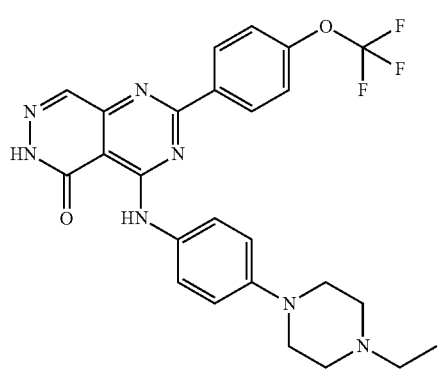 28 | 4-(4-(4-ethylpiperazin-1-yl)phenylamino)-2-(4-(trifluoromethoxy)phenyl)pyrimido[4,5-d]pyridazin-5(6H)-one |
| 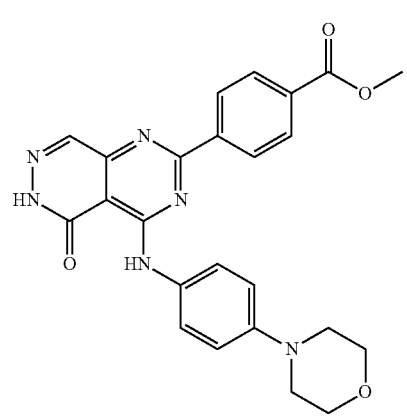 29 | methyl 4-(4-(4-morpholinophenylamino)-5-oxo-5,6-dihydropyrimido[4,5-d]pyridazin-2-yl)benzoate |
| 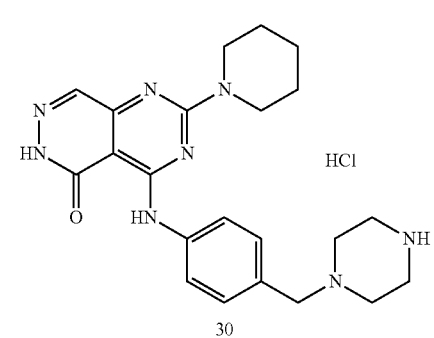 [SMILES: O=c1[nH]ncc2nc(N3CCCCC3)nc(Nc3ccc(CN4CCNCC4)cc3)c12 ; Cl] 30 | 4-(4-(piperazin-1-ylmethyl)phenylamino)-2-(piperidin-1-yl)pyrimido[4,5-d]pyridazin-5(6H)-one hydrochloride |

TABLE 1-continued

| Structure | IUPAC Name |
|---|---|
| 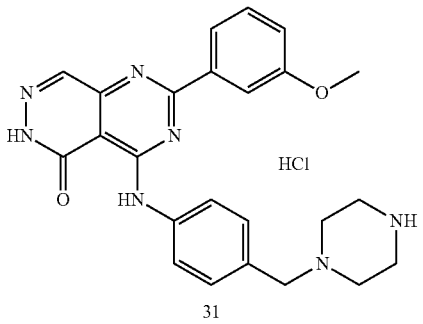 [SMILES: COc1cccc(-c2nc(Nc3ccc(CN4CCNCC4)cc3)c3c(=O)[nH]ncc3n2)c1 ; Cl] 31 | 2-(3-methoxyphenyl)-4-(4-(piperazin-1-ylmethyl)phenylamino)pyrimido[4,5-d]pyridazin-5(6H)-one hydrochloride |
| 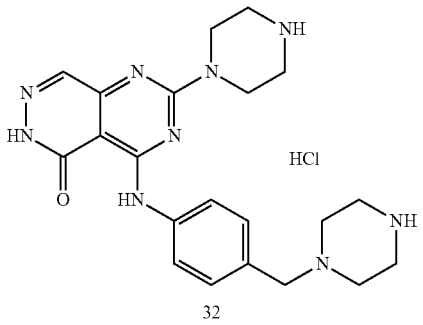 [SMILES: O=c1[nH]ncc2nc(N3CCNCC3)nc(Nc3ccc(CN4CCNCC4)cc3)c12 ; Cl] 32 | 2-(piperazin-1-yl)-4-(4-(piperazin-1-ylmethyl)phenylamino)pyrimido[4,5-d]pyridazin-5(6H)-one dihydrochloride |
| 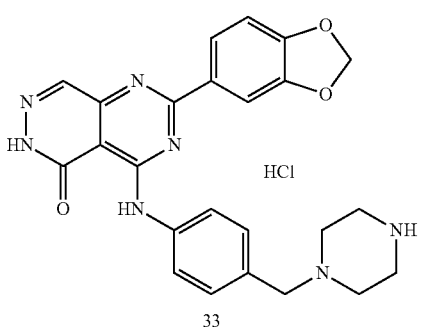 [SMILES: O=c1[nH]ncc2nc(-c3ccc4c(c3)OCO4)nc(Nc3ccc(CN4CCNCC4)cc3)c12 ; Cl] 33 | 2-(benzo[d][1,3]dioxol-5-yl)-4-(4-(piperazin-1-ylmethyl)phenylamino)pyrimido[4,5-d]pyridazin-5(6H)-one hydrochloride |
| 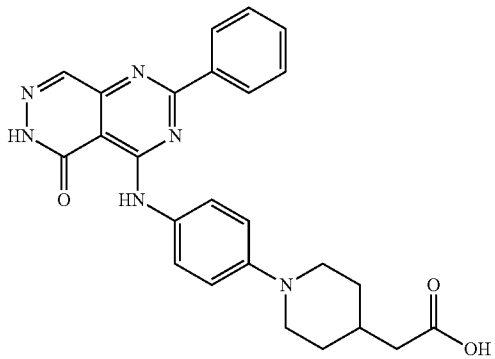 34 | 2-(1-(4-(5-oxo-2-phenyl-5,6-dihydropyrimido[4,5-d]pyridazin-4-ylamino)phenyl)piperidin-4-yl)acetic acid |

TABLE 1-continued
| Structure | IUPAC Name |
|---|---|
| 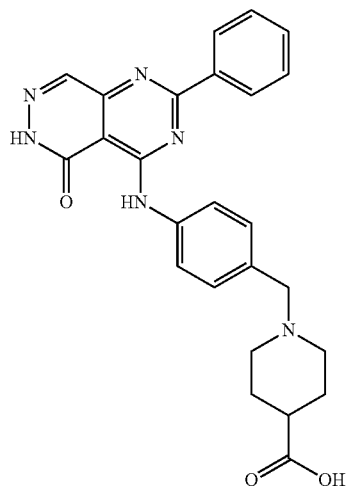 35 | 1-(4-(5-oxo-2-phenyl-5,6-dihydropyrimido[4,5-d]pyridazin-4-ylamino)benzyl)piperidine-4-carboxylic acid |
| 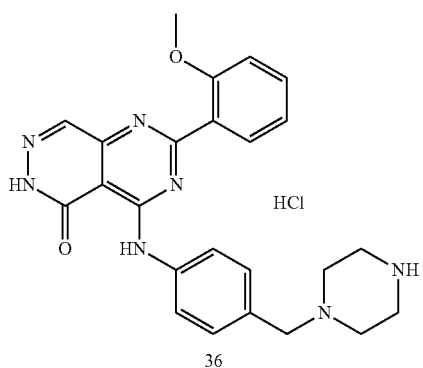 [SMILES: COc1ccccc1-c1nc(Nc2ccc(CN3CCNCC3)cc2)c2c(=O)[nH]ncc2n1 ; Cl] 36 | 2-(2-methoxyphenyl)-4-(4-(piperazin-1-ylmethyl)phenylamino)pyrimido[4,5-d]pyridazin-5(6H)-one hydrochloride |
| 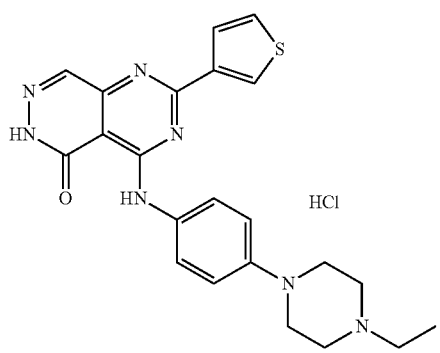 37 | 4-(4-(4-ethylpiperazin-1-yl)phenylamino)-2-(thiophen-3-yl)pyrimido[4,5-d]pyridazin-5(6H)-one hydrochloride |

TABLE 1-continued

| Structure | IUPAC Name |
|---|---|
| 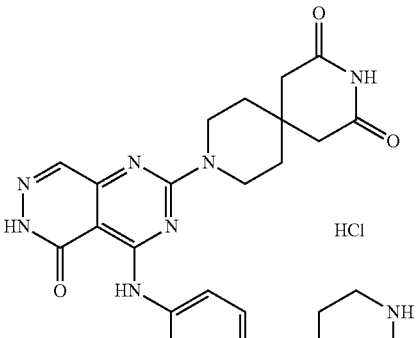 38 | 9-(5-oxo-4-(4-(piperazin-1-ylmethyl)phenylamino)-5,6-dihydropyrimido[4,5-d]pyridazin-2-yl)-3,9-diazaspiro[5.5]undecane-2,4-dione hydrochloride |
| 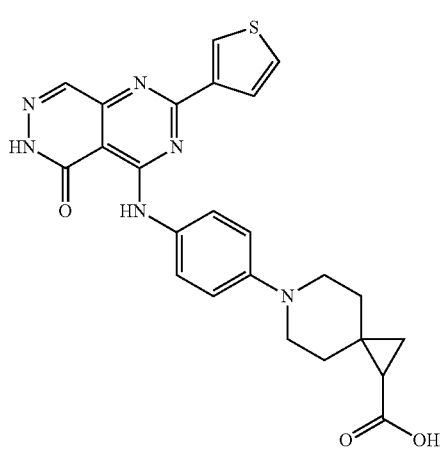 39 | 6-(4-(5-oxo-2-(thiophen-3-yl)-5,6-dihydropyrimido[4,5-d]pyridazin-4-ylamino)phenyl)-6-azaspiro[2.5]octane-1-carboxylic acid |
| 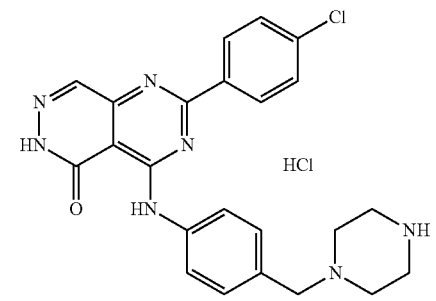 40 | 2-(4-chlorophenyl)-4-(4-(piperazin-1-ylmethyl)phenylamino)pyrimido[4,5-d]pyridazin-5(6H)-one hydrochloride |
| 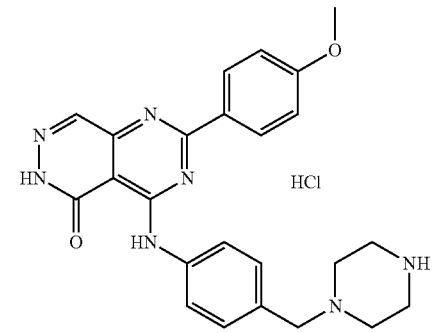 41 | 2-(4-methoxyphenyl)-4-(4-(piperazin-1-ylmethyl)phenylamino)pyrimido[4,5-d]pyridazin-5(6H)-one hydrochloride |

TABLE 1-continued
| Structure | IUPAC Name |
|---|---|
| 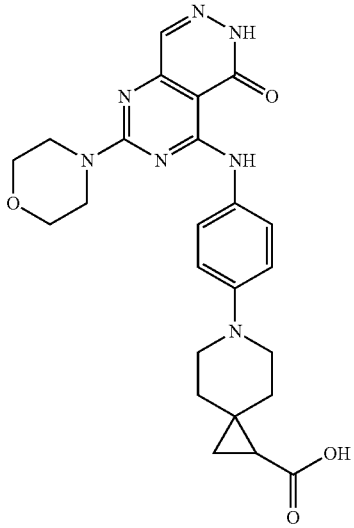 42 | 6-(4-((2-morpholino-5-oxo-5,6-dihydropyrimido[4,5-d]pyridazin-4-yl)amino)phenyl)-6-azaspiro[2.5]octane-1-carboxylic acid |
| 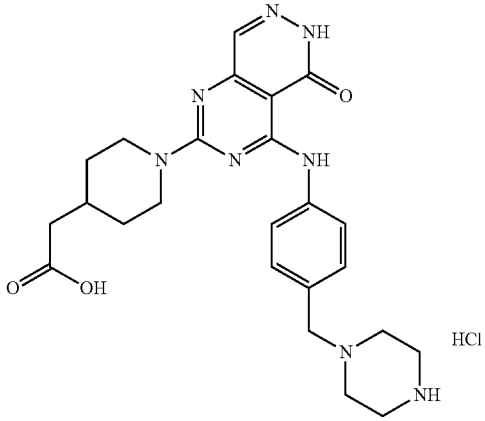 43 | 2-(1-(5-oxo-4-((4-(piperazin-1-ylmethyl)phenyl)amino)-5,6-dihydropyrimido[4,5-d]pyridazin-2-yl)piperidin-4-yl)acetic acid hydrochloride |
| 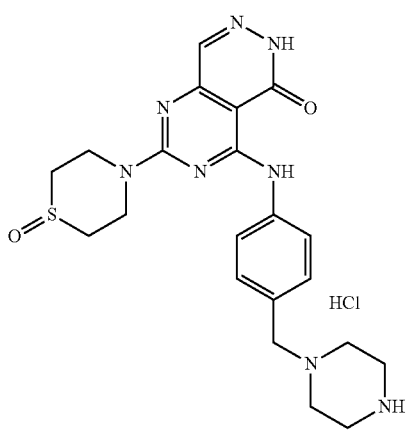 44 | 2-(1-oxidothiomorpholino)-4-((4-(piperazin-1-ylmethyl)phenyl)amino)pyrimido[4,5-d]pyridazin-5(6H)-one hydrochloride |

TABLE 1-continued
| Structure | IUPAC Name |
|---|---|
| 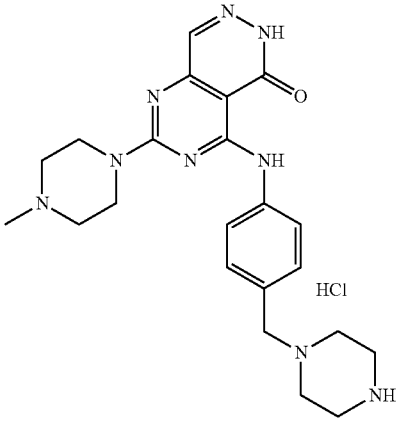 45 | 2-(4-methylpiperazin-1-yl)-4-((4-(piperazin-1-ylmethyl)phenyl)amino)pyrimido[4,5-d]pyridazin-5(6H)-one hydrochloride |
| 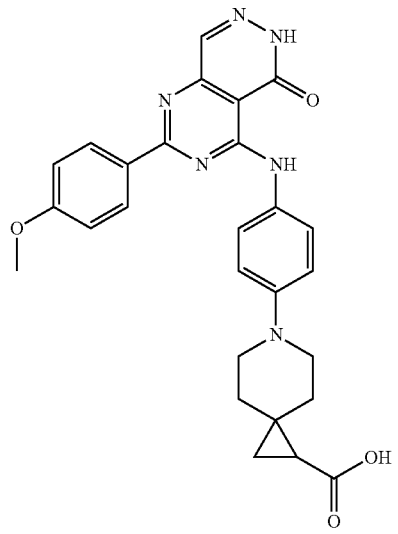 46 | 6-(4-((2-(4-methoxyphenyl)-5-oxo-5,6-dihydropyrimido[4,5-d]pyridazin-4-yl)amino)phenyl)-6-azaspiro[2.5]octane-1-carboxylic acid |
| 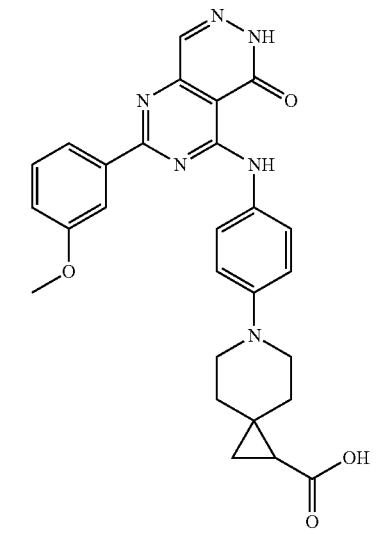 47 | 6-(4-((2-(3-methoxyphenyl)-5-oxo-5,6-dihydropyrimido[4,5-d]pyridazin-4-yl)amino)phenyl)-6-azaspiro[2.5]octane-1-carboxylic acid |

TABLE 1-continued
| Structure | IUPAC Name |
|---|---|
| 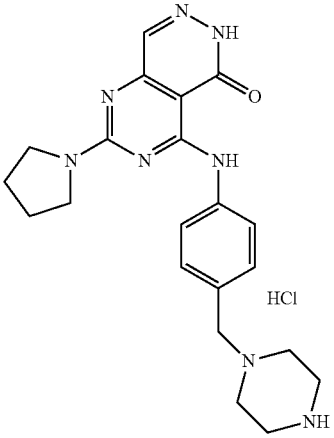 48 | 4-((4-(piperazin-1-ylmethyl)phenyl)amino)-2-(pyrrolidin-1-yl)pyrimido[4,5-d]pyridazin-5(6H)-one hydrochloride |
| 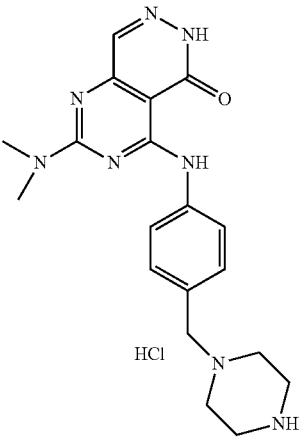 49 | 2-(dimethylamino)-4-((4-(piperazin-1-ylmethyl)phenyl)amino)pyrimido[4,5-d]pyridazin-5(6H)-one hydrochloride |
| 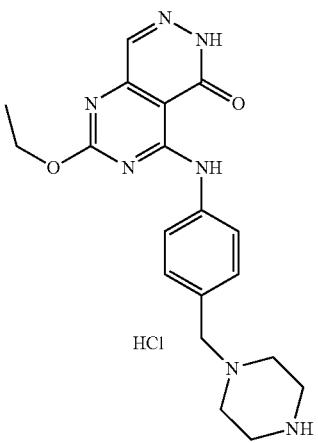 50 | 2-ethoxy-4-((4-(piperazin-1-ylmethyl)phenyl)amino)pyrimido[4,5-d]pyridazin-5(6H)-one hydrochloride |

TABLE 1-continued
| Structure | IUPAC Name |
|---|---|
| 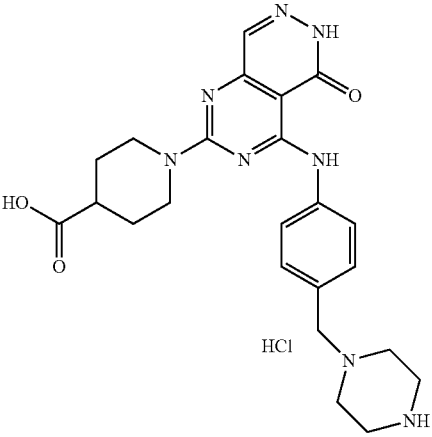 51 | 1-(5-oxo-4-((4-(piperazin-1-ylmethyl)phenyl)amino)-5,6-dihydropyrimido[4,5-d]pyridazin-2-yl)piperidine-4-carboxylic acid hydrochloride |
| 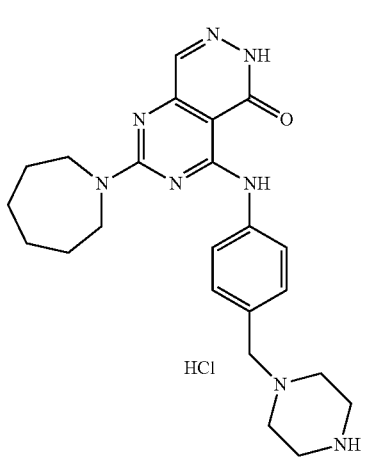 52 | 2-(azepan-1-yl)-4-((4-(piperazin-1-ylmethyl)phenyl)amino)pyrimido[4,5-d]pyridazin-5(6H)-one hydrochloride |
| 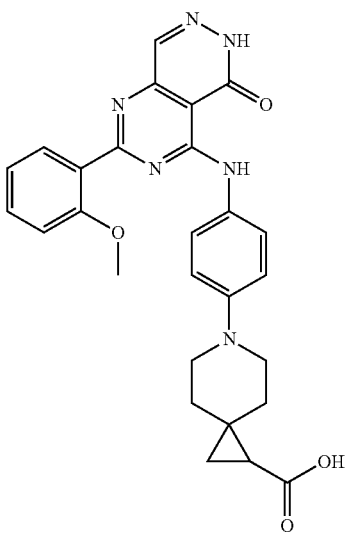 53 | 6-(4-((2-(2-methoxyphenyl)-5-oxo-5,6-dihydropyrimido[4,5-d]pyridazin-4-yl)amino)phenyl)-6-azaspiro[2.5]octane-1-carboxylic acid |

TABLE 1-continued

| Structure | IUPAC Name |
|---|---|
| 54 | 2-(diisopropylamino)-4-((4-(piperazin-1-ylmethyl)phenyl)amino)pyrimido[4,5-d]pyridazin-5(6H)-one hydrochloride |
| 55 | 2-(4-(morpholinomethyl)phenyl)-4-((4-(piperazin-1-ylmethyl)phenyl)amino)pyrimido[4,5-d]pyridazin-5(6H)-one hydrochloride |
| 56 | 1-(5-oxo-4-((4-(piperazin-1-ylmethyl)phenyl)amino)-5,6-dihydropyrimido[4,5-d]pyridazin-2-yl)piperidine-4-carbonitrile hydrochloride |

TABLE 1-continued
| Structure | IUPAC Name |
|---|---|
| 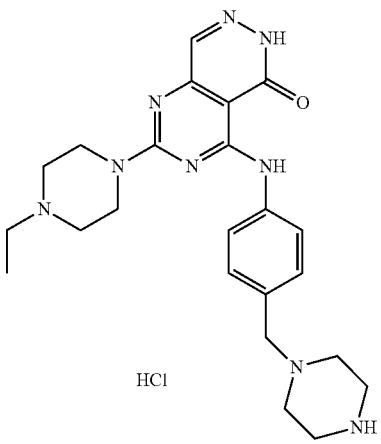<br>57 | 2-(4-ethylpiperazin-1-yl)-4-((4-(piperazin-1-ylmethyl)phenyl)amino)pyrimido[4,5-d]pyridazin-5(6H)-one hydrochloride |
| 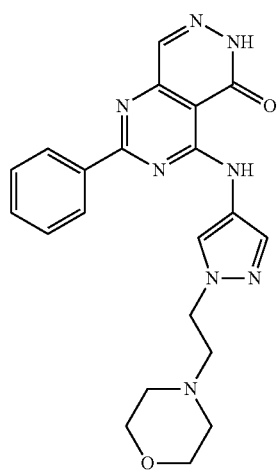<br>58 | 4-((1-(2-morpholinoethyl)-1H-pyrazol-4-yl)amino)-2-phenylpyrimido[4,5-d]pyridazin-5(6H)-one |
| 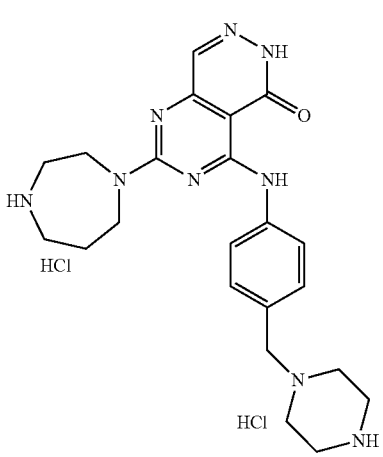<br>59 | 2-(1,4-diazepan-1-yl)-4-((4-(piperazin-1-ylmethyl)phenyl)amino)pyrimido[4,5-d]pyridazin-5(6H)-one dihydrochloride |

TABLE 1-continued
| Structure | IUPAC Name |
|---|---|
| 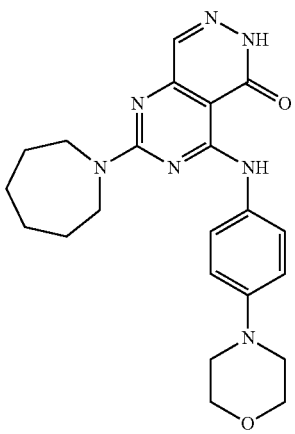 60 | 2-(azepan-1-yl)-4-((4-morpholinophenyl)amino)pyrimido[4,5-d]pyridazin-5(6H)-one |
| 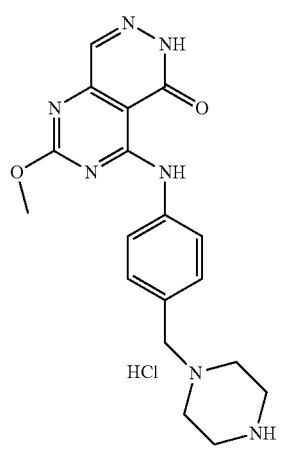 61 | 2-methoxy-4-((4-(piperazin-1-ylmethyl)phenyl)amino)pyrimido[4,5-d]pyridazin-5(6H)-one hydrochloride |
| 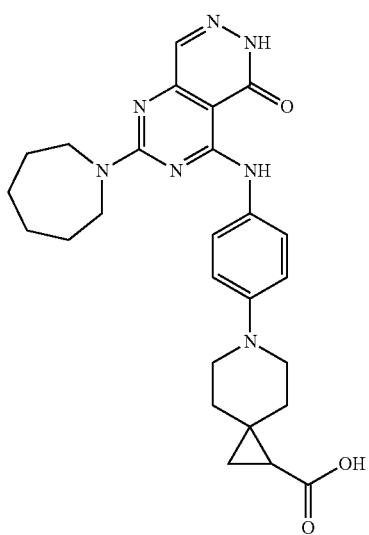 62 | 6-(4-((2-(azepan-1-yl)-5-oxo-5,6-dihydropyrimido[4,5-d]pyridazin-4-yl)amino)phenyl)-6-azaspiro[2.5]octane-1-carboxylic acid |

TABLE 1-continued
| Structure | IUPAC Name |
|---|---|
| 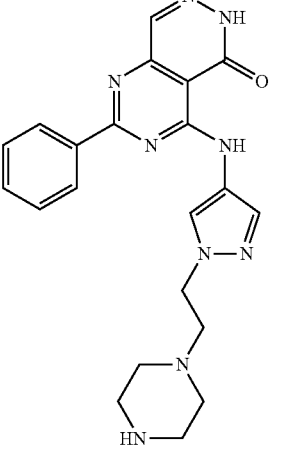 63 | 2-phenyl-4-((1-(2-(piperazin-1-yl)ethyl)-1H-pyrazol-4-yl)amino)pyrimido[4,5-d]pyridazin-5(6H)-one hydrochloride |
| 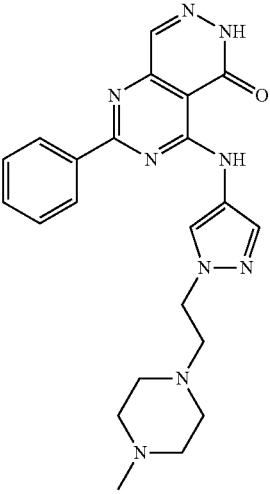 [SMILES: O=c1[nH]ncc2nc(-c3ccccc3)nc(Nc3cnn(CCN4CCOCC4)c3)c12] 64 | 4-((1-(2-(4-methylpiperazin-1-yl)ethyl)-1H-pyrazol-4-yl)amino)-2-phenylpyrimido[4,5-d]pyridazin-5(6H)-one |
| 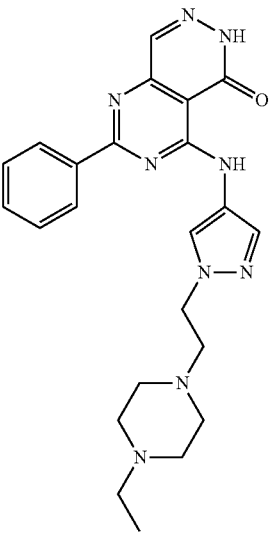 65 | 4-((1-(2-(4-ethylpiperazin-1-yl)ethyl)-1H-pyrazol-4-yl)amino)-2-phenylpyrimido[4,5-d]pyridazin-5(6H)-one |

TABLE 1-continued
| Structure | IUPAC Name |
|---|---|
| 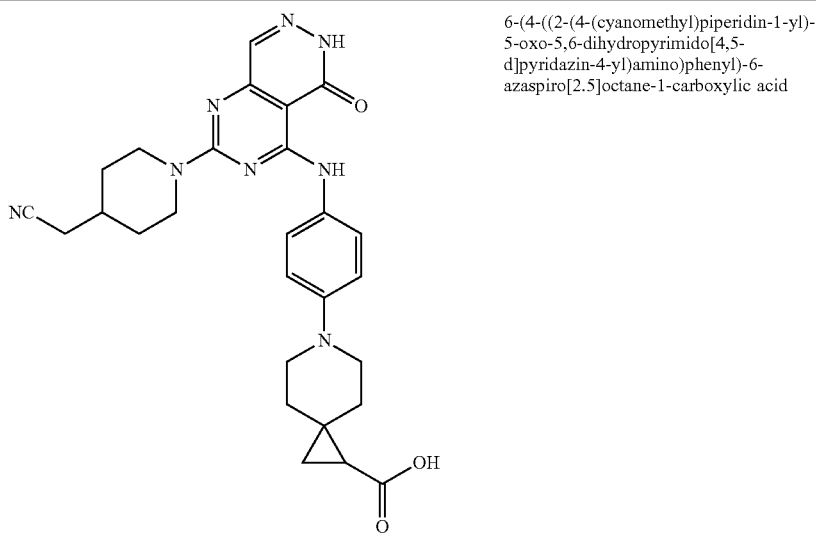 66 | 6-(4-((2-(4-(cyanomethyl)piperidin-1-yl)-5-oxo-5,6-dihydropyrimido[4,5-d]pyridazin-4-yl)amino)phenyl)-6-azaspiro[2.5]octane-1-carboxylic acid |
| 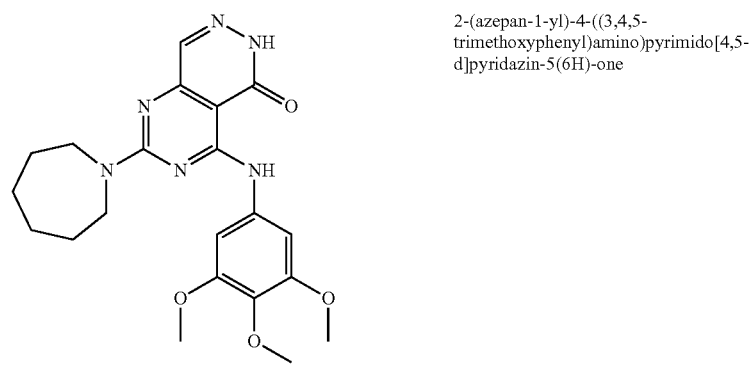 67 | 2-(azepan-1-yl)-4-((3,4,5-trimethoxyphenyl)amino)pyrimido[4,5-d]pyridazin-5(6H)-one |
| 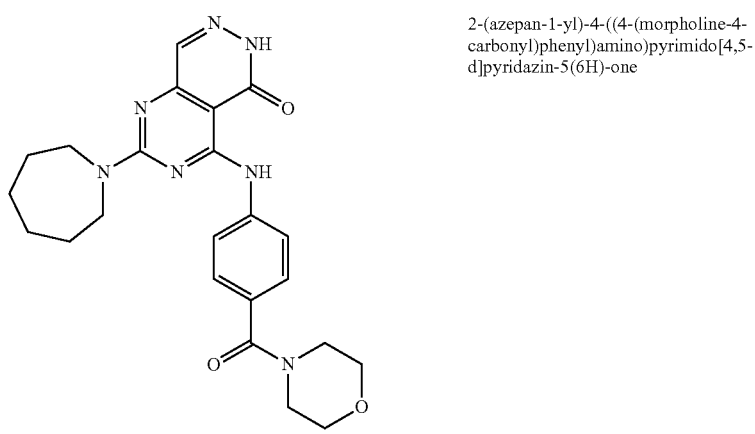 68 | 2-(azepan-1-yl)-4-((4-(morpholine-4-carbonyl)phenyl)amino)pyrimido[4,5-d]pyridazin-5(6H)-one |

TABLE 1-continued
| Structure | IUPAC Name |
|---|---|
| 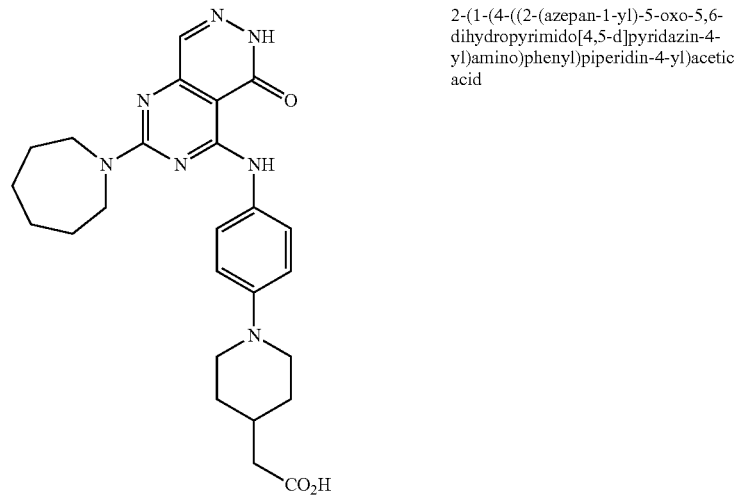 69 | 2-(1-(4-((2-(azepan-1-yl)-5-oxo-5,6-dihydropyrimido[4,5-d]pyridazin-4-yl)amino)phenyl)piperidin-4-yl)acetic acid |
| 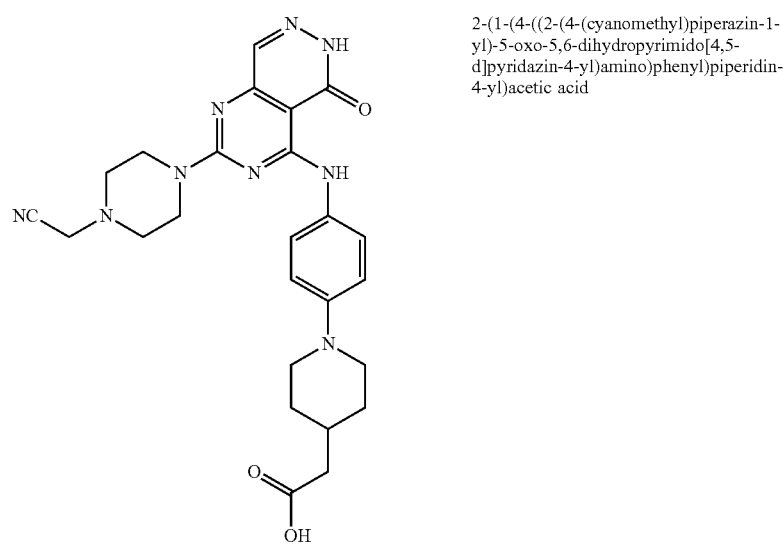 70 | 2-(1-(4-((2-(4-(cyanomethyl)piperazin-1-yl)-5-oxo-5,6-dihydropyrimido[4,5-d]pyridazin-4-yl)amino)phenyl)piperidin-4-yl)acetic acid |

TABLE 1-continued
| Structure | IUPAC Name |
|---|---|
| 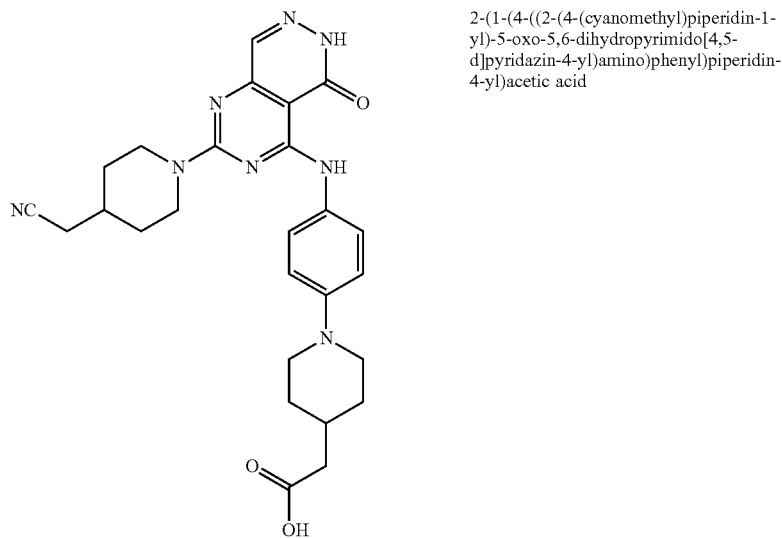 71 | 2-(1-(4-((2-(4-(cyanomethyl)piperidin-1-yl)-5-oxo-5,6-dihydropyrimido[4,5-d]pyridazin-4-yl)amino)phenyl)piperidin-4-yl)acetic acid |
| 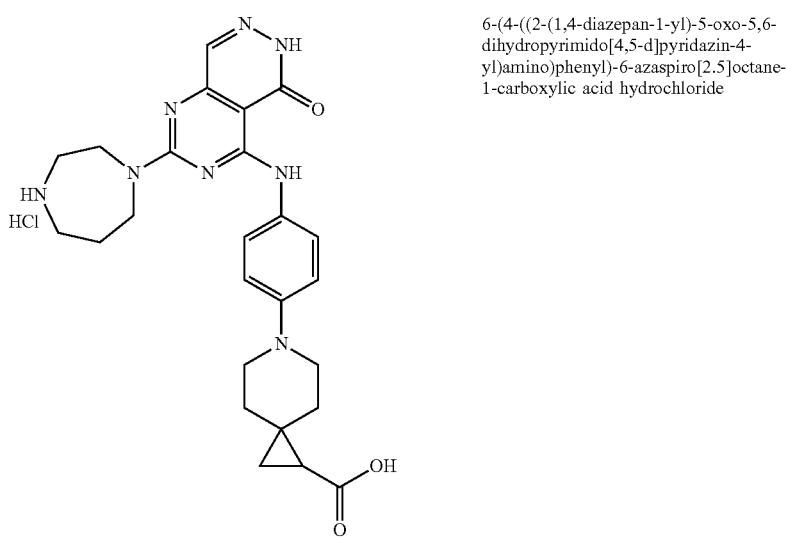 72 | 6-(4-((2-(1,4-diazepan-1-yl)-5-oxo-5,6-dihydropyrimido[4,5-d]pyridazin-4-yl)amino)phenyl)-6-azaspiro[2.5]octane-1-carboxylic acid hydrochloride |

TABLE 1-continued
| Structure | IUPAC Name |
|---|---|
| 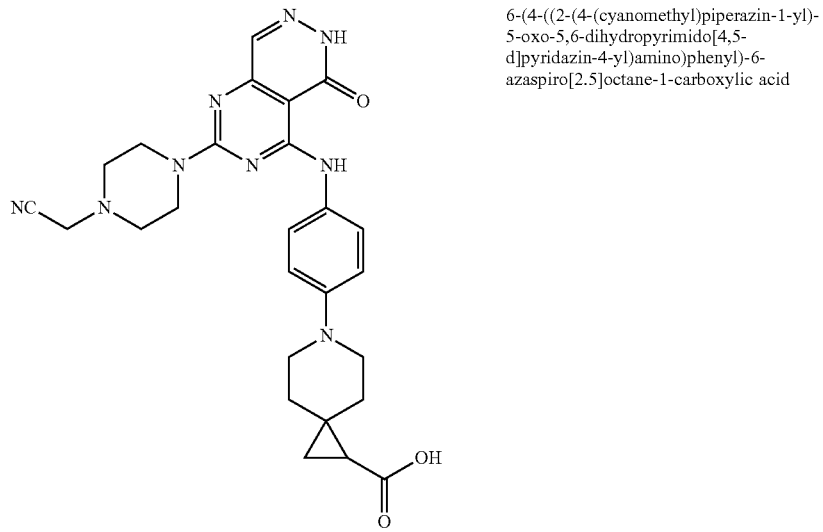 73 | 6-(4-((2-(4-(cyanomethyl)piperazin-1-yl)-5-oxo-5,6-dihydropyrimido[4,5-d]pyridazin-4-yl)amino)phenyl)-6-azaspiro[2.5]octane-1-carboxylic acid |
| 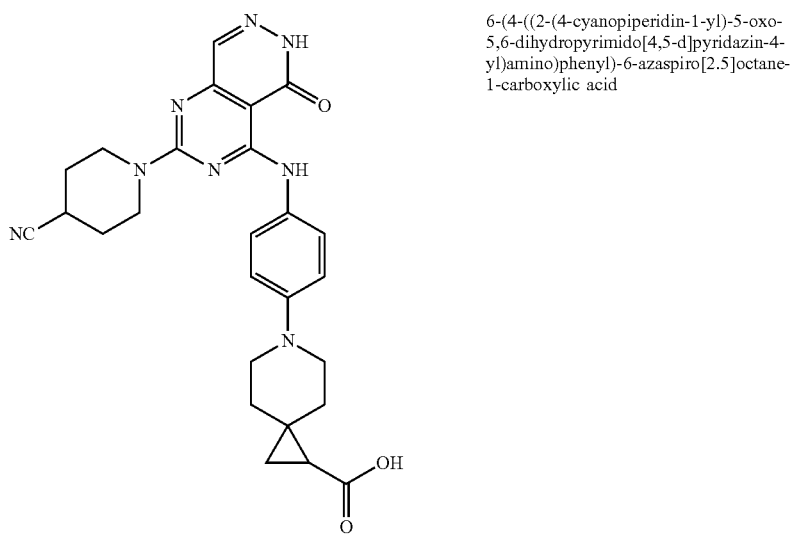 74 | 6-(4-((2-(4-cyanopiperidin-1-yl)-5-oxo-5,6-dihydropyrimido[4,5-d]pyridazin-4-yl)amino)phenyl)-6-azaspiro[2.5]octane-1-carboxylic acid |

TABLE 1-continued
| Structure | IUPAC Name |
|---|---|
| 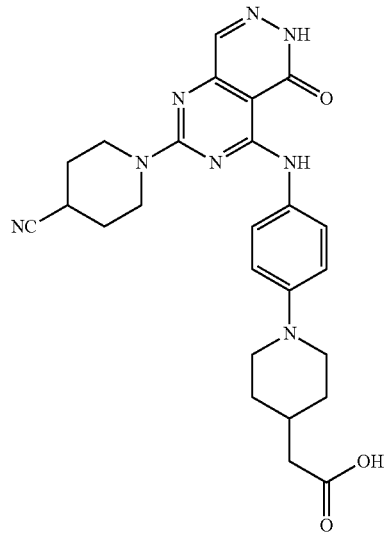 75 | 2-(1-(4-((2-(4-cyanopiperidin-1-yl)-5-oxo-5,6-dihydropyrimido[4,5-d]pyridazin-4-yl)amino)phenyl)piperidin-4-yl)acetic acid |
| 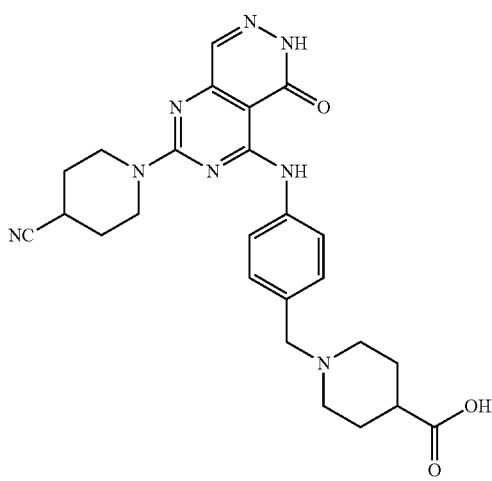 76 | 1-(4-((2-(4-cyanopiperidin-1-yl)-5-oxo-5,6-dihydropyrimido[4,5-d]pyridazin-4-yl)amino)benzyl)piperidine-4-carboxylic acid |
| 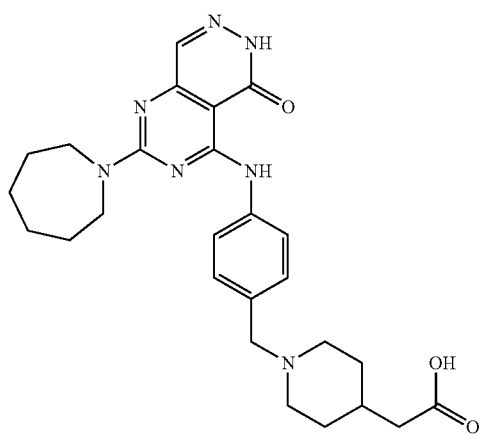 77 | 2-(1-(4-((2-(azepan-1-yl)-5-oxo-5,6-dihydropyrimido[4,5-d]pyridazin-4-yl)amino)benzyl)piperidin-4-yl)acetic acid |

TABLE 1-continued
| Structure | IUPAC Name |
|---|---|
| 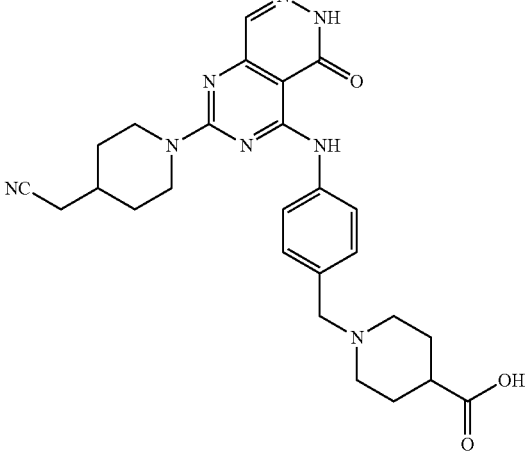 78 | 1-(4-((2-(4-(cyanomethyl)piperidin-1-yl)-5-oxo-5,6-dihydropyrimido[4,5-d]pyridazin-4-yl)amino)benzyl)piperidine-4-carboxylic acid |
| 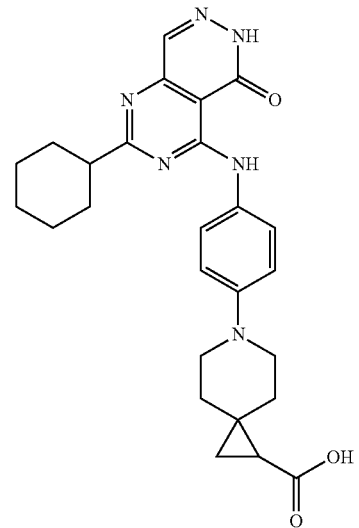 79 | 6-(4-((2-cyclohexyl-5-oxo-5,6-dihydropyrimido[4,5-d]pyridazin-4-yl)amino)phenyl)-6-azaspiro[2.5]octane-1-carboxylic acid |
| 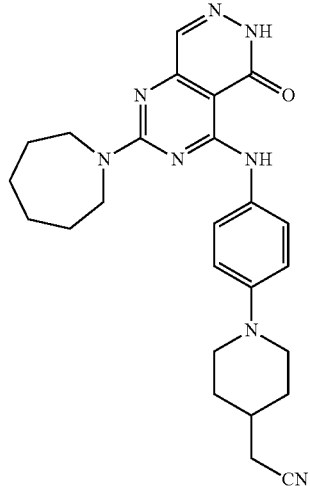 80 | 2-(1-(4-((2-(azepan-1-yl)-5-oxo-5,6-dihydropyrimido[4,5-d]pyridazin-4-yl)amino)phenyl)piperidin-4-yl)acetonitrile |

TABLE 1-continued
| Structure | IUPAC Name |
|---|---|
| 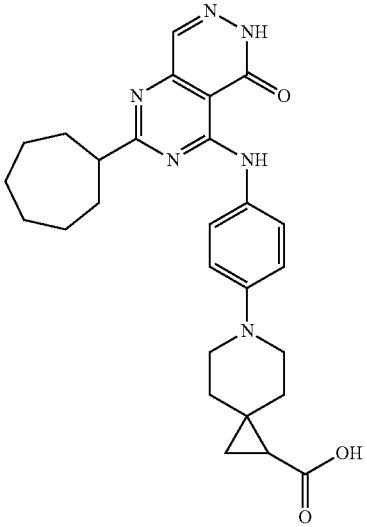 81 | 6-(4-((2-cycloheptyl-5-oxo-5,6-dihydropyrimido[4,5-d]pyridazin-4-yl)amino)phenyl)-6-azaspiro[2.5]octane-1-carboxylic acid |
| 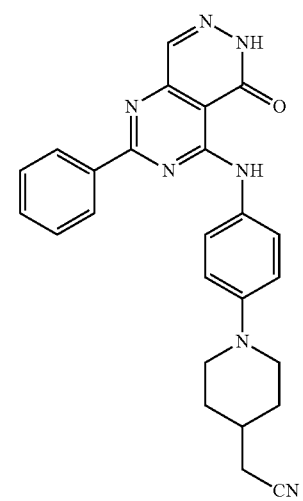 82 | 2-(1-(4-((5-oxo-2-phenyl-5,6-dihydropyrimido[4,5-d]pyridazin-4-yl)amino)phenyl)piperidin-4-yl)acetonitrile |
| 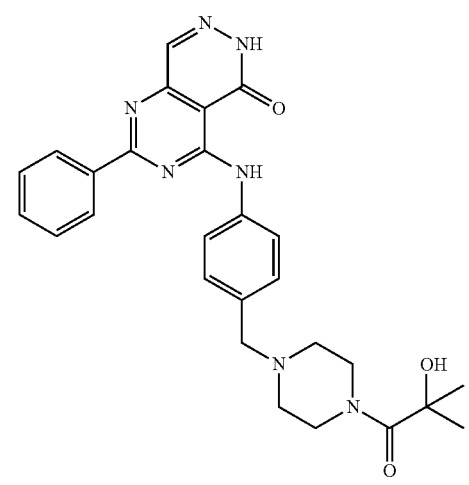 83 | 4-((4-((4-(2-hydroxy-2-methylpropanoyl)piperazin-1-yl)methyl)phenyl)amino)-2-phenylpyrimido[4,5-d]pyridazin-5(6H)-one |

TABLE 1-continued
| Structure | IUPAC Name |
|---|---|
| 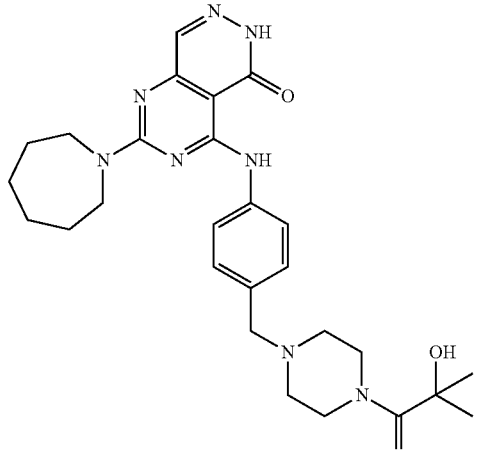 84 | 2-(azepan-1-yl)-4-((4-((4-(2-hydroxy-2-methylpropanoyl)piperazin-1-yl)methyl)phenyl)amino)pyrimido[4,5-d]pyridazin-5(6H)-one |
| 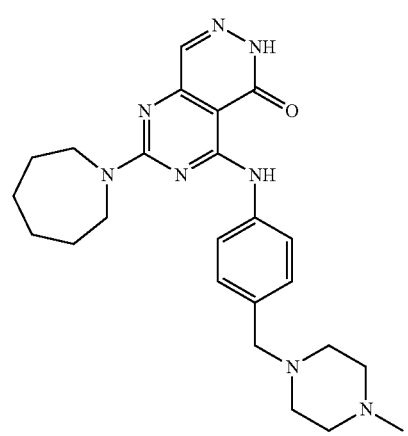 85 | 2-(azepan-1-yl)-4-((4-((4-methylpiperazin-1-yl)methyl)phenyl)amino)pyrimido[4,5-d]pyridazin-5(6H)-one |
| 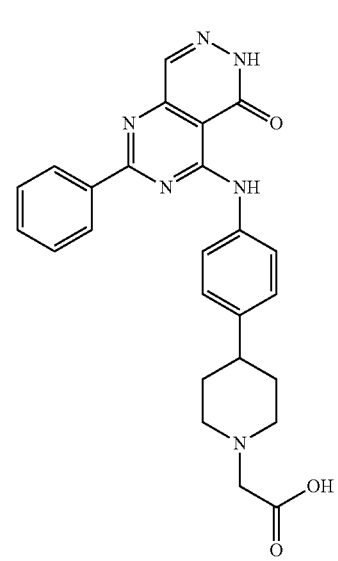 86 | 2-(4-(4-((5-oxo-2-phenyl-5,6-dihydropyrimido[4,5-d]pyridazin-4-yl)amino)phenyl)piperidin-1-yl)acetic acid |

TABLE 1-continued
| Structure | IUPAC Name |
|---|---|
| 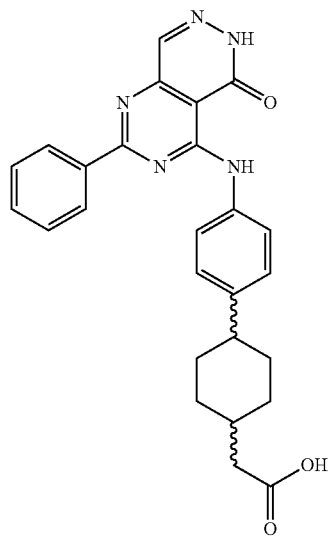 87 | 2-(4-(4-((5-oxo-2-phenyl-5,6-dihydropyrimido[4,5-d]pyridazin-4-yl)amino)phenyl)cyclohexyl)acetic acid |
| 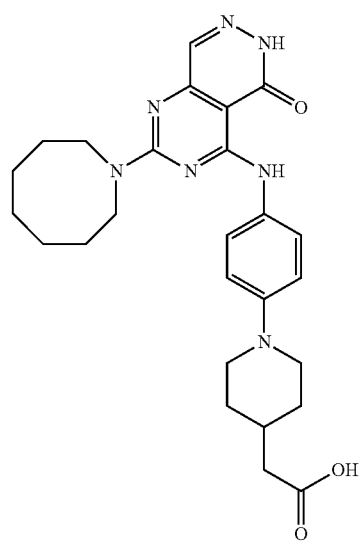 88 | 2-(1-(4-((2-(azocan-1-yl)-5-oxo-5,6-dihydropyrimido[4,5-d]pyridazin-4-yl)amino)phenyl)piperidin-4-yl)acetic acid |

TABLE 1-continued
| Structure | IUPAC Name |
|---|---|
| 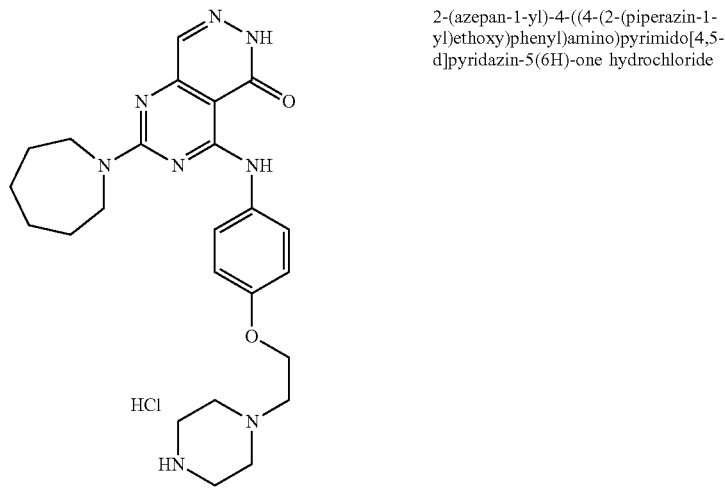 89 | 2-(azepan-1-yl)-4-((4-(2-(piperazin-1-yl)ethoxy)phenyl)amino)pyrimido[4,5-d]pyridazin-5(6H)-one hydrochloride |
| 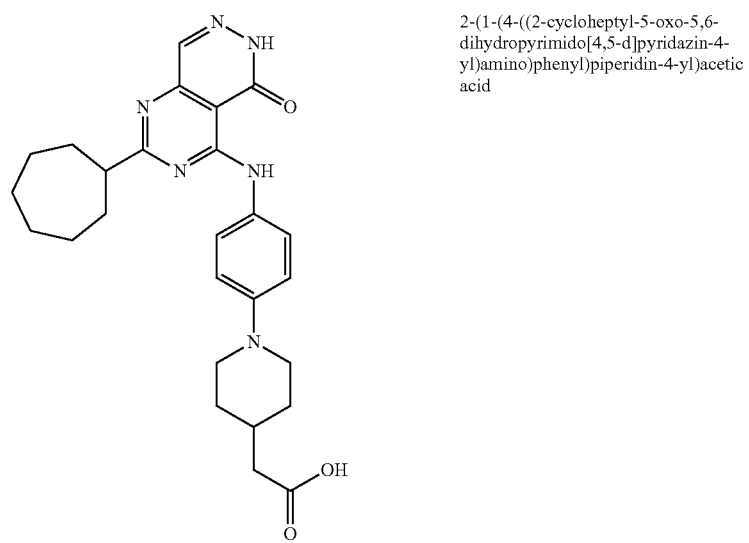 90 | 2-(1-(4-((2-cycloheptyl-5-oxo-5,6-dihydropyrimido[4,5-d]pyridazin-4-yl)amino)phenyl)piperidin-4-yl)acetic acid |

TABLE 1-continued

| Structure | IUPAC Name |
| --- | --- |
| 91 | 2-(4-(4-((2-(azepan-1-yl)-5-oxo-5,6-dihydropyrimido[4,5-d]pyridazin-4-yl)amino)phenyl)cyclohexyl)acetic acid |
| 92 | 4-(4-((2-(azepan-1-yl)-5-oxo-5,6-dihydropyrimido[4,5-d]pyridazin-4-yl)amino)phenoxy)butanoic acid |
| 93 | 2-(azepan-1-yl)-4-((4-(2-morpholinoethoxy)phenyl)amino)pyrimido[4,5-d]pyridazin-5(6H)-one |

TABLE 1-continued
| Structure | IUPAC Name |
|---|---|
| 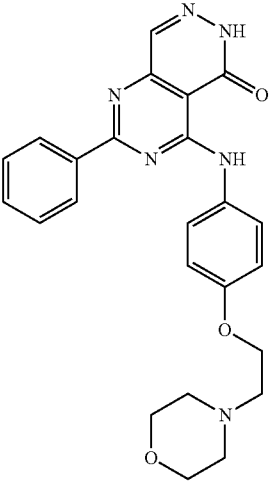 94 | 4-((4-(2-morpholinoethoxy)phenyl)amino)-2-phenylpyrimido[4,5-d]pyridazin-5(6H)-one |
| 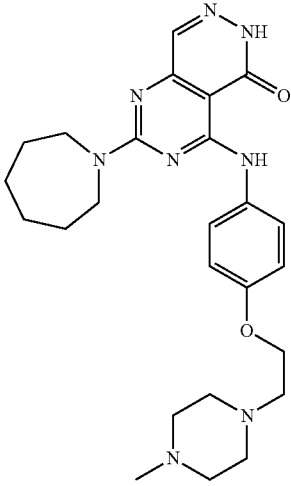 95 | 2-(azepan-1-yl)-4-((4-(2-(4-methylpiperazin-1-yl)ethoxy)phenyl)amino)pyrimido[4,5-d]pyridazin-5(6H)-one |
| 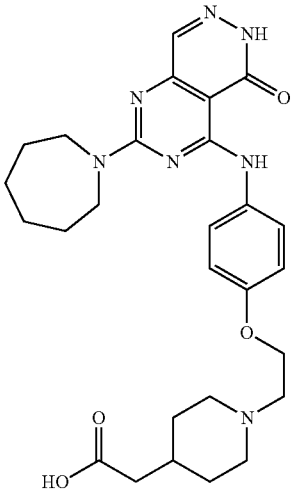 96 | 2-(1-(2-(4-((2-(azepan-1-yl)-5-oxo-5,6-dihydropyrimido[4,5-d]pyridazin-4-yl)amino)phenoxy)ethyl)piperidin-4-yl)acetic acid |

TABLE 1-continued
| Structure | IUPAC Name |
|---|---|
| 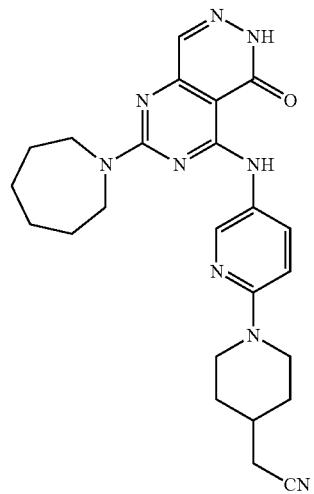<br>97 | 2-(1-(5-((2-(azepan-1-yl)-5-oxo-5,6-dihydropyrimido[4,5-d]pyridazin-4-yl)amino)pyridin-2-yl)piperidin-4-yl)acetonitrile |
| 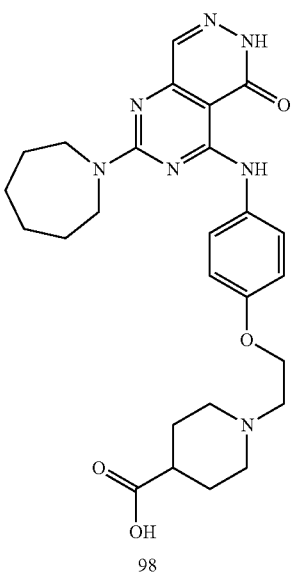 [SMILES: O=C(O)C1CCN(CCOc2ccc(Nc3nc(N4CCCCCC4)nc4cn[nH]c(=O)c34)cc2)CC1]<br>98 | 1-(2-(4-((2-(azepan-1-yl)-5-oxo-5,6-dihydropyrimido[4,5-d]pyridazin-4-yl)amino)phenoxy)ethyl)piperidine-4-carboxylic acid |

TABLE 1-continued
| Structure | IUPAC Name |
|---|---|
| 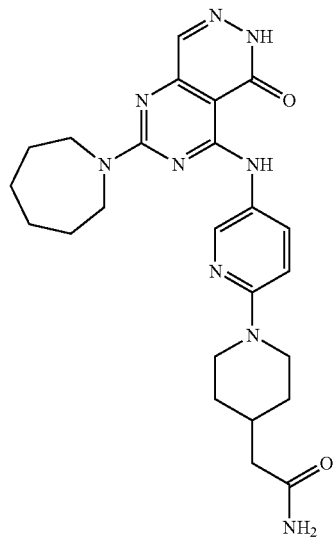 99 | 2-(1-(5-((2-(azepan-1-yl)-5-oxo-5,6 dihydropyrimido[4,5-d]pyridazin-4-yl)amino)pyridin-2-yl)piperidin-4-yl)acetamide |
| 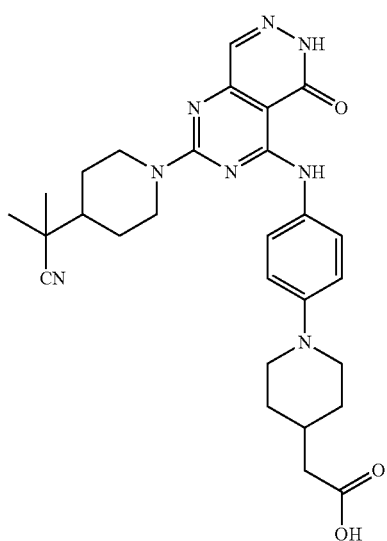 100 | 2-(1-(4-((2-(4-(2-cyanopropan-2-yl)piperidin-1-yl)-5-oxo-5,6-dihydropyrimido[4,5-d]pyridazin-4-yl)amino)phenyl)piperidin-4-yl)acetic acid |

TABLE 1-continued
| Structure | IUPAC Name |
|---|---|
| 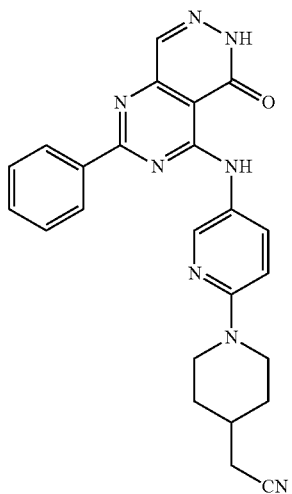 101 | 2-(1-(5-((5-oxo-2-phenyl-5,6-dihydropyrimido[4,5-d]pyridazin-4-yl)amino)pyridin-2-yl)piperidin-4-yl)acetonitrile |
| 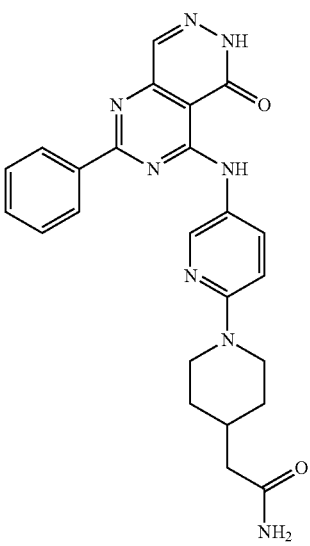 102 | 2-(1-(5-((5-oxo-2-phenyl-5,6-dihydropyrimido[4,5-d]pyridazin-4-yl)amino)pyridin-2-yl)piperidin-4-yl)acetamide |

TABLE 1-continued
| Structure | IUPAC Name |
|---|---|
| 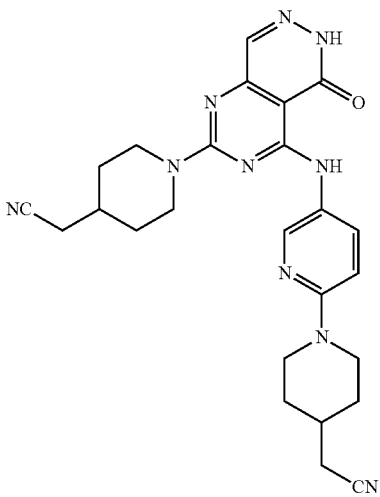 103 | 2-(1-(5-((2-(4-(cyanomethyl)piperidin-1-yl)-5-oxo-5,6-dihydropyrimido[4,5-d]pyridazin-4-yl)amino)pyridin-2-yl)piperidin-4-yl)acetonitrile |
| 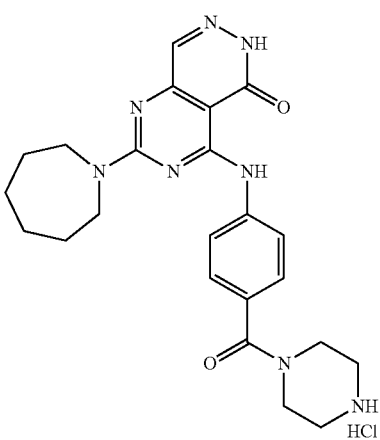 104 | 2-(azepan-1-yl)-4-((4-(piperazine-1-carbonyl)phenyl)amino)pyrimido[4,5-d]pyridazin-5(6H)-one hydrochloride |
| 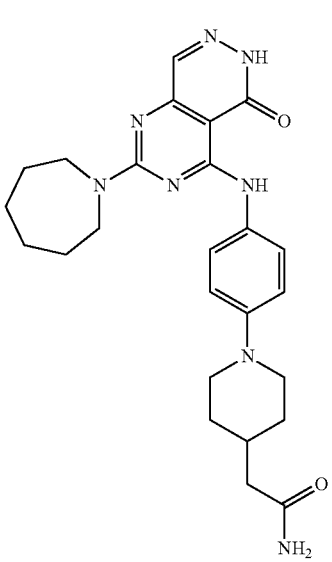 105 | 2-(1-(4-((2-(azepan-1-yl)-5-oxo-5,6-dihydropyrimido[4,5-d]pyridazin-4-yl)amino)phenyl)piperidin-4-yl)acetamide |

TABLE 1-continued
| Structure | IUPAC Name |
|---|---|
| 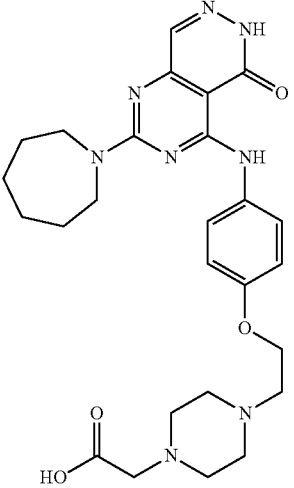 106 | 2-(4-(2-(4-((2-(azepan-1-yl)-5-oxo-5,6-dihydropyrimido[4,5-d]pyridazin-4-yl)amino)phenoxy)ethyl)piperazin-1-yl)acetic acid |
| 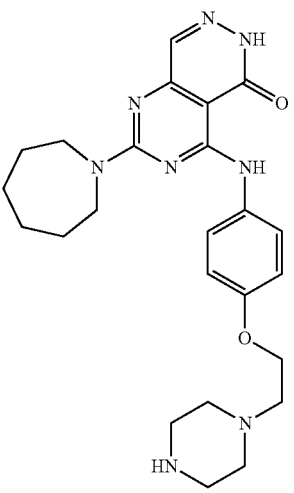 107 | 2-(azepan-1-yl)-4-((4-(2-(piperazin-1-yl)ethoxy)phenyl)amino)pyrimido[4,5-d]pyridazin-5(6H)-one |
| 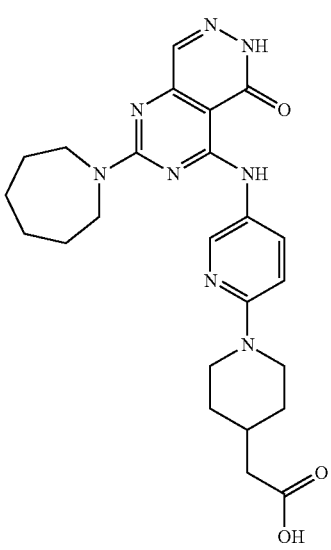 108 | 2-(1-(5-((2-(azepan-1-yl)-5-oxo-5,6-dihydropyrimido[4,5-d]pyridazin-4-yl)amino)pyridin-2-yl)piperidin-4-yl)acetic acid |

TABLE 1-continued
| Structure | IUPAC Name |
|---|---|
| 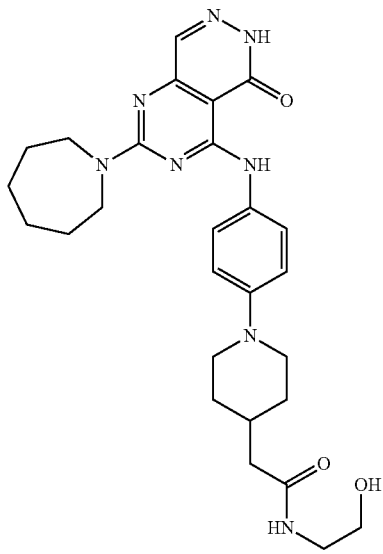<br>109 | 2-(1-(4-((2-(azepan-1-yl)-5-oxo-5,6-dihydropyrimido[4,5-d]pyridazin-4-yl)amino)phenyl)piperidin-4-yl)-N-(2-hydroxyethyl)acetamide |
| 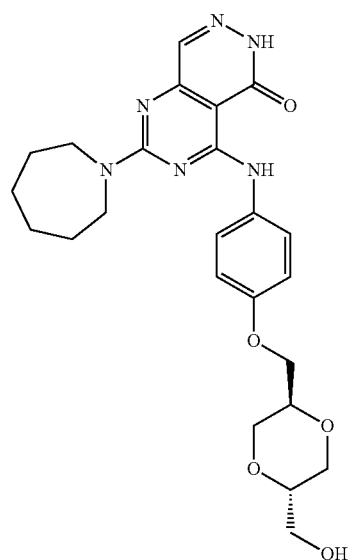<br>110 | 2-(azepan-1-yl)-4-((4-(((2S,5S)-5-(hydroxymethyl)-1,4-dioxan-2-yl)methoxy)phenyl)amino)pyrimido[4,5-d]pyridazin-5(6H)-one |

TABLE 1-continued
| Structure | IUPAC Name |
|---|---|
| 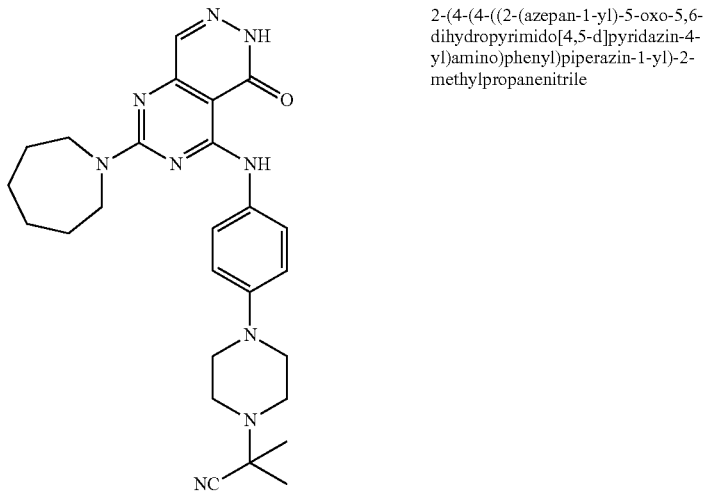 111 | 2-(4-(4-((2-(azepan-1-yl)-5-oxo-5,6-dihydropyrimido[4,5-d]pyridazin-4-yl)amino)phenyl)piperazin-1-yl)-2-methylpropanenitrile |
| 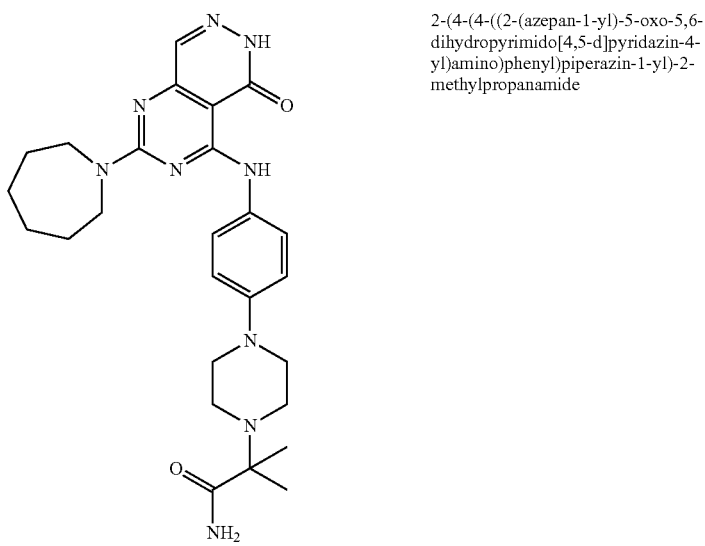 112 | 2-(4-(4-((2-(azepan-1-yl)-5-oxo-5,6-dihydropyrimido[4,5-d]pyridazin-4-yl)amino)phenyl)piperazin-1-yl)-2-methylpropanamide |

TABLE 1-continued
| Structure | IUPAC Name |
|---|---|
| 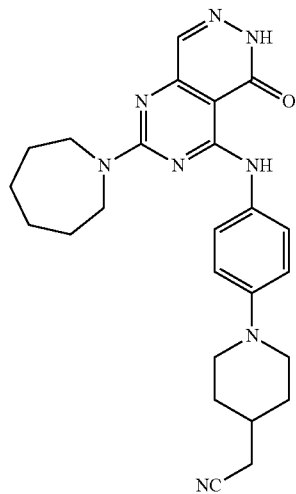<br>113 | 2-(1-(4-((2-(azepan-1-yl)-5-oxo-5,6-dihydropyrimido[4,5-d]pyridazin-4-yl)amino)phenyl)piperidin-4-yl)acetonitrile |
| 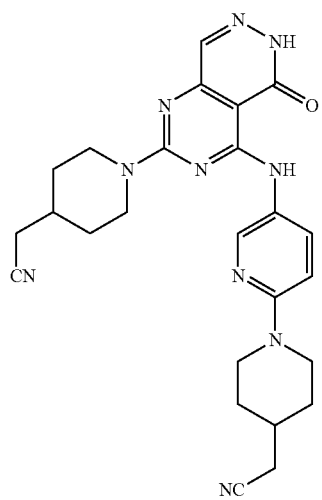<br>114 | 2-(1-(5-((2-(4-(cyanomethyl)piperidin-1-yl)-5-oxo-5,6-dihydropyrimido[4,5-d]pyridazin-4-yl)amino)pyridin-2-yl)piperidin-4-yl)acetonitrile |

TABLE 1-continued
| Structure | IUPAC Name |
|---|---|
| 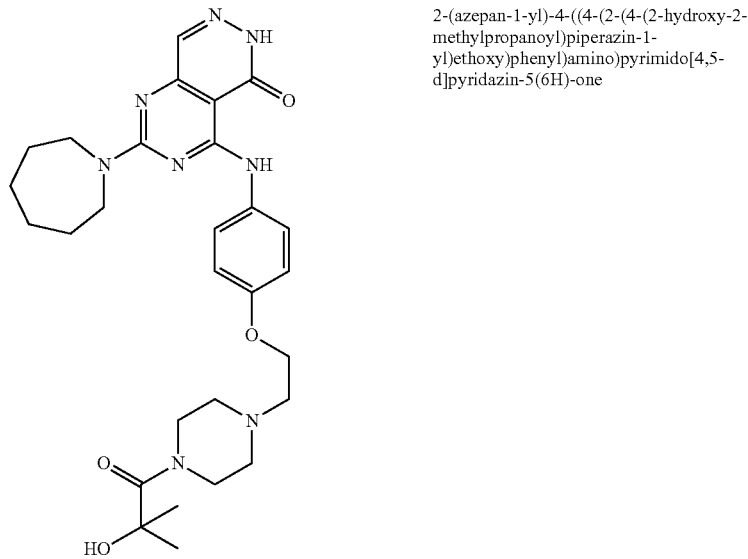 115 | 2-(azepan-1-yl)-4-((4-(2-(4-(2-hydroxy-2-methylpropanoyl)piperazin-1-yl)ethoxy)phenyl)amino)pyrimido[4,5-d]pyridazin-5(6H)-one |
| 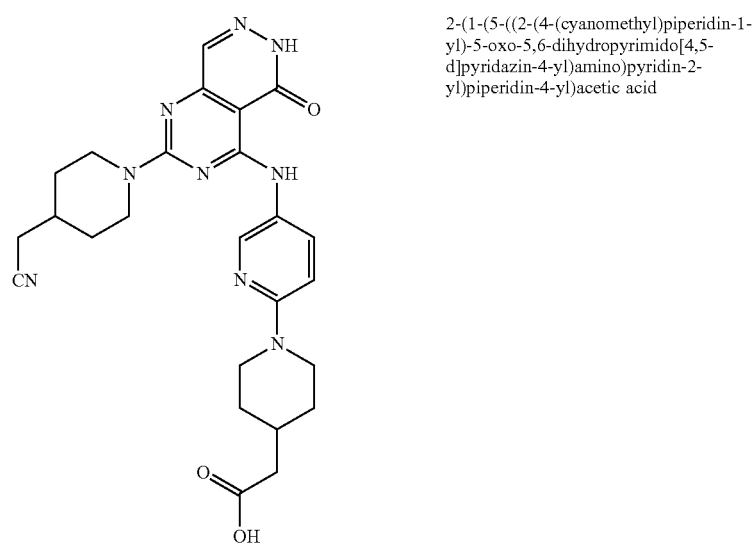 116 | 2-(1-(5-((2-(4-(cyanomethyl)piperidin-1-yl)-5-oxo-5,6-dihydropyrimido[4,5-d]pyridazin-4-yl)amino)pyridin-2-yl)piperidin-4-yl)acetic acid |

TABLE 1-continued
| Structure | IUPAC Name |
|---|---|
| 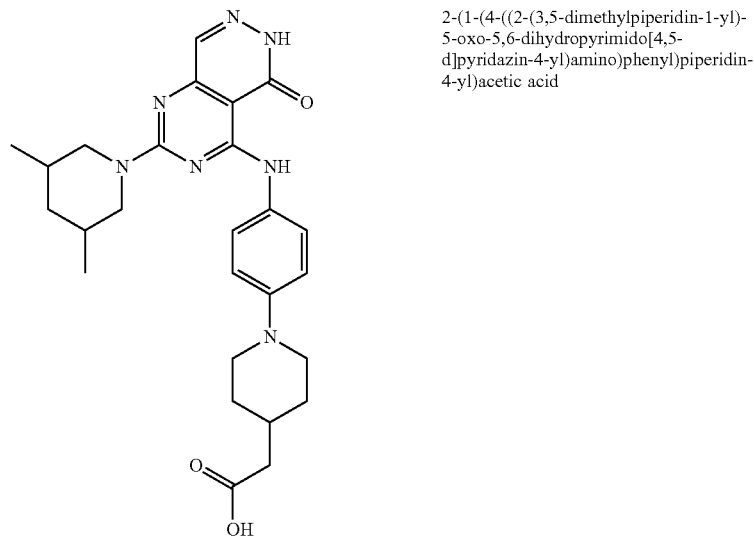 117 | 2-(1-(4-((2-(3,5-dimethylpiperidin-1-yl)-5-oxo-5,6-dihydropyrimido[4,5-d]pyridazin-4-yl)amino)phenyl)piperidin-4-yl)acetic acid |
| 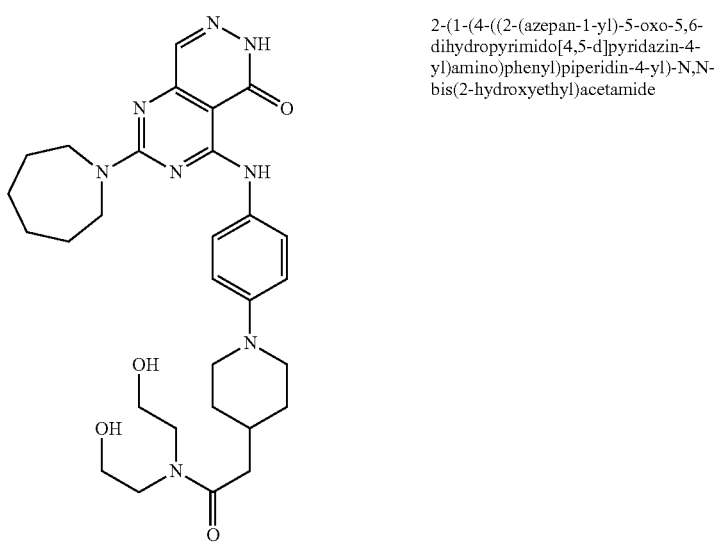 118 | 2-(1-(4-((2-(azepan-1-yl)-5-oxo-5,6-dihydropyrimido[4,5-d]pyridazin-4-yl)amino)phenyl)piperidin-4-yl)-N,N-bis(2-hydroxyethyl)acetamide |

TABLE 1-continued
| Structure | IUPAC Name |
|---|---|
| 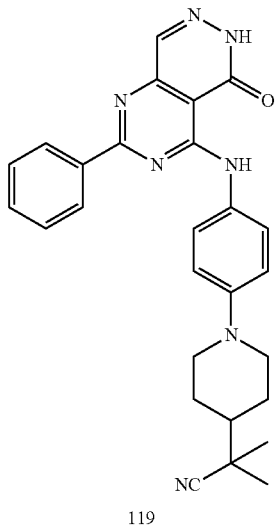 [SMILES: CC(C)(C#N)C1CCN(c2ccc(Nc3nc(-c4ccccc4)nc4cn[nH]c(=O)c34)cc2)CC1] 119 | 2-methyl-2-(1-(4-((5-oxo-2-phenyl-5,6-dihydropyrimido[4,5-d]pyridazin-4-yl)amino)phenyl)piperidin-4-yl)propanenitrile |
| 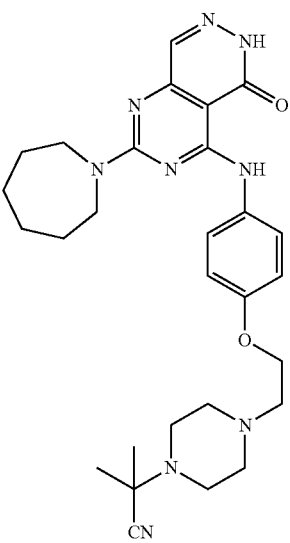 120 | 2-(4-(2-(4-((2-(azepan-1-yl)-5-oxo-5,6-dihydropyrimido[4,5-d]pyridazin-4-yl)amino)phenoxy)ethyl)piperazin-1-yl)-2-methylpropanenitrile |

TABLE 1-continued
| Structure | IUPAC Name |
|---|---|
| 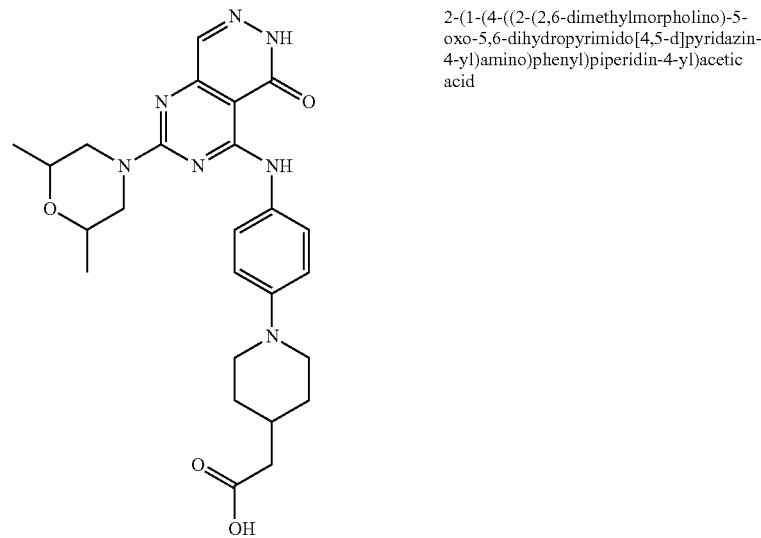 121 | 2-(1-(4-((2-(2,6-dimethylmorpholino)-5-oxo-5,6-dihydropyrimido[4,5-d]pyridazin-4-yl)amino)phenyl)piperidin-4-yl)acetic acid |
| 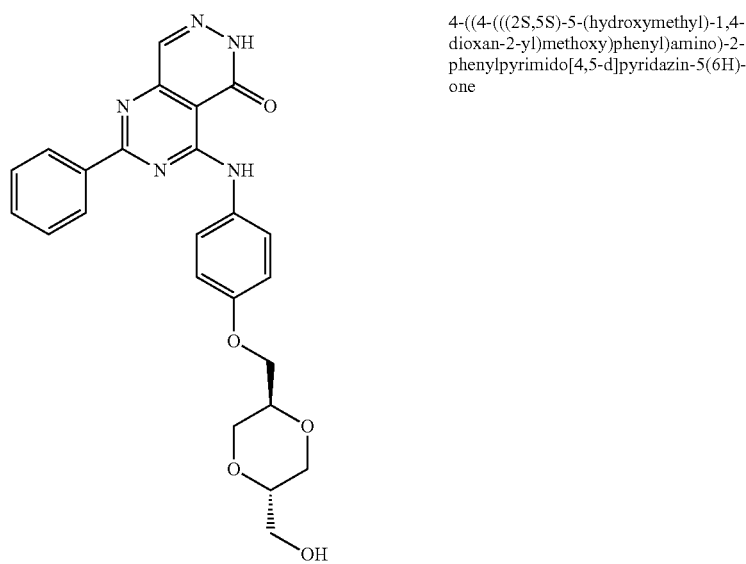 122 | 4-((4-(((2S,5S)-5-(hydroxymethyl)-1,4-dioxan-2-yl)methoxy)phenyl)amino)-2-phenylpyrimido[4,5-d]pyridazin-5(6H)-one |

TABLE 1-continued
| Structure | IUPAC Name |
|---|---|
| 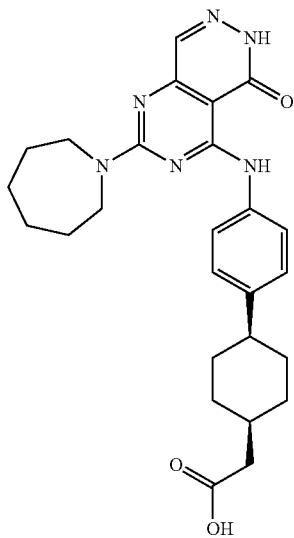<br>123 | 2-((1S,4S)-4-(4-((2-(azepan-1-yl)-5-oxo-5,6-dihydropyrimido[4,5-d]pyridazin-4-yl)amino)phenyl)cyclohexyl)acetic acid |
| 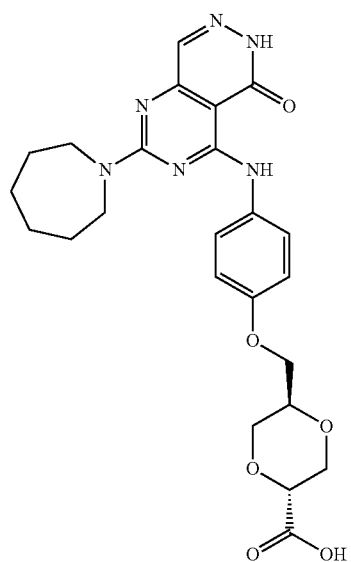<br>124 | (2R,5S)-5-((4-((2-(azepan-1-yl)-5-oxo-5,6-dihydropyrimido[4,5-d]pyridazin-4-yl)amino)phenoxy)methyl)-1,4-dioxane-2-carboxylic acid |

TABLE 1-continued
| Structure | IUPAC Name |
|---|---|
| 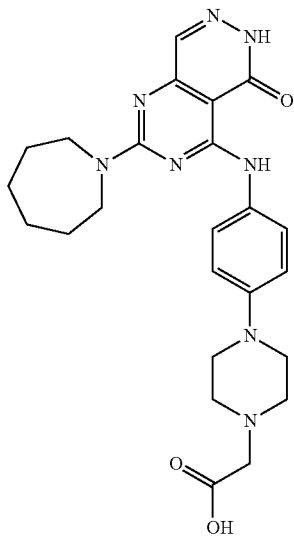<br>125 | 2-(4-(4-((2-(azepan-1-yl)-5-oxo-5,6-dihydropyrimido[4,5-d]pyridazin-4-yl)amino)phenyl)piperazin-1-yl)acetic acid |
| 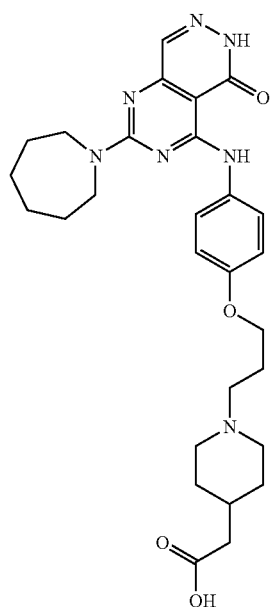<br>126 | 2-(1-(3-(4-((2-(azepan-1-yl)-5-oxo-5,6-dihydropyrimido[4,5-d]pyridazin-4-yl)amino)phenoxy)propyl)piperidin-4-yl)acetic acid |

TABLE 1-continued
| Structure | IUPAC Name |
|---|---|
| 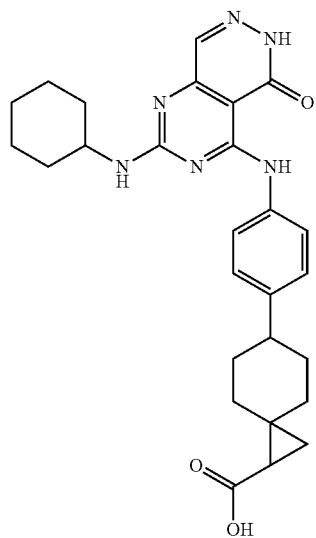 127 | 6-(4-((2-(cyclohexylamino)-5-oxo-5,6-dihydropyrimido[4,5-d]pyridazin-4-yl)amino)phenyl)spiro[2.5]octane-1-carboxylic acid |
| 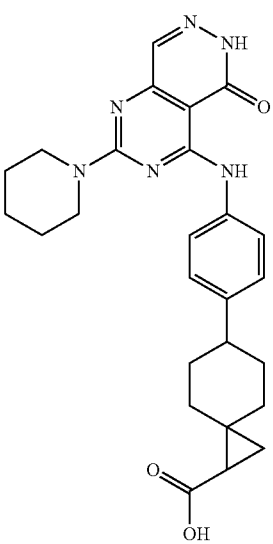 128 | 6-(4-((5-oxo-2-(piperidin-1-yl)-5,6-dihydropyrimido[4,5-d]pyridazin-4-yl)amino)phenyl)spiro[2.5]octane-1-carboxylic acid |

TABLE 1-continued
| Structure | IUPAC Name |
|---|---|
| 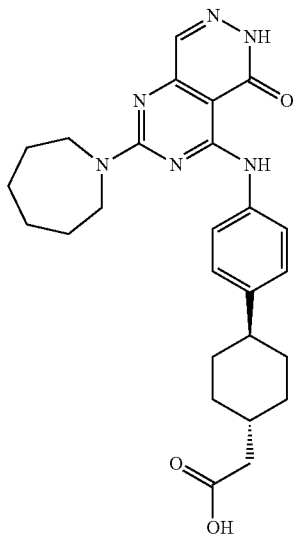 129 | 2-((1R,4R)-4-(4-((2-(azepan-1-yl)-5-oxo-5,6-dihydropyrimido[4,5-d]pyridazin-4-yl)amino)phenyl)cyclohexyl)acetic acid |
| 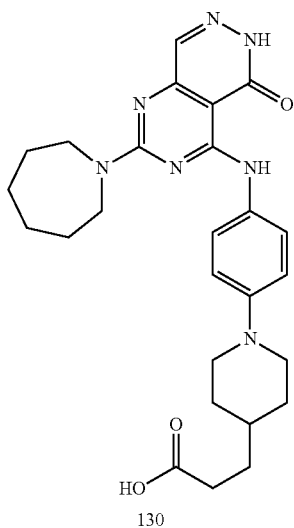 [SMILES: O=C(O)CCC1CCN(c2ccc(Nc3nc(N4CCCCCC4)nc4cn[nH]c(=O)c34)cc2)CC1] 130 | 3-(1-(4-((2-(azepan-1-yl)-5-oxo-5,6-dihydropyrimido[4,5-d]pyridazin-4-yl)amino)phenyl)piperidin-4-yl)propanoic acid |

TABLE 1-continued
| Structure | IUPAC Name |
| --- | --- |
| 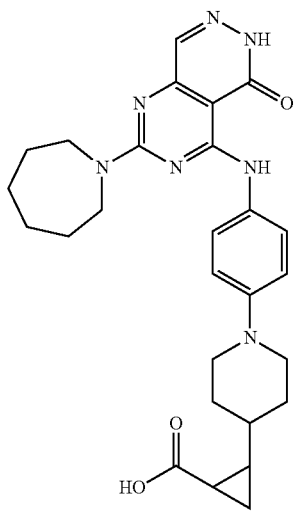<br>131 | 2-(1-(4-((2-(azepan-1-yl)-5-oxo-5,6-dihydropyrimido[4,5-d]pyridazin-4-yl)amino)phenyl)piperidin-4-yl)cyclopropanecarboxylic acid |
| 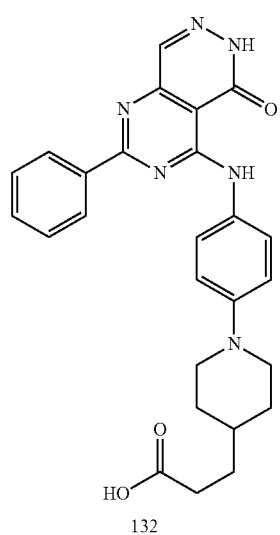 [SMILES: O=C(O)CCC1CCN(c2ccc(Nc3nc(-c4ccccc4)nc4cn[nH]c(=O)c34)cc2)CC1]<br>132 | 3-(1-(4-((5-oxo-2-phenyl-5,6-dihydropyrimido[4,5-d]pyridazin-4-yl)amino)phenyl)piperidin-4-yl)propanoic acid |

| Structure | IUPAC Name |
|---|---|
| 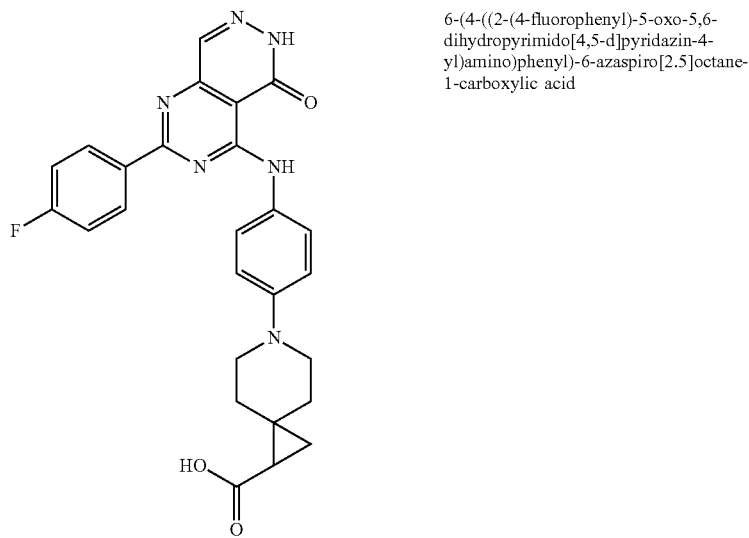 133 | 6-(4-((2-(4-fluorophenyl)-5-oxo-5,6-dihydropyrimido[4,5-d]pyridazin-4-yl)amino)phenyl)-6-azaspiro[2.5]octane-1-carboxylic acid |
| 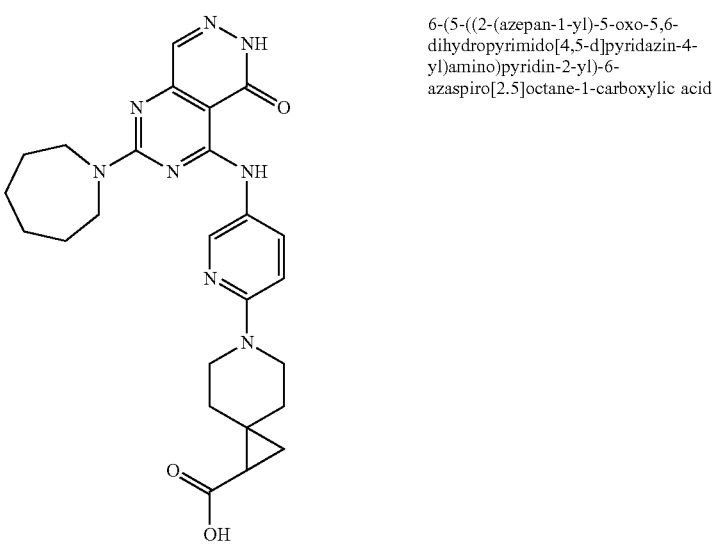 134 | 6-(5-((2-(azepan-1-yl)-5-oxo-5,6-dihydropyrimido[4,5-d]pyridazin-4-yl)amino)pyridin-2-yl)-6-azaspiro[2.5]octane-1-carboxylic acid |

TABLE 1-continued
| Structure | IUPAC Name |
|---|---|
| 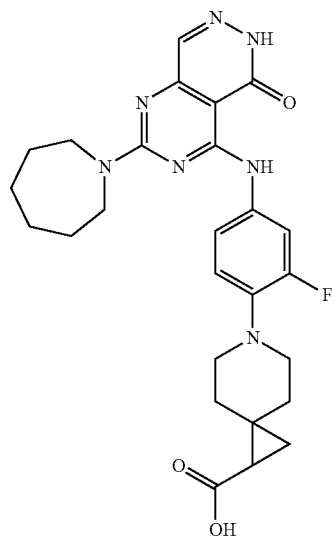 135 | 6-(4-((2-(azepan-1-yl)-5-oxo-5,6-dihydropyrimido[4,5-d]pyridazin-4-yl)amino)-2-fluorophenyl)-6-azaspiro[2.5]octane-1-carboxylic acid |
| 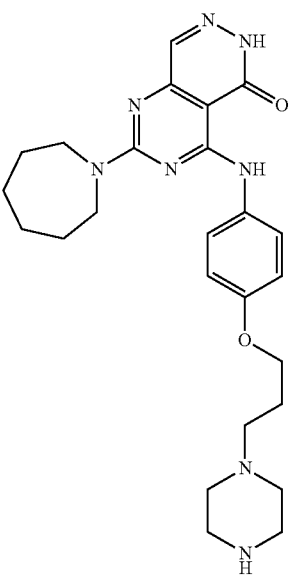 136 | 2-(azepan-1-yl)-4-((4-(3-(piperazin-1-yl)propoxy)phenyl)amino)pyrimido[4,5-d]pyridazin-5(6H)-one |

| Structure | IUPAC Name |
|---|---|
| 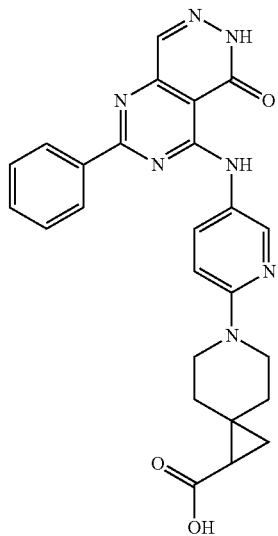 137 | 6-(5-((5-oxo-2-phenyl-5,6-dihydropyrimido[4,5-d]pyridazin-4-yl)amino)pyridin-2-yl)-6-azaspiro[2.5]octane-1-carboxylic acid |
| 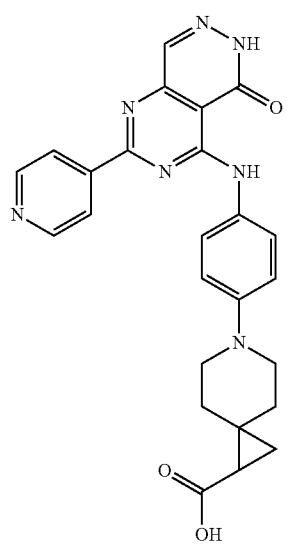 138 | 6-(4-((5-oxo-2-(pyridin-4-yl)-5,6-dihydropyrimido[4,5-d]pyridazin-4-yl)amino)phenyl)-6-azaspiro[2.5]octane-1-carboxylic acid |

TABLE 1-continued
| Structure | IUPAC Name |
|---|---|
| 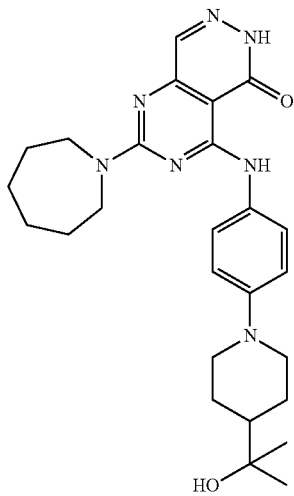 139 | 2-(azepan-1-yl)-4-((4-(4-(2-hydroxypropan-2-yl)piperidin-1-yl)phenyl)amino)pyrimido[4,5-d]pyridazin-5(6H)-one |
| 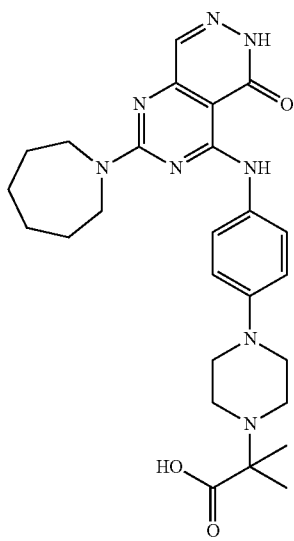 140 | 2-(4-(4-((2-(azepan-1-yl)-5-oxo-5,6-dihydropyrimido[4,5-d]pyridazin-4-yl)amino)phenyl)piperazin-1-yl)-2-methylpropanoic acid |

TABLE 1-continued
| Structure | IUPAC Name |
|---|---|
| 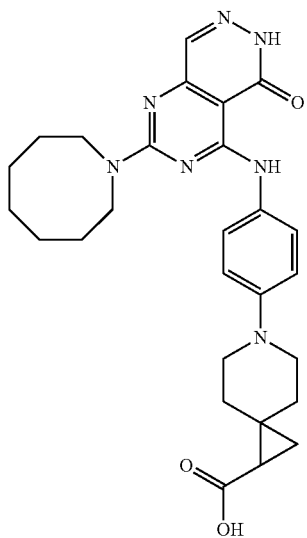 141 | 6-(4-((2-(azocan-1-yl)-5-oxo-5,6-dihydropyrimido[4,5-d]pyridazin-4-yl)amino)phenyl)-6-azaspiro[2.5]octane-1-carboxylic acid |
| 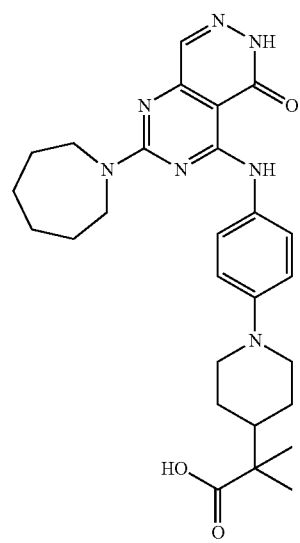 142 | 2-(1-(4-((2-(azepan-1-yl)-5-oxo-5,6-dihydropyrimido[4,5-d]pyridazin-4-yl)amino)phenyl)piperidin-4-yl)-2-methylpropanoic acid |

TABLE 1-continued
| Structure | IUPAC Name |
|---|---|
| 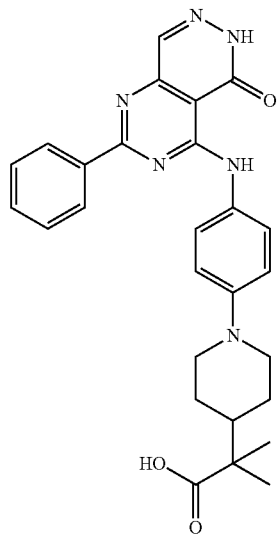<br>143 | 2-methyl-2-(1-(4-((5-oxo-2-phenyl-5,6-dihydropyrimido[4,5-d]pyridazin-4-yl)amino)phenyl)piperidin-4-yl)propanoic acid |
| 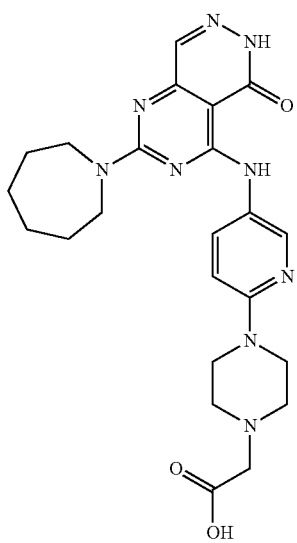<br>144 | 2-(4-(5-((2-(azepan-1-yl)-5-oxo-5,6-dihydropyrimido[4,5-d]pyridazin-4-yl)amino)pyridin-2-yl)piperazin-1-yl)acetic acid |

TABLE 1-continued
| Structure | IUPAC Name |
|---|---|
| 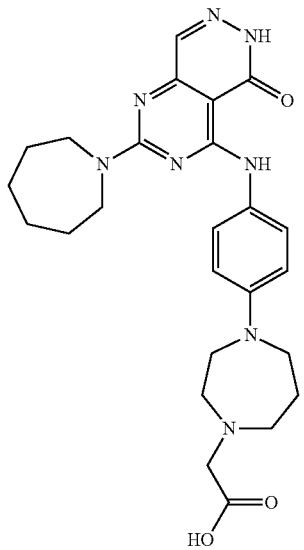 145 | 2-(4-(4-((2-(azepan-1-yl)-5-oxo-5,6-dihydropyrimido[4,5-d]pyridazin-4-yl)amino)phenyl)-1,4-diazepan-1-yl)acetic acid |
| 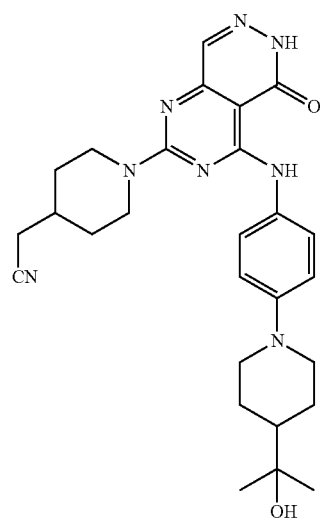 146 | 2-(1-(4-((4-(4-(2-hydroxypropan-2-yl)piperidin-1-yl)phenyl)amino)-5-oxo-5,6-dihydropyrimido[4,5-d]pyridazin-2-yl)piperidin-4-yl)acetonitrile |

TABLE 1-continued
| Structure | IUPAC Name |
|---|---|
| 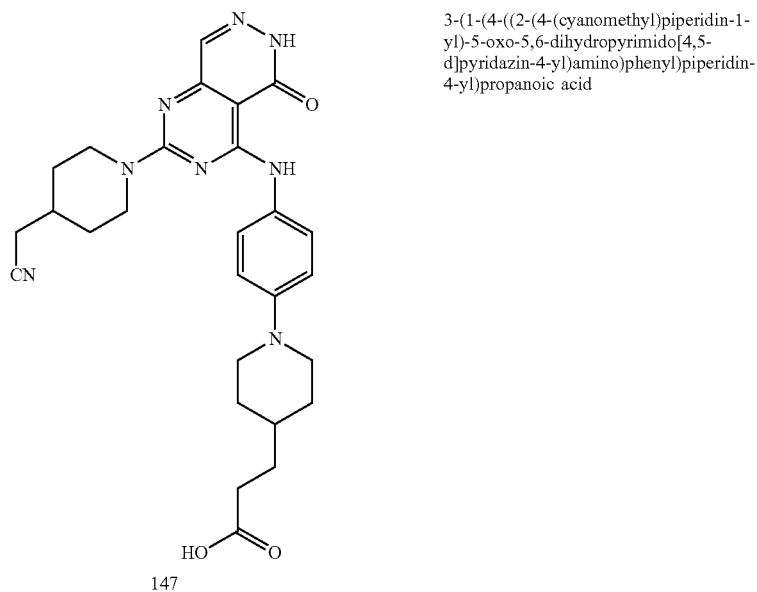<br>147 | 3-(1-(4-((2-(4-(cyanomethyl)piperidin-1-yl)-5-oxo-5,6-dihydropyrimido[4,5-d]pyridazin-4-yl)amino)phenyl)piperidin-4-yl)propanoic acid |
| 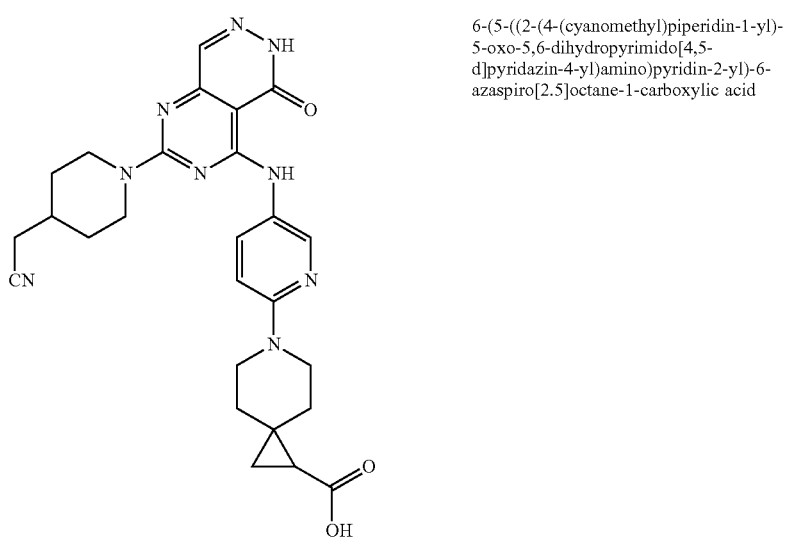<br>148 | 6-(5-((2-(4-(cyanomethyl)piperidin-1-yl)-5-oxo-5,6-dihydropyrimido[4,5-d]pyridazin-4-yl)amino)pyridin-2-yl)-6-azaspiro[2.5]octane-1-carboxylic acid |

TABLE 1-continued
| Structure | IUPAC Name |
|---|---|
| 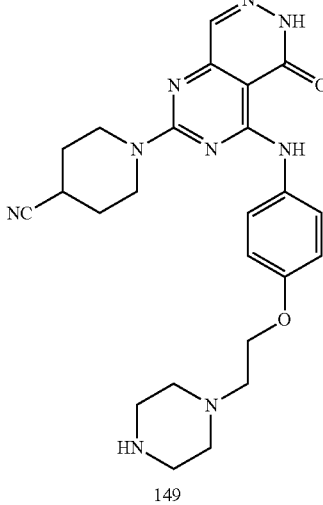 149 | 1-(5-oxo-4-((4-(2-(piperazin-1-yl)ethoxy)phenyl)amino)-5,6-dihydropyrimido[4,5-d]pyridazin-2-yl)piperidine-4-carbonitrile |
| 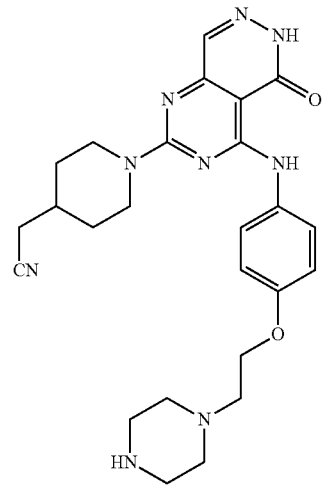 150 | 2-(1-(5-oxo-4-((4-(2-(piperazin-1-yl)ethoxy)phenyl)amino)-5,6-dihydropyrimido[4,5-d]pyridazin-2-yl)piperidin-4-yl)acetonitrile |
| 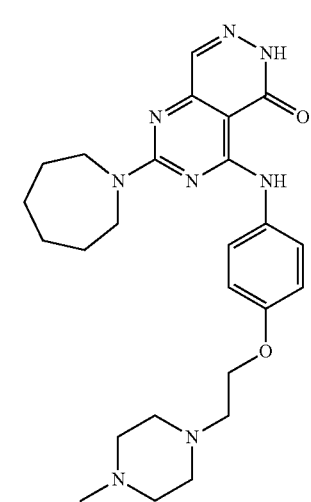 151 | 2-(azepan-1-yl)-4-((4-(2-(4-ethylpiperazin-1-yl)ethoxy)phenyl)amino)pyrimido[4,5-d]pyridazin-5(6H)-one |

TABLE 1-continued
| Structure | IUPAC Name |
|---|---|
| 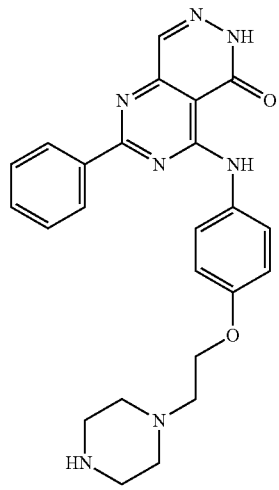<br>152 | 2-phenyl-4-((4-(2-(piperazin-1-yl)ethoxy)phenyl)amino)pyrimido[4,5-d]pyridazin-5(6H)-one |
| 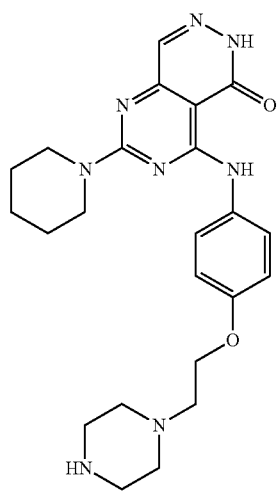<br>153 | 4-((4-(2-(piperazin-1-yl)ethoxy)phenyl)amino)-2-(piperidin-1-yl)pyrimido[4,5-d]pyridazin-5(6H)-one |

TABLE 1-continued
| Structure | IUPAC Name |
|---|---|
| 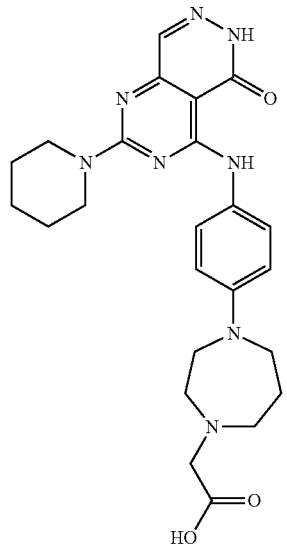 154 | 2-(4-(4-((5-oxo-2-(piperidin-1-yl)-5,6-dihydropyrimido[4,5-d]pyridazin-4-yl)amino)phenyl)-1,4-diazepan-1-yl)acetic acid |
| 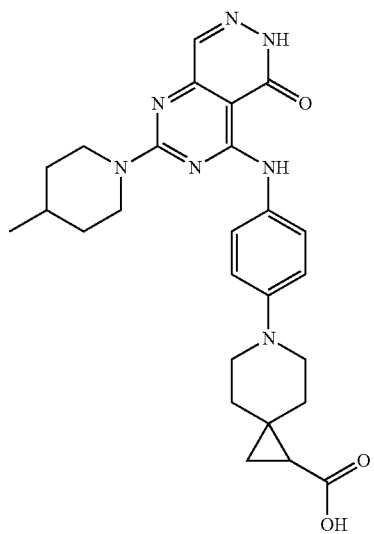 155 | 6-(4-((2-(4-methylpiperidin-1-yl)-5-oxo-5,6-dihydropyrimido[4,5-d]pyridazin-4-yl)amino)phenyl)-6-azaspiro[2.5]octane-1-carboxylic acid |

TABLE 1-continued
| Structure | IUPAC Name |
|---|---|
| 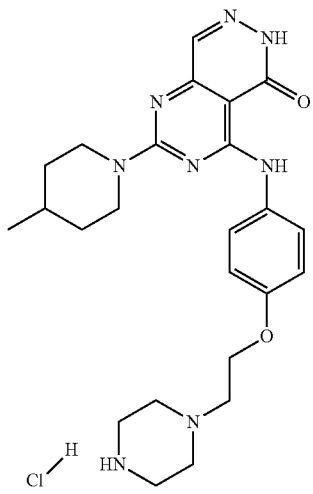 156 | 2-(4-methylpiperidin-1-yl)-4-((4-(2-(piperazin-1-yl)ethoxy)phenyl)amino)pyrimido[4,5-d]pyridazin-5(6H)-one hydrochloride |
| 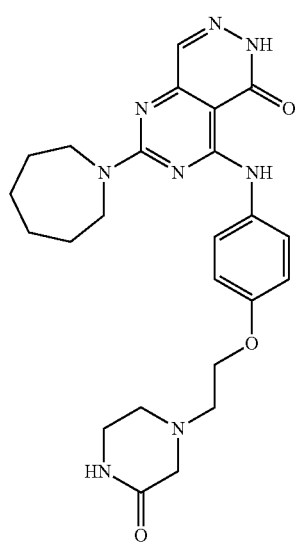 157 | 2-(azepan-1-yl)-4-((4-(2-(3-oxopiperazin-1-yl)ethoxy)phenyl)amino)pyrimido[4,5-d]pyridazin-5(6H)-one |

TABLE 1-continued
| Structure | IUPAC Name |
|---|---|
| 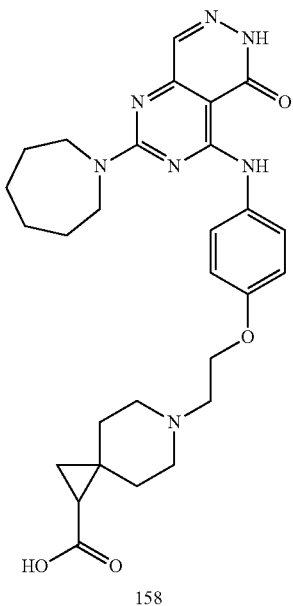 [SMILES: O=C(O)C1CC12CCN(CCOc1ccc(Nc3nc(N4CCCCCC4)nc4cn[nH]c(=O)c34)cc1)CC2] 158 | 6-(2-(4-((2-(azepan-1-yl)-5-oxo-5,6-dihydropyrimido[4,5-d]pyridazin-4-yl)amino)phenoxy)ethyl)-6-azaspiro[2.5]octane-1-carboxylic acid |
| 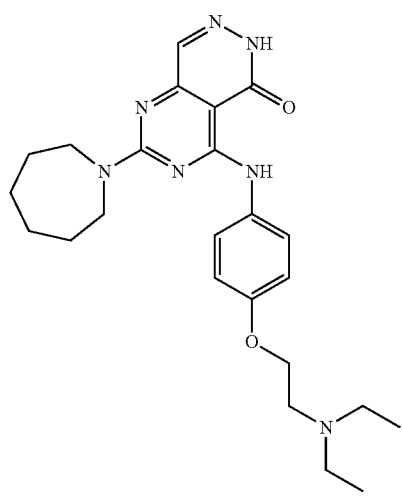 159 | 2-(azepan-1-yl)-4-((4-(2-(diethylamino)ethoxy)phenyl)amino)pyrimido[4,5-d]pyridazin-5(6H)-one |

TABLE 1-continued
| Structure | IUPAC Name |
|---|---|
| 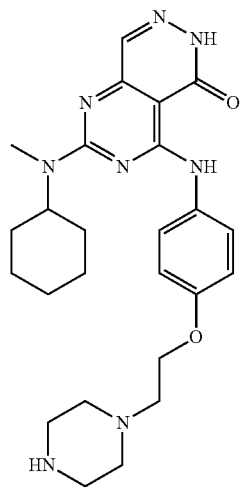<br>160 | 2-(cyclohexyl(methyl)amino)-4-((4-(2-(piperazin-1-yl)ethoxy)phenyl)amino)pyrimido[4,5-d]pyridazin-5(6H)-one |
| 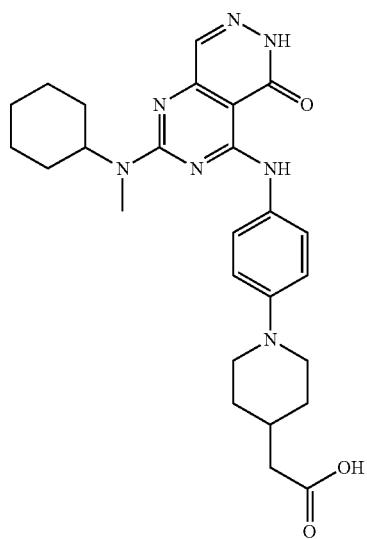<br>161 | 2-(1-(4-((2-(cyclohexyl(methyl)amino)-5-oxo-5,6-dihydropyrimido[4,5-d]pyridazin-4-yl)amino)phenyl)piperidin-4-yl)acetic acid |

TABLE 1-continued

| Structure | IUPAC Name |
| --- | --- |
| 162 | 2-(4-(4-((2-(4-(cyanomethyl)piperidin-1-yl)-5-oxo-5,6-dihydropyrimido[4,5-d]pyridazin-4-yl)amino)phenyl)piperazin-1-yl)acetic acid |
| 163 | 2-(1-(4-((2-(3-methoxyphenyl)-5-oxo-5,6-dihydropyrimido[4,5-d]pyridazin-4-yl)amino)phenyl)piperidin-4-yl)acetonitrile |
| 164 | 4-((4-(2-(1,4-diazepan-1-yl)ethoxy)phenyl)amino)-2-(azepan-1-yl)pyrimido[4,5-d]pyridazin-5(6H)-one |

TABLE 1-continued
| Structure | IUPAC Name |
|---|---|
| 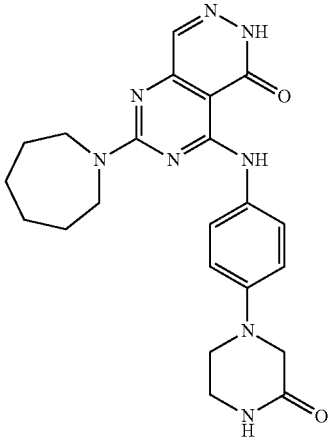 165 | 2-(azepan-1-yl)-4-((4-(3-oxopiperazin-1-yl)phenyl)amino)pyrimido[4,5-d]pyridazin-5(6H)-one |
| 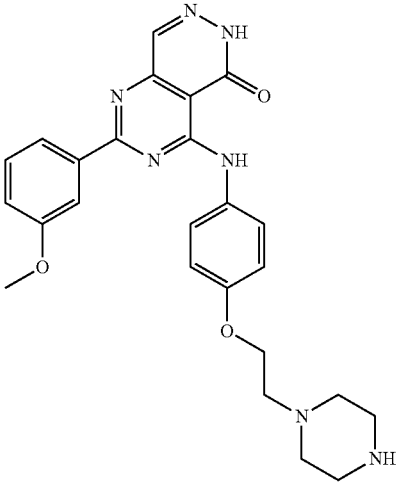 166 | 2-(3-methoxyphenyl)-4-((4-(2-(piperazin-1-yl)ethoxy)phenyl)amino)pyrimido[4,5-d]pyridazin-5(6H)-one |
| 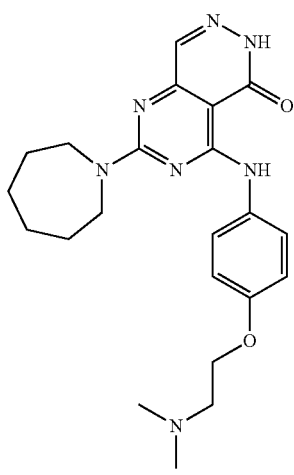 167 | 2-(azepan-1-yl)-4-((4-(2-(dimethylamino)ethoxy)phenyl)amino)pyrimido[4,5-d]pyridazin-5(6H)-one |

TABLE 1-continued

| Structure | IUPAC Name |
| --- | --- |
| 168 | 2-(azepan-1-yl)-4-((4-(2-(piperidin-4-yl)ethoxy)phenyl)amino)pyrimido[4,5-d]pyridazin-5(6H)-one |
| 169 | 2-(1-(5-oxo-4-((4-(2-(piperidin-4-yl)ethoxy)phenyl)amino)-5,6-dihydropyrimido[4,5-d]pyridazin-2-yl)piperidin-4-yl)acetonitrile |
| 170 | 6-(4-((2-(cyclohexyl(methyl)amino)-5-oxo-5,6-dihydropyrimido[4,5-d]pyridazin-4-yl)amino)phenyl)-6-azaspiro[2.5]octane-1-carboxylic acid |

TABLE 1-continued

| Structure | IUPAC Name |
|---|---|
| 171 | 4-((4-(2-(1,4-diazepan-1-yl)ethoxy)phenyl)amino)-2-(piperidin-1-yl)pyrimido[4,5-d]pyridazin-5(6H)-one |
| 172 | 2-(azepan-1-yl)-4-((4-(2-(4-hydroxypiperidin-1-yl)ethoxy)phenyl)amino)pyrimido[4,5-d]pyridazin-5(6H)-one |
| 173 | 2-(azepan-1-yl)-4-((4-(3-(piperazin-1-yl)propyl)phenyl)amino)pyrimido[4,5-d]pyridazin-5(6H)-one |

TABLE 1-continued
| Structure | IUPAC Name |
|---|---|
| 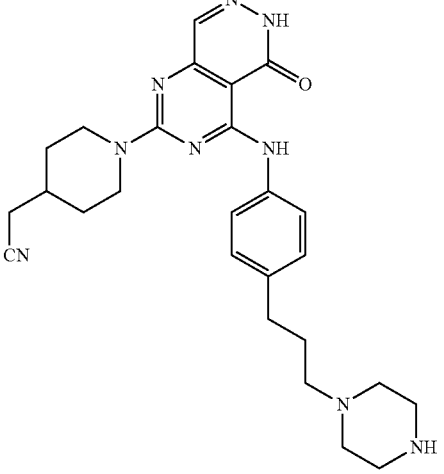 174 | 2-(1-(5-oxo-4-((4-(3-(piperazin-1-yl)propyl)phenyl)amino)-5,6-dihydropyrimido[4,5-d]pyridazin-2-yl)piperidin-4-yl)acetonitrile |
| 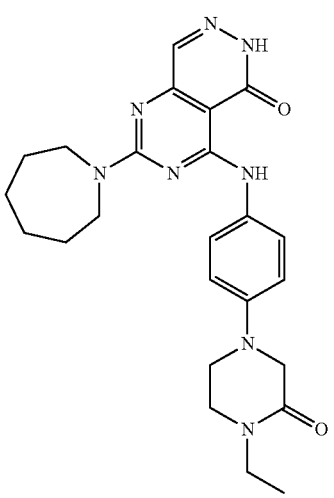 175 | 2-(azepan-1-yl)-4-((4-(4-ethyl-3-oxopiperazin-1-yl)phenyl)amino)pyrimido[4,5-d]pyridazin-5(6H)-one |
| 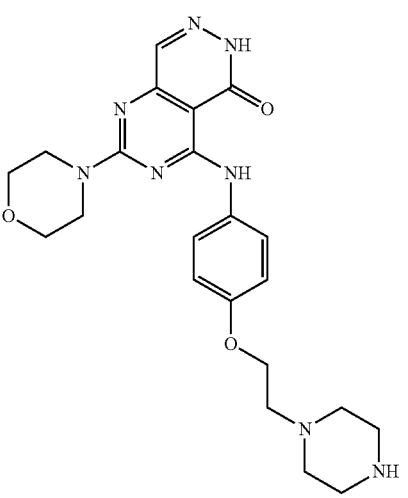 176 | 2-morpholino-4-((4-(2-(piperazin-1-yl)ethoxy)phenyl)amino)pyrimido[4,5-d]pyridazin-5(6H)-one |

TABLE 1-continued

| Structure | IUPAC Name |
|---|---|
| 177 | 2-(2,6-dimethylmorpholino)-4-((4-(2-(piperazin-1-yl)ethoxy)phenyl)amino)pyrimido[4,5-d]pyridazin-5(6H)-one |
| 178 | 2-(1-(4-((4-(4-ethyl-3-oxopiperazin-1-yl)phenyl)amino)-5-oxo-5,6-dihydropyrimido[4,5-d]pyridazin-2-yl)piperidin-4-yl)acetonitrile |
| 179 | 2-(azepan-1-yl)-4-((4-(3-(4-hydroxypiperidin-1-yl)propyl)phenyl)amino)pyrimido[4,5-d]pyridazin-5(6H)-one |

TABLE 1-continued

| Structure | IUPAC Name |
| --- | --- |
| 180 | 2-(azepan-1-yl)-4-((4-(4-ethylpiperazin-1-yl)phenyl)amino)pyrimido[4,5-d]pyridazin-5(6H)-one |
| 181 | 4-((6-(2-(piperazin-1-yl)ethoxy)pyridin-3-yl)amino)-2-(piperidin-1-yl)pyrimido[4,5-d]pyridazin-5(6H)-one |
| 182 | 2-(azepan-1-yl)-4-((6-(2-(piperazin-1-yl)ethoxy)pyridin-3-yl)amino)pyrimido[4,5-d]pyridazin-5(6H)-one |

| Structure | IUPAC Name |
|---|---|
| 183 | 4-((4-(2-(4-hydroxypiperidin-1-yl)ethoxy)phenyl)amino)-2-(piperidin-1-yl)pyrimido[4,5-d]pyridazin-5(6H)-one |
| 184 | 2-(azepan-1-yl)-4-((4-(2-(4-hydroxy-4-methylpiperidin-1-yl)ethoxy)phenyl)amino)pyrimido[4,5-d]pyridazin-5(6H)-one |
| 185 | 2-(1-(4-((4-(2-(4-hydroxy-4-methylpiperidin-1-yl)ethoxy)phenyl)amino)-5-oxo-5,6-dihydropyrimido[4,5-d]pyridazin-2-yl)piperidin-4-yl)acetonitrile |

TABLE 1-continued
| Structure | IUPAC Name |
|---|---|
| 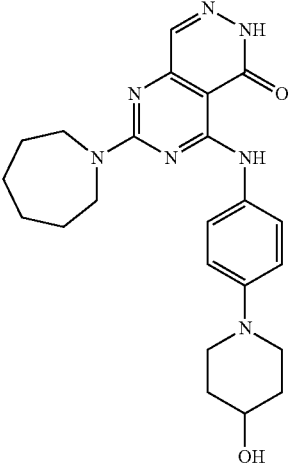 186 | 2-(azepan-1-yl)-4-((4-(4-hydroxypiperidin-1-yl)phenyl)amino)pyrimido[4,5-d]pyridazin-5(6H)-one |
| 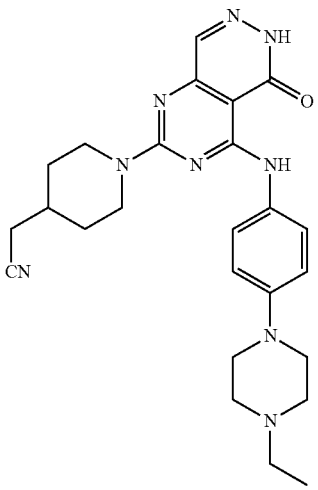 187 | 2-(1-(4-((4-(4-ethylpiperazin-1-yl)phenyl)amino)-5-oxo-5,6-dihydropyrimido[4,5-d]pyridazin-2-yl)piperidin-4-yl)acetonitrile |
| 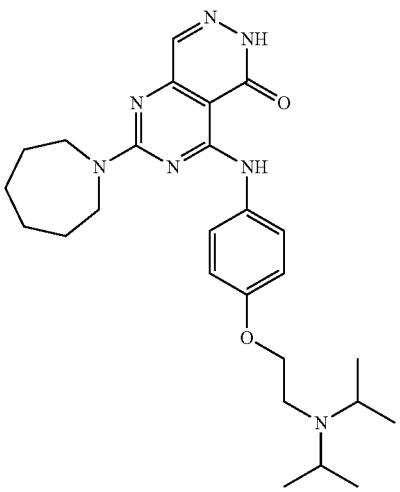 188 | 2-(azepan-1-yl)-4-((4-(2-(diisopropylamino)ethoxy)phenyl)amino)pyrimido[4,5-d]pyridazin-5(6H)-one |

TABLE 1-continued
| Structure | IUPAC Name |
|---|---|
| 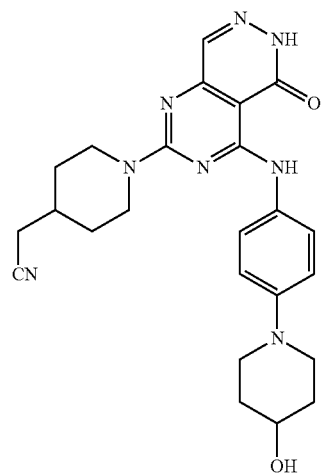 [SMILES: N#CCC1CCN(c2nc(Nc3ccc(N4CCNCC4)nc3)c3c(=O)[nH]ncc3n2)CC1] 189 | 2-(1-(4-((4-(4-hydroxypiperidin-1-yl)phenyl)amino)-5-oxo-5,6-dihydropyrimido[4,5-d]pyridazin-2-yl)piperidin-4-yl)acetonitrile |
| 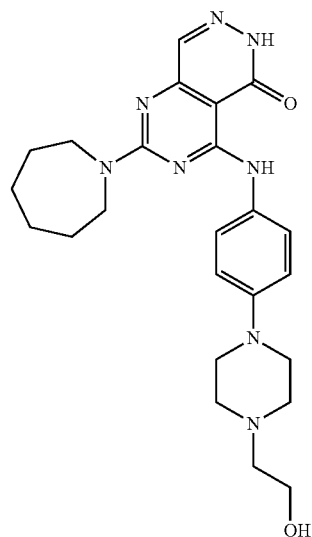 190 | 2-(azepan-1-yl)-4-((4-(4-(2-hydroxyethyl)piperazin-1-yl)phenyl)amino)pyrimido[4,5-d]pyridazin-5(6H)-one |

TABLE 1-continued
| Structure | IUPAC Name |
|---|---|
| 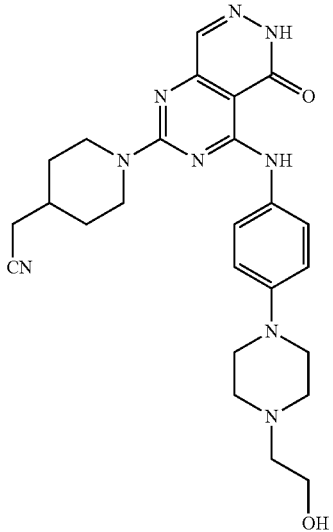 191 | 2-(1-(4-((4-(4-(2-hydroxyethyl)piperazin-1-yl)phenyl)amino)-5-oxo-5,6-dihydropyrimido[4,5-d]pyridazin-2-yl)piperidin-4-yl)acetonitrile |
| 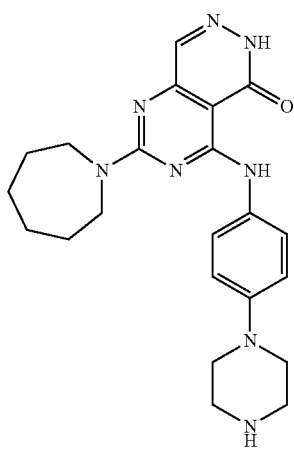 192 | 2-(azepan-1-yl)-4-((4-(piperazin-1-yl)phenyl)amino)pyrimido[4,5-d]pyridazin-5(6H)-one |
| 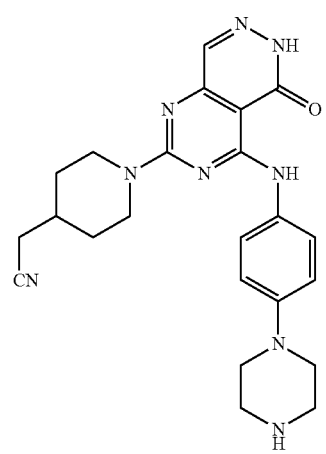 193 | 2-(1-(5-oxo-4-((4-(piperazin-1-yl)phenyl)amino)-5,6-dihydropyrimido[4,5-d]pyridazin-2-yl)piperidin-4-yl)acetonitrile |

TABLE 1-continued
| Structure | IUPAC Name |
|---|---|
| 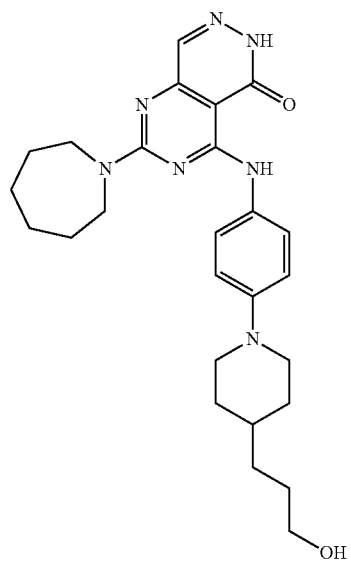 194 | 2-(azepan-1-yl)-4-((4-(4-(3-hydroxypropyl)piperidin-1-yl)phenyl)amino)pyrimido[4,5-d]pyridazin-5(6H)-one |
| 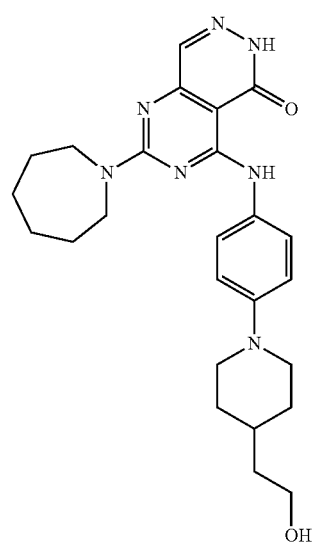 195 | 2-(azepan-1-yl)-4-((4-(4-(2-hydroxyethyl)piperidin-1-yl)phenyl)amino)pyrimido[4,5-d]pyridazin-5(6H)-one |

TABLE 1-continued
| Structure | IUPAC Name |
|---|---|
| 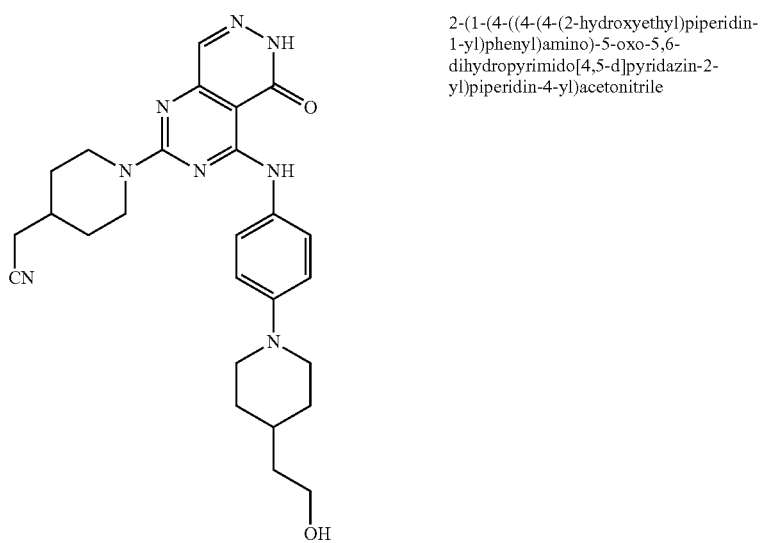  196 | 2-(1-(4-((4-(4-(2-hydroxyethyl)piperidin-1-yl)phenyl)amino)-5-oxo-5,6-dihydropyrimido[4,5-d]pyridazin-2-yl)piperidin-4-yl)acetonitrile |
| 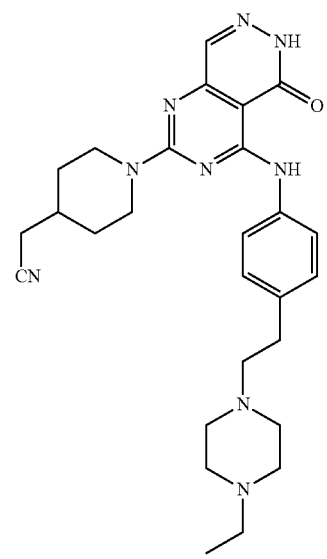  197 | 2-(1-(4-((4-(2-(4-ethylpiperazin-1-yl)ethyl)phenyl)amino)-5-oxo-5,6-dihydropyrimido[4,5-d]pyridazin-2-yl)piperidin-4-yl)acetonitrile |

TABLE 1-continued
| Structure | IUPAC Name |
|---|---|
| 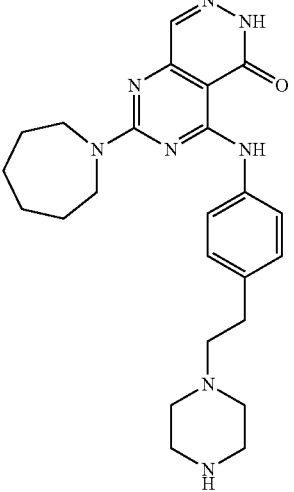 198 | 2-(azepan-1-yl)-4-((4-(2-(piperazin-1-yl)ethyl)phenyl)amino)pyrimido[4,5-d]pyridazin-5(6H)-one |
| 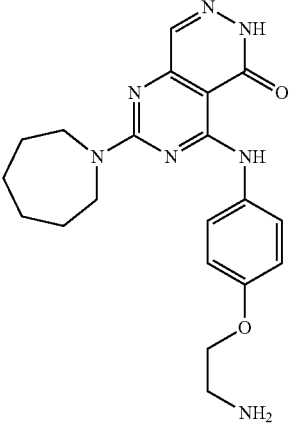 199 | 4-((4-(2-aminoethoxy)phenyl)amino)-2-(azepan-1-yl)pyrimido[4,5-d]pyridazin-5(6H)-one |
| 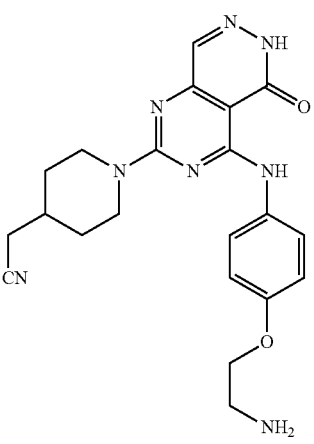 200 | 2-(1-(4-((4-(2-aminoethoxy)phenyl)amino)-5-oxo-5,6-dihydropyrimido[4,5-d]pyridazin-2-yl)piperidin-4-yl)acetonitrile |

TABLE 1-continued
| Structure | IUPAC Name |
|---|---|
| 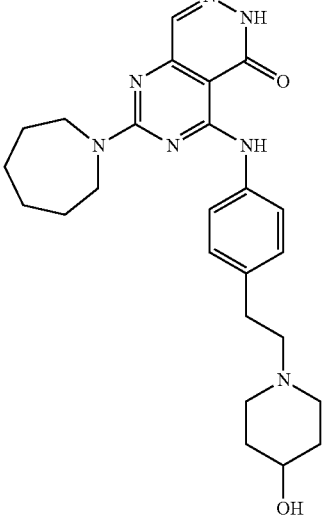 201 | 2-(azepan-1-yl)-4-((4-(2-(4-hydroxypiperidin-1-yl)ethyl)phenyl)amino)pyrimido[4,5-d]pyridazin-5(6H)-one |
| 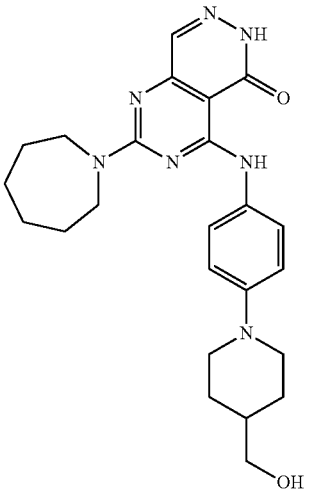 202 | 2-(azepan-1-yl)-4-((4-(4-(hydroxymethyl)piperidin-1-yl)phenyl)amino)pyrimido[4,5-d]pyridazin-5(6H)-one |
| 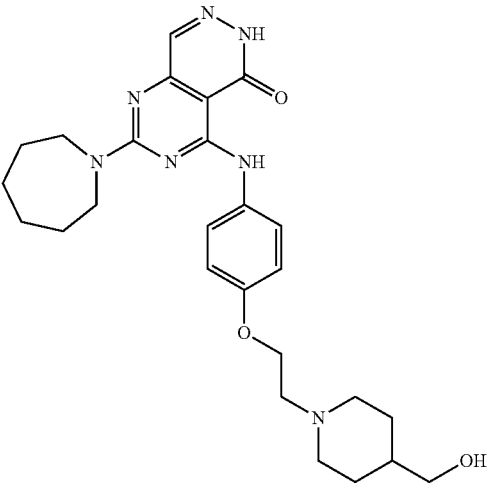 203 | 2-(azepan-1-yl)-4-((4-(2-(4-(hydroxymethyl)piperidin-1-yl)ethoxy)phenyl)amino)pyrimido[4,5-d]pyridazin-5(6H)-one |

TABLE 1-continued
| Structure | IUPAC Name |
|---|---|
| 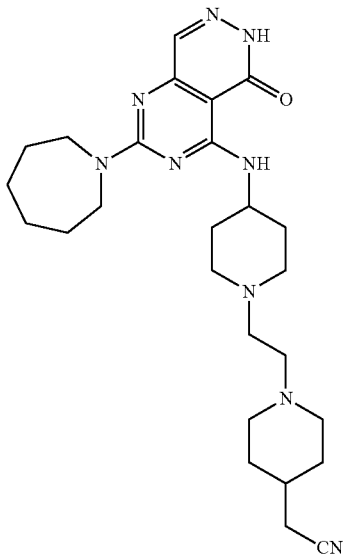<br>204 | 2-(1-(2-(4-((2-(azepan-1-yl)-5-oxo-5,6-dihydropyrimido[4,5-d]pyridazin-4-yl)amino)piperidin-1-yl)ethyl)piperidin-4-yl)acetonitrile |
| 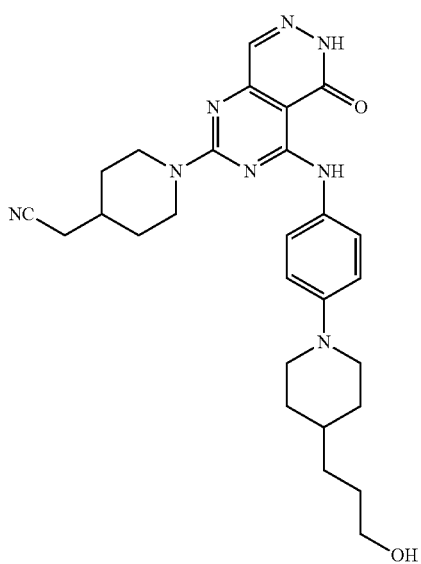<br>205 | 2-(1-(4-((4-(4-(3-hydroxypropyl)piperidin-1-yl)phenyl)amino)-5-oxo-5,6-dihydropyrimido[4,5-d]pyridazin-2-yl)piperidin-4-yl)acetonitrile |

TABLE 1-continued
| Structure | IUPAC Name |
|---|---|
| 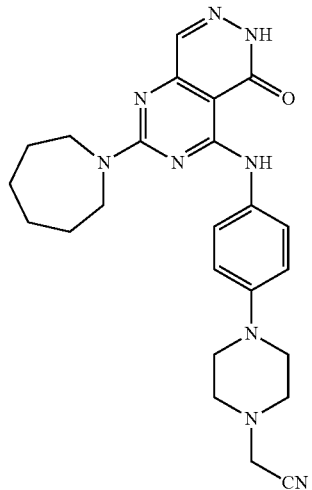 206 | 2-(4-(4-((2-(azepan-1-yl)-5-oxo-5,6-dihydropyrimido[4,5-d]pyridazin-4-yl)amino)phenyl)piperazin-1-yl)acetonitrile |
| 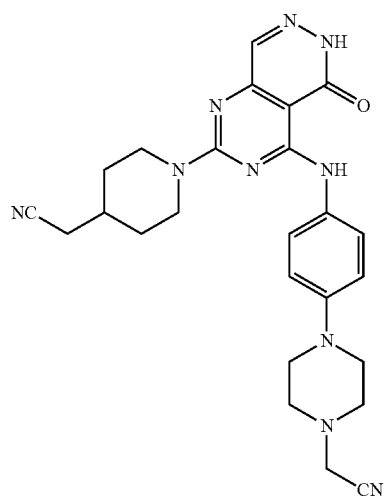 207 | 2-(1-(4-((4-(4-(cyanomethyl)piperazin-1-yl)phenyl)amino)-5-oxo-5,6-dihydropyrimido[4,5-d]pyridazin-2-yl)piperidin-4-yl)acetonitrile |

TABLE 1-continued
| Structure | IUPAC Name |
|---|---|
| 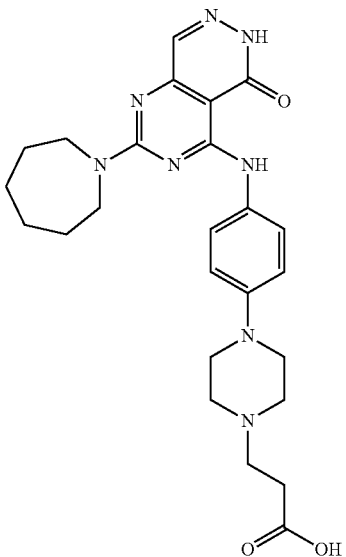 208 | 3-(4-(4-((2-(azepan-1-yl)-5-oxo-5,6-dihydropyrimido[4,5-d]pyridazin-4-yl)amino)phenyl)piperazin-1-yl)propanoic acid |
| 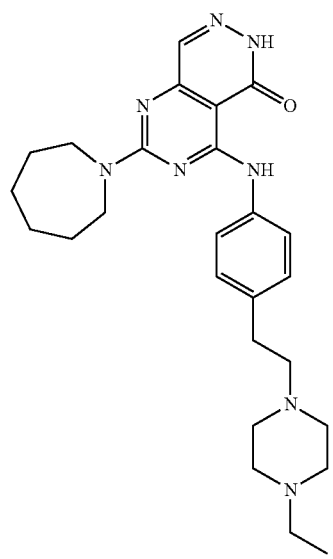 209 | 2-(azepan-1-yl)-4-((4-(2-(4-ethylpiperazin-1-yl)ethyl)phenyl)amino)pyrimido[4,5-d]pyridazin-5(6H)-one |

TABLE 1-continued
| Structure | IUPAC Name |
|---|---|
| 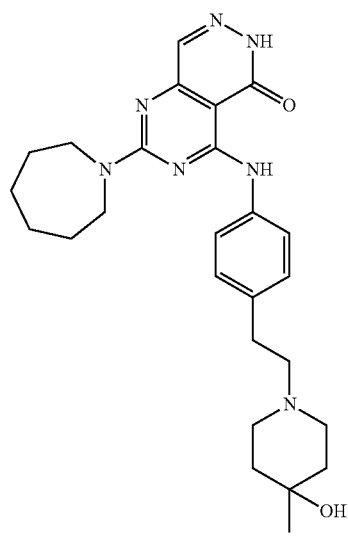 210 | 2-(azepan-1-yl)-4-((4-(2-(4-hydroxy-4-methylpiperidin-1-yl)ethyl)phenyl)amino)pyrimido[4,5-d]pyridazin-5(6H)-one |
| 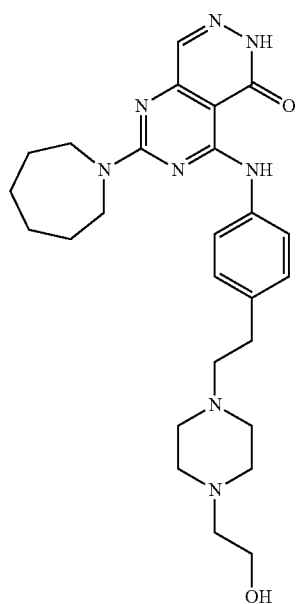 211 | 2-(azepan-1-yl)-4-((4-(2-(4-(2-hydroxyethyl)piperazin-1-yl)ethyl)phenyl)amino)pyrimido[4,5-d]pyridazin-5(6H)-one |

| Structure | IUPAC Name |
|---|---|
| 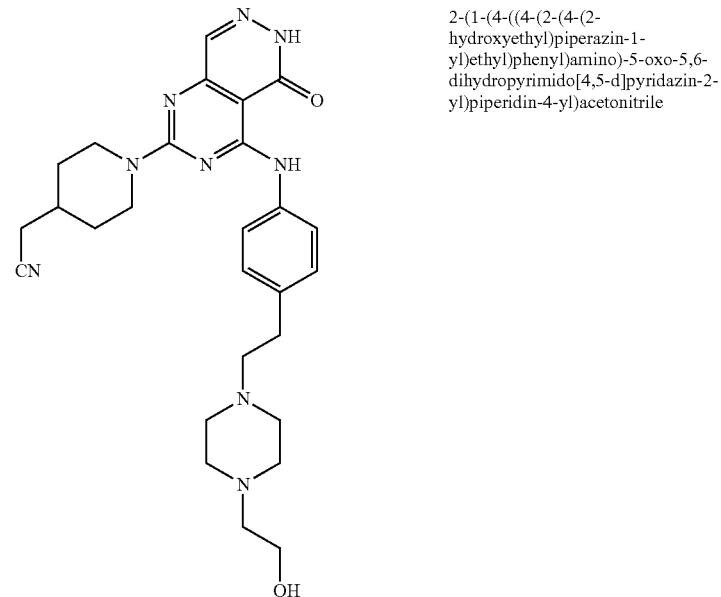<br>212 | 2-(1-(4-((4-(2-(4-(2-hydroxyethyl)piperazin-1-yl)ethyl)phenyl)amino)-5-oxo-5,6-dihydropyrimido[4,5-d]pyridazin-2-yl)piperidin-4-yl)acetonitrile |
| 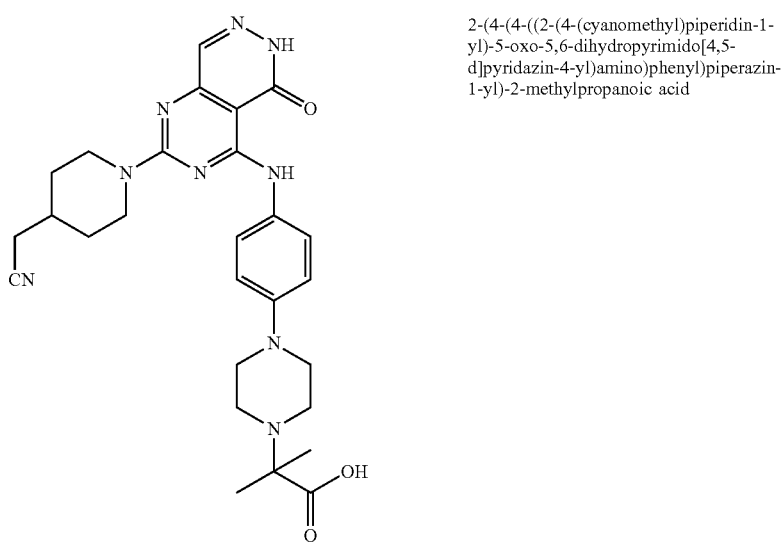<br>213 | 2-(4-(4-((2-(4-(cyanomethyl)piperidin-1-yl)-5-oxo-5,6-dihydropyrimido[4,5-d]pyridazin-4-yl)amino)phenyl)piperazin-1-yl)-2-methylpropanoic acid |

TABLE 1-continued

| Structure | IUPAC Name |
|---|---|
| 214 | 2-(azepan-1-yl)-4-((4-(4-(2-hydroxy-2-methylpropanoyl)piperazin-1-yl)phenyl)amino)pyrimido[4,5-d]pyridazin-5(6H)-one |
| 215 | 3-(4-(4-((2-(azepan-1-yl)-5-oxo-5,6-dihydropyrimido[4,5-d]pyridazin-4-yl)amino)phenyl)piperazin-1-yl)-3-oxopropanenitrile |
| 216 | 2-(1-(4-((4-(4-(hydroxymethyl)piperidin-1-yl)phenyl)amino)-5-oxo-5,6-dihydropyrimido[4,5-d]pyridazin-2-yl)piperidin-4-yl)acetonitrile |

TABLE 1-continued
| Structure | IUPAC Name |
|---|---|
| 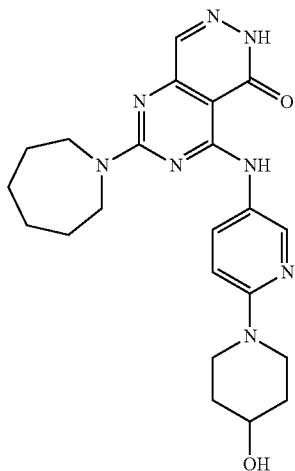<br>217 | 2-(azepan-1-yl)-4-((6-(4-hydroxypiperidin-1-yl)pyridin-3-yl)amino)pyrimido[4,5-d]pyridazin-5(6H)-one |
| 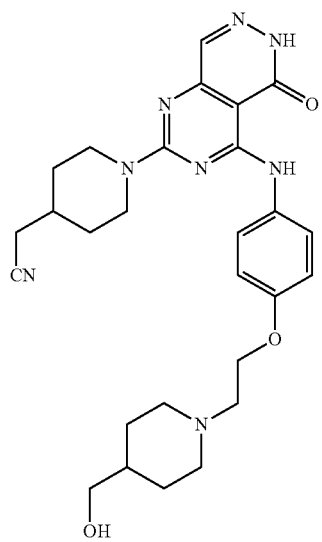<br>218 | 2-(1-(4-((4-(2-(4-(hydroxymethyl)piperidin-1-yl)ethoxy)phenyl)amino)-5-oxo-5,6-dihydropyrimido[4,5-d]pyridazin-2-yl)piperidin-4-yl)acetonitrile |

| Structure | IUPAC Name |
|---|---|
| 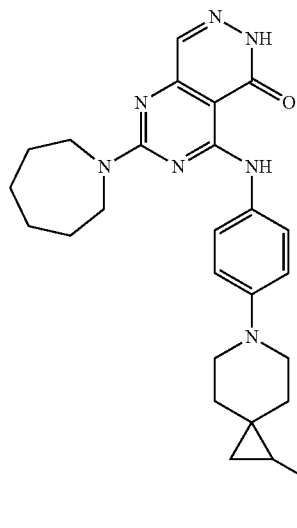<br>219 | (phosphonooxy)methyl 6-(4-((2-(azepan-1-yl)-5-oxo-5,6-dihydropyrimido[4,5-d]pyridazin-4-yl)amino)phenyl)-6-azaspiro[2.5]octane-1-carboxylate |
| 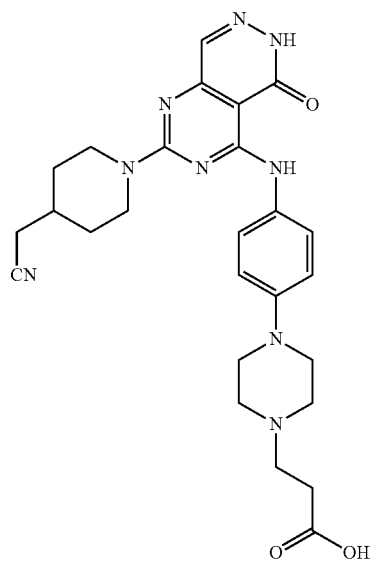<br>220 | 3-(4-(4-((2-(4-(cyanomethyl)piperidin-1-yl)-5-oxo-5,6-dihydropyrimido[4,5-d]pyridazin-4-yl)amino)phenyl)piperazin-1-yl)propanoic acid |

TABLE 1-continued
| Structure | IUPAC Name |
|---|---|
| 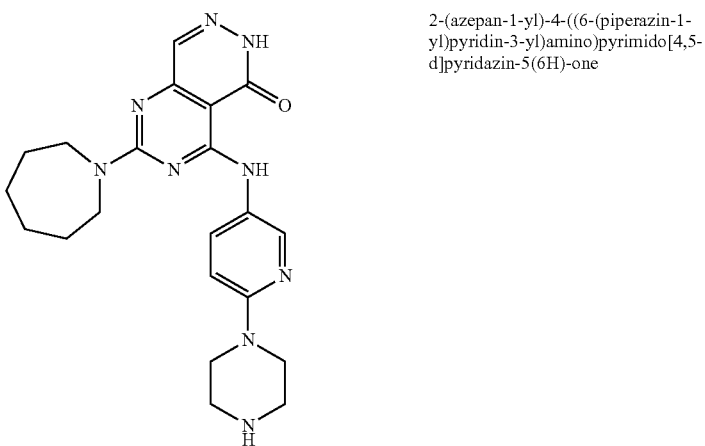 221 | 2-(azepan-1-yl)-4-((6-(piperazin-1-yl)pyridin-3-yl)amino)pyrimido[4,5-d]pyridazin-5(6H)-one |
| 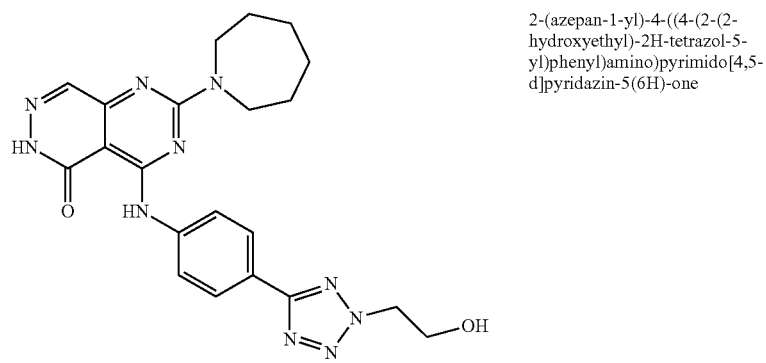 222 | 2-(azepan-1-yl)-4-((4-(2-(2-hydroxyethyl)-2H-tetrazol-5-yl)phenyl)amino)pyrimido[4,5-d]pyridazin-5(6H)-one |
| 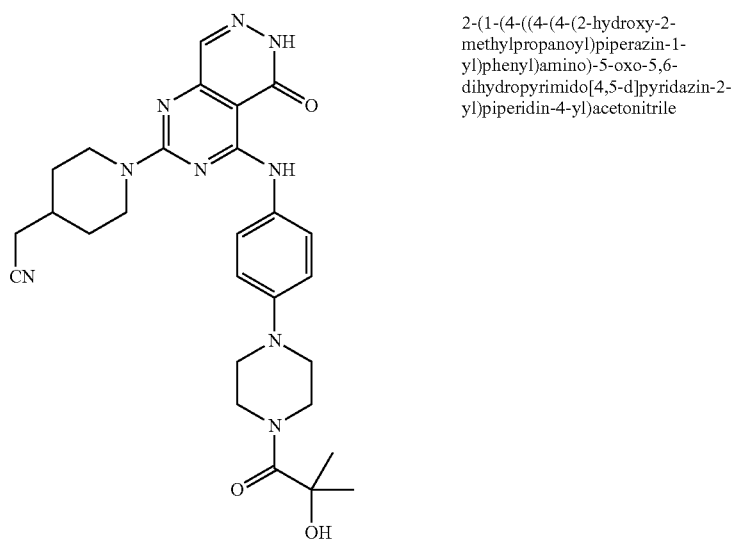 223 | 2-(1-(4-((4-(4-(2-hydroxy-2-methylpropanoyl)piperazin-1-yl)phenyl)amino)-5-oxo-5,6-dihydropyrimido[4,5-d]pyridazin-2-yl)piperidin-4-yl)acetonitrile |

TABLE 1-continued
| Structure | IUPAC Name |
|---|---|
| 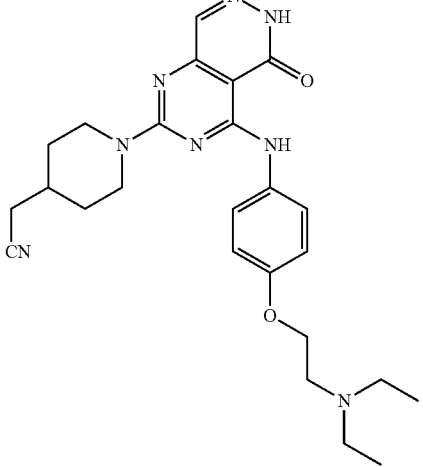 224 | 2-(1-(4-((4-(2-(diethylamino)ethoxy)phenyl)amino)-5-oxo-5,6-dihydropyrimido[4,5-d]pyridazin-2-yl)piperidin-4-yl)acetonitrile |
| 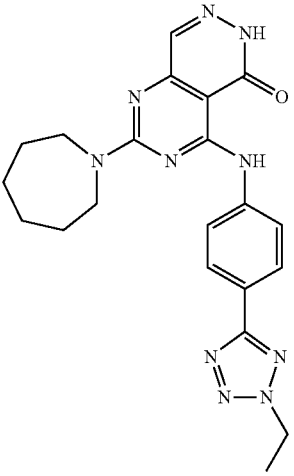 225 | 2-(azepan-1-yl)-4-((4-(2-ethyl-2H-tetrazol-5-yl)phenyl)amino)pyrimido[4,5-d]pyridazin-5(6H)-one |
| 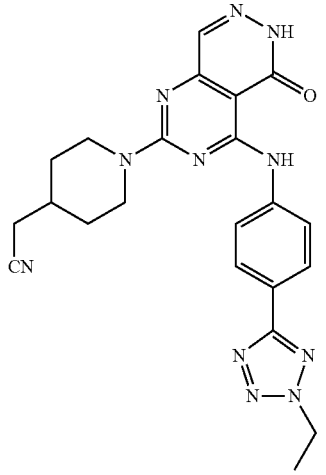 226 | 2-(1-(4-((4-(2-ethyl-2H-tetrazol-5-yl)phenyl)amino)-5-oxo-5,6-dihydropyrimido[4,5-d]pyridazin-2-yl)piperidin-4-yl)acetonitrile |

TABLE 1-continued

| Structure | IUPAC Name |
|---|---|
| 227 | 4-((4-(2H-tetrazol-5-yl)phenyl)amino)-2-(azepan-1-yl)pyrimido[4,5-d]pyridazin-5(6H)-one |
| 228 | 2-(1-(4-((6-(4-ethylpiperazin-1-yl)pyridin-3-yl)amino)-5-oxo-5,6-dihydropyrimido[4,5-d]pyridazin-2-yl)piperidin-4-yl)acetonitrile |
| 229 | 2-(azepan-1-yl)-4-((6-(4-ethylpiperazin-1-yl)pyridin-3-yl)amino)pyrimido[4,5-d]pyridazin-5(6H)-one |

TABLE 1-continued

| Structure | IUPAC Name |
| --- | --- |
| 230 | 2-(4-(5-oxo-4-((4-(2-(piperazin-1-yl)ethoxy)phenyl)amino)-5,6-dihydropyrimido[4,5-d]pyridazin-2-yl)piperazin-1-yl)acetonitrile |
| 231 | 2-(1-(5-oxo-4-((6-(piperazin-1-yl)pyridin-3-yl)amino)-5,6-dihydropyrimido[4,5-d]pyridazin-2-yl)piperidin-4-yl)acetonitrile |
| 232 | 2-(1-(4-((2-(azepan-1-yl)-5-oxo-5,6-dihydropyrimido[4,5-d]pyridazin-4-yl)amino)phenyl)piperidin-3-yl)acetic acid |

TABLE 1-continued

| Structure | IUPAC Name |
|---|---|
| 233 | 2-(1-(4-((2-(azepan-1-yl)-5-oxo-5,6-dihydropyrimido[4,5-d]pyridazin-4-yl)amino)phenyl)piperidin-3-yl)acetic acid |
| 234 | 3-(4-(5-((2-(azepan-1-yl)-5-oxo-5,6-dihydropyrimido[4,5-d]pyridazin-4-yl)amino)pyridin-2-yl)piperazin-1-yl)-3-oxopropanenitrile |
| 235 | 2-(5-(4-((2-(azepan-1-yl)-5-oxo-5,6-dihydropyrimido[4,5-d]pyridazin-4-yl)amino)phenyl)-2H-tetrazol-2-yl)acetic acid |

TABLE 1-continued
| Structure | IUPAC Name |
|---|---|
| 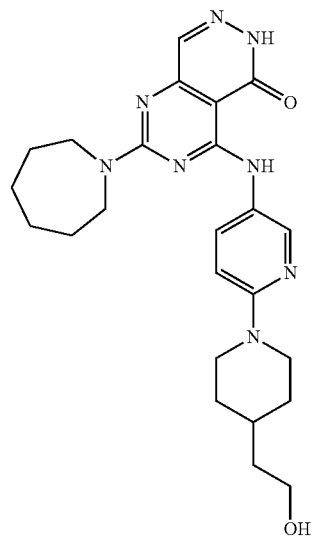 236 | 2-(azepan-1-yl)-4-((6-(4-(2-hydroxyethyl)piperidin-1-yl)pyridin-3-yl)amino)pyrimido[4,5-d]pyridazin-5(6H)-one |
| 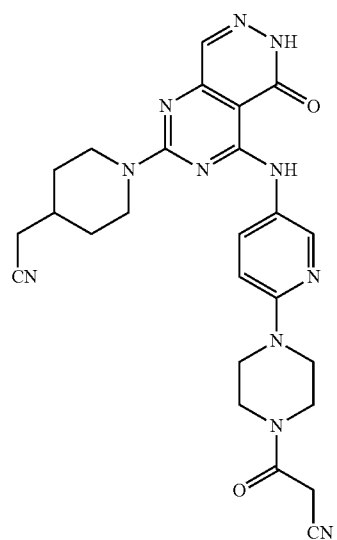 237 | 3-(4-(5-((2-(4-(cyanomethyl)piperidin-1-yl)-5-oxo-5,6-dihydropyrimido[4,5-d]pyridazin-4-yl)amino)pyridin-2-yl)piperazin-1-yl)-3-oxopropanenitrile |

TABLE 1-continued

| Structure | IUPAC Name |
|---|---|
| (238) | 2-(azepan-1-yl)-4-((6-(4-(2-hydroxy-2-methylpropanoyl)piperazin-1-yl)pyridin-3-yl)amino)pyrimido[4,5-d]pyridazin-5(6H)-one |
| (239) | 2-(azepan-1-yl)-4-((4-(2-(4-(2-hydroxyethyl)piperazin-1-yl)ethoxy)phenyl)amino)pyrimido[4,5-d]pyridazin-5(6H)-one |
| (240) | 3-(4-(4-((2-(4-(cyanomethyl)piperidin-1-yl)-5-oxo-5,6-dihydropyrimido[4,5-d]pyridazin-4-yl)amino)phenyl)piperazin-1-yl)-3-oxopropanenitrile |

TABLE 1-continued
| Structure | IUPAC Name |
|---|---|
| 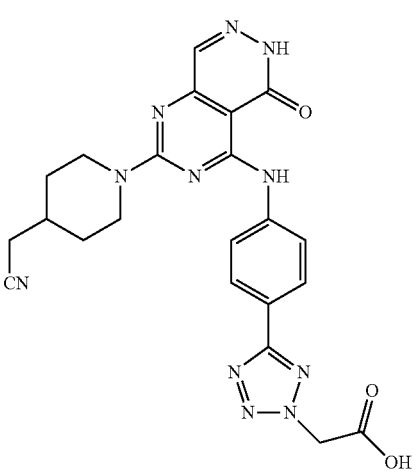 241 | 2-(5-(4-((2-(4-(cyanomethyl)piperidin-1-yl)-5-oxo-5,6-dihydropyrimido[4,5-d]pyridazin-4-yl)amino)phenyl)-2H-tetrazol-2-yl)acetic acid |
| 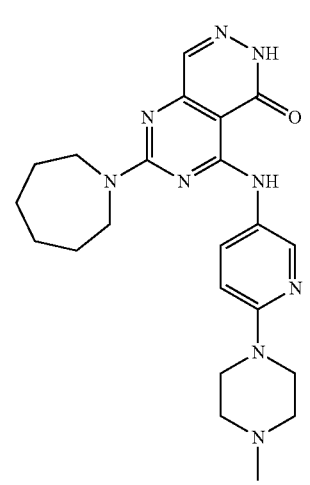 242 | 2-(azepan-1-yl)-4-((6-(4-methylpiperazin-1-yl)pyridin-3-yl)amino)pyrimido[4,5-d]pyridazin-5(6H)-one |
| 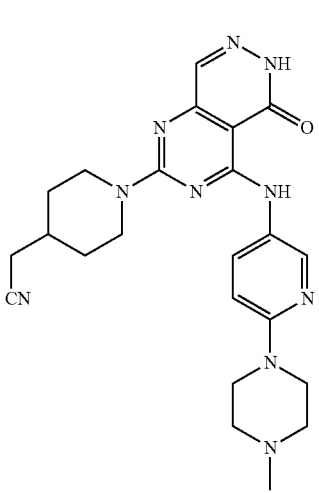 243 | 2-(1-(4-((6-(4-methylpiperazin-1-yl)pyridin-3-yl)amino)-5-oxo-5,6-dihydropyrimido[4,5-d]pyridazin-2-yl)piperidin-4-yl)acetonitrile |

TABLE 1-continued

| Structure | IUPAC Name |
|---|---|
| 244 | 4-((4-(4-((2H-tetrazol-5-yl)methyl)piperidin-1-yl)phenyl)amino)-2-(azepan-1-yl)pyrimido[4,5-d]pyridazin-5(6H)-one |
| 245 | 2-(1-(4-((4-(2H-tetrazol-5-yl)phenyl)amino)-5-oxo-5,6-dihydropyrimido[4,5-d]pyridazin-2-yl)piperidin-4-yl)acetonitrile |
| 246 | 2-(1-(4-((4-(4-((2H-tetrazol-5-yl)methyl)piperidin-1-yl)phenyl)amino)-5-oxo-5,6-dihydropyrimido[4,5-d]pyridazin-2-yl)piperidin-4-yl)acetonitrile |

TABLE 1-continued

| Structure | IUPAC Name |
|---|---|
| 247 | 2-(azepan-1-yl)-4-((4-(4-methylpiperazin-1-yl)phenyl)amino)pyrimido[4,5-d]pyridazin-5(6H)-one |
| 248 | 2-(1-(4-((4-(4-methylpiperazin-1-yl)phenyl)amino)-5-oxo-5,6-dihydropyrimido[4,5-d]pyridazin-2-yl)piperidin-4-yl)acetonitrile |
| 249 | 2-(1-(5-((2-(4-(cyanomethyl)piperidin-1-yl)-5-oxo-5,6-dihydropyrimido[4,5-d]pyridazin-4-yl)amino)pyridin-2-yl)piperidin-3-yl)acetic acid |

TABLE 1-continued
| Structure | IUPAC Name |
|---|---|
| 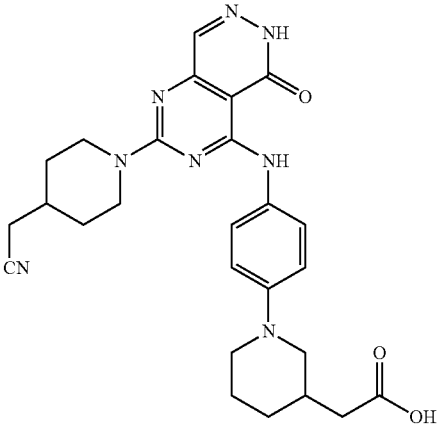 250 | 2-(1-(4-((2-(4-(cyanomethyl)piperidin-1-yl)-5-oxo-5,6-dihydropyrimido[4,5-d]pyridazin-4-yl)amino)phenyl)piperidin-3-yl)acetic acid |
| 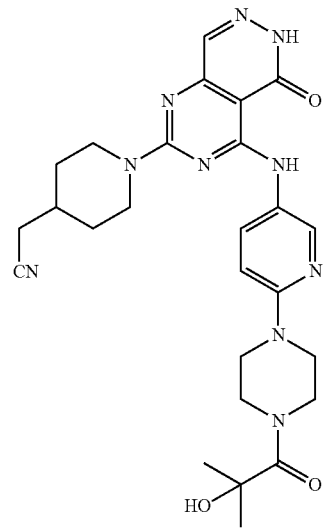 251 | 2-(1-(4-((6-(4-(2-hydroxy-2-methylpropanoyl)piperazin-1-yl)pyridin-3-yl)amino)-5-oxo-5,6-dihydropyrimido[4,5-d]pyridazin-2-yl)piperidin-4-yl)acetonitrile |
| 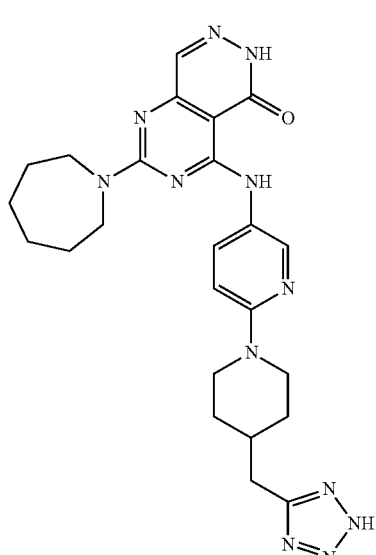 252 | 4-((6-(4-((2H-tetrazol-5-yl)methyl)piperidin-1-yl)pyridin-3-yl)amino)-2-(azepan-1-yl)pyrimido[4,5-d]pyridazin-5(6H)-one |

TABLE 1-continued
| Structure | IUPAC Name |
|---|---|
| 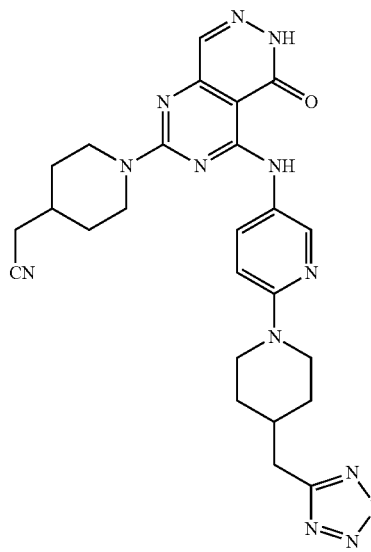 253 | 2-(1-(4-((6-(4-((2H-tetrazol-5-yl)methyl)piperidin-1-yl)pyridin-3-yl)amino)-5-oxo-5,6-dihydropyrimido[4,5-d]pyridazin-2-yl)piperidin-4-yl)acetonitrile |
| 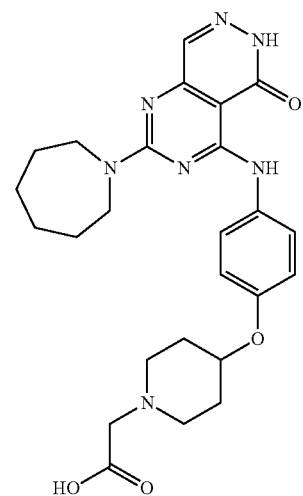 254 | 2-(4-(4-((2-(azepan-1-yl)-5-oxo-5,6-dihydropyrimido[4,5-d]pyridazin-4-yl)amino)phenoxy)piperidin-1-yl)acetic acid |

TABLE 1-continued
| Structure | IUPAC Name |
|---|---|
| 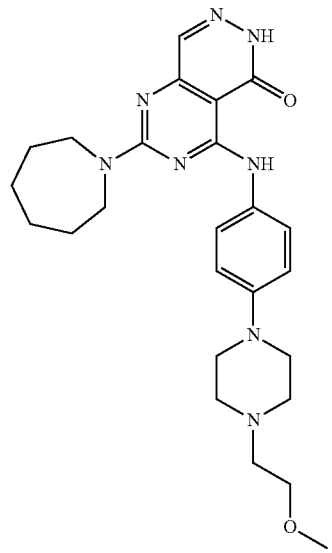 255 | 2-(azepan-1-yl)-4-((4-(4-(2-methoxyethyl)piperazin-1-yl)phenyl)amino)pyrimido[4,5-d]pyridazin-5(6H)-one |
| 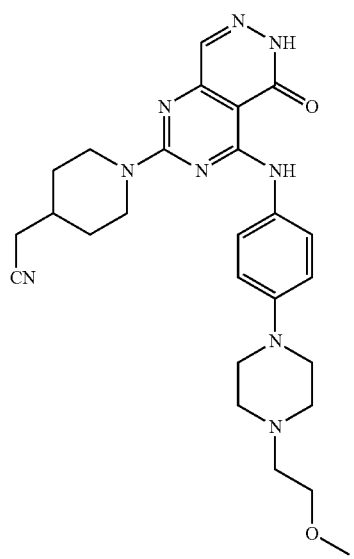 256 | 2-(1-(4-((4-(4-(2-methoxyethyl)piperazin-1-yl)phenyl)amino)-5-oxo-5,6-dihydropyrimido[4,5-d]pyridazin-2-yl)piperidin-4-yl)acetonitrile |

| Structure | IUPAC Name |
|---|---|
| 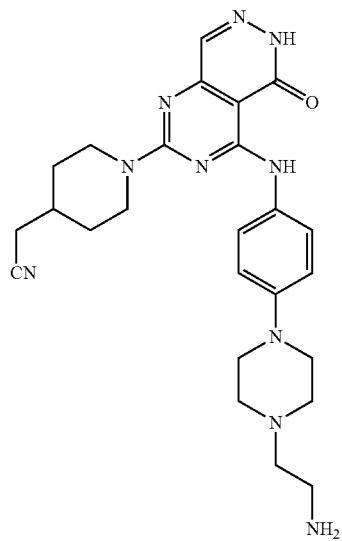 257 | 2-(1-(4-((4-(4-(2-aminoethyl)piperazin-1-yl)phenyl)amino)-5-oxo-5,6-dihydropyrimido[4,5-d]pyridazin-2-yl)piperidin-4-yl)acetonitrile |
| 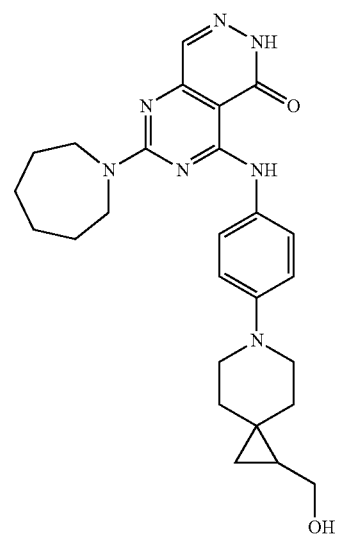 258 | 2-(azepan-1-yl)-4-((4-(1-(hydroxymethyl)-6-azaspiro[2.5]octan-6-yl)phenyl)amino)pyrimido[4,5-d]pyridazin-5(6H)-one |

| Structure | IUPAC Name |
|---|---|
| 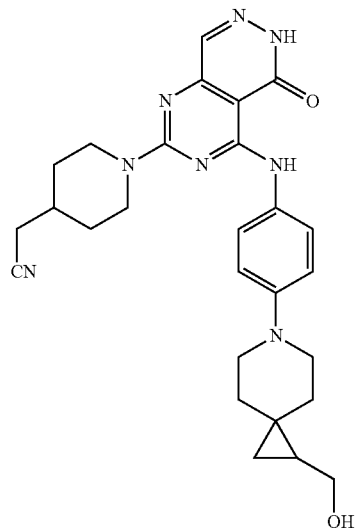<br>259 | 2-(1-(4-((4-(1-(hydroxymethyl)-6-azaspiro[2.5]octan-6-yl)phenyl)amino)-5-oxo-5,6-dihydropyrimido[4,5-d]pyridazin-2-yl)piperidin-4-yl)acetonitrile |
| 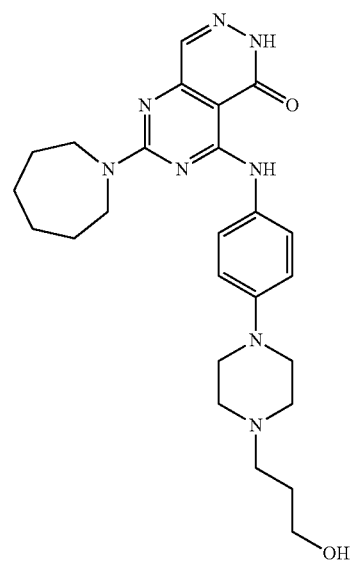<br>260 | 2-(azepan-1-yl)-4-((4-(4-(3-hydroxypropyl)piperazin-1-yl)phenyl)amino)pyrimido[4,5-d]pyridazin-5(6H)-one |

TABLE 1-continued
| Structure | IUPAC Name |
|---|---|
| 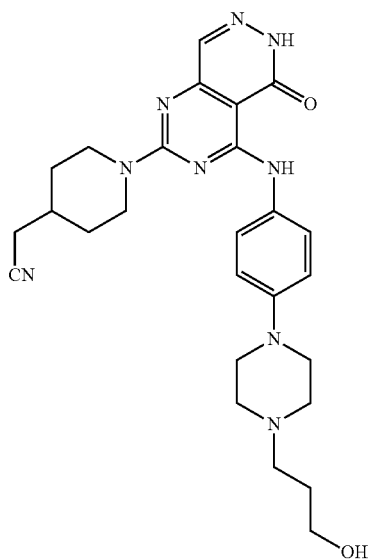
261 | 2-(1-(4-((4-(4-(3-hydroxypropyl)piperazin-1-yl)phenyl)amino)-5-oxo-5,6-dihydropyrimido[4,5-d]pyridazin-2-yl)piperidin-4-yl)acetonitrile |
| 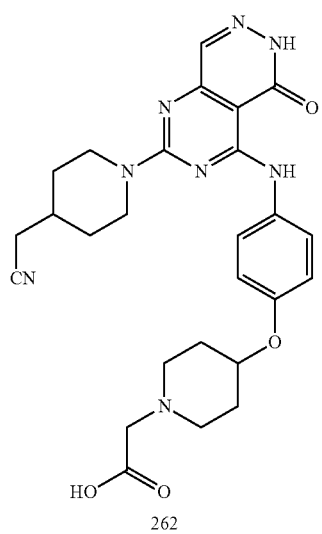 [SMILES: N#CCC1CCN(c2nc(Nc3ccc(OC4CCN(CC(=O)O)CC4)cc3)c3c(=O)[nH]ncc3n2)CC1]
262 | 2-(4-(4-((2-(4-(cyanomethyl)piperidin-1-yl)-5-oxo-5,6-dihydropyrimido[4,5-d]pyridazin-4-yl)amino)phenoxy)piperidin-1-yl)acetic acid |

TABLE 1-continued
| Structure | IUPAC Name |
|---|---|
| 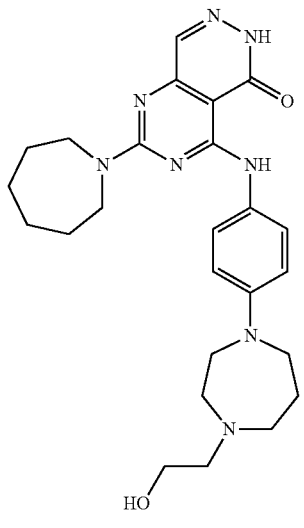 263 | 2-(azepan-1-yl)-4-((4-(4-(2-hydroxyethyl)-1,4-diazepan-1-yl)phenyl)amino)pyrimido[4,5-d]pyridazin-5(6H)-one |
| 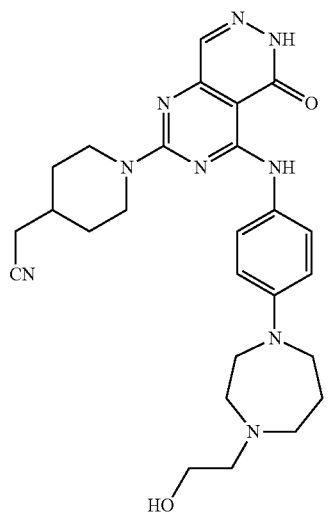 264 | 2-(1-(4-((4-(4-(2-hydroxyethyl)-1,4-diazepan-1-yl)phenyl)amino)-5-oxo-5,6-dihydropyrimido[4,5-d]pyridazin-2-yl)piperidin-4-yl)acetonitrile |

| Structure | IUPAC Name |
|---|---|
| 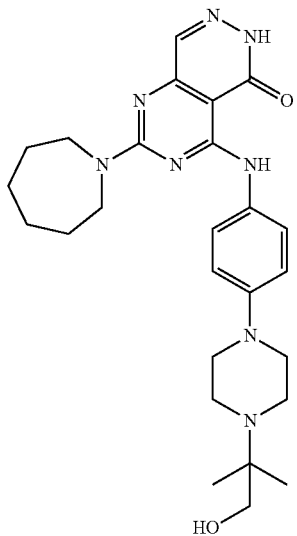 265 | 2-(azepan-1-yl)-4-((4-(4-(1-hydroxy-2-methylpropan-2-yl)piperazin-1-yl)phenyl)amino)pyrimido[4,5-d]pyridazin-5(6H)-one |
| 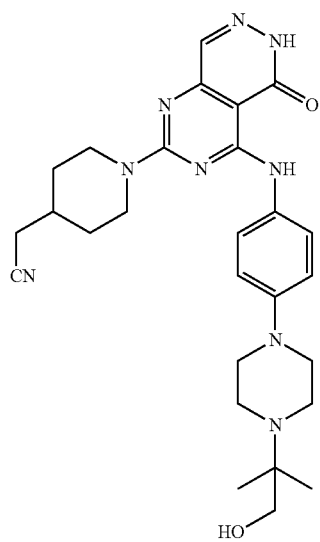 266 | 2-(1-(4-((4-(4-(1-hydroxy-2-methylpropan-2-yl)piperazin-1-yl)phenyl)amino)-5-oxo-5,6-dihydropyrimido[4,5-d]pyridazin-2-yl)piperidin-4-yl)acetonitrile |

| Structure | IUPAC Name |
|---|---|
| 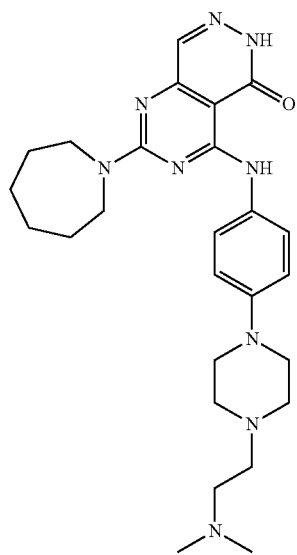 267 | 2-(azepan-1-yl)-4-((4-(4-(2-(dimethylamino)ethyl)piperazin-1-yl)phenyl)amino)pyrimido[4,5-d]pyridazin-5(6H)-one |
| 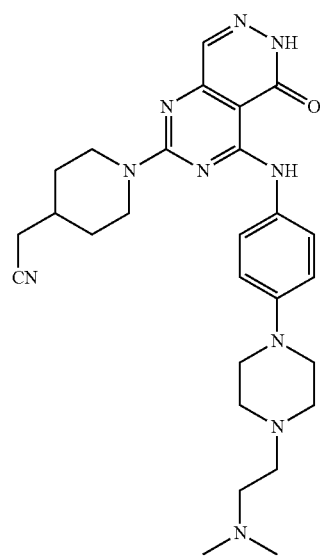 268 | 2-(1-(4-((4-(4-(2-(dimethylamino)ethyl)piperazin-1-yl)phenyl)amino)-5-oxo-5,6-dihydropyrimido[4,5-d]pyridazin-2-yl)piperidin-4-yl)acetonitrile |

TABLE 1-continued

| Structure | IUPAC Name |
|---|---|
| 269 | 2-(azepan-1-yl)-4-((4-(2-(4-ethylpiperazin-1-yl)-2-oxoethoxy)phenyl)amino)pyrimido[4,5-d]pyridazin-5(6H)-one |
| 270 | 2-(1-(4-((4-(2-(4-ethylpiperazin-1-yl)-2-oxoethoxy)phenyl)amino)-5-oxo-5,6-dihydropyrimido[4,5-d]pyridazin-2-yl)piperidin-4-yl)acetonitrile |
| 271 | 2-(1-(4-((4-(2-(4-methylpiperazin-1-yl)-2-oxoethoxy)phenyl)amino)-5-oxo-5,6-dihydropyrimido[4,5-d]pyridazin-2-yl)piperidin-4-yl)acetonitrile |

| Structure | IUPAC Name |
|---|---|
| 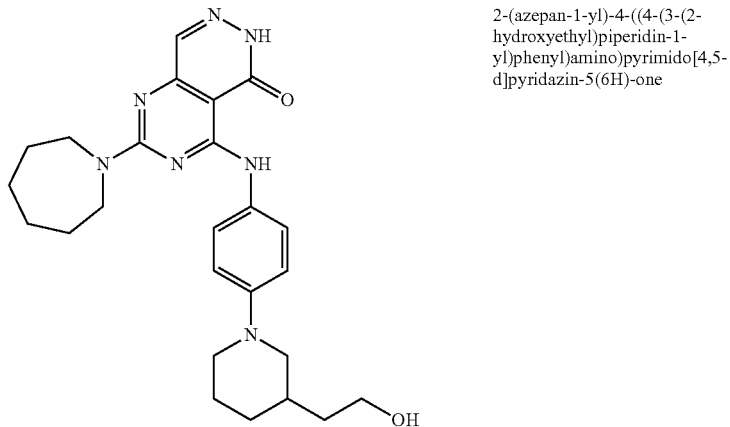<br>272 | 2-(azepan-1-yl)-4-((4-(3-(2-hydroxyethyl)piperidin-1-yl)phenyl)amino)pyrimido[4,5-d]pyridazin-5(6H)-one |
| 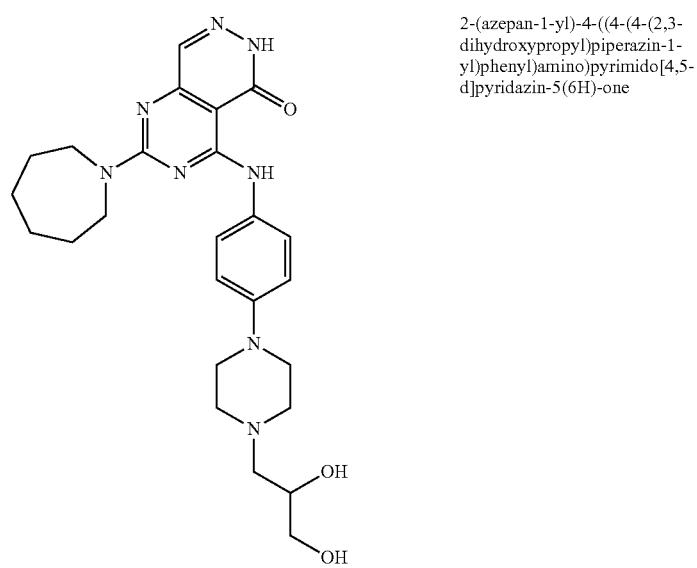<br>273 | 2-(azepan-1-yl)-4-((4-(4-(2,3-dihydroxypropyl)piperazin-1-yl)phenyl)amino)pyrimido[4,5-d]pyridazin-5(6H)-one |

TABLE 1-continued
| Structure | IUPAC Name |
|---|---|
| 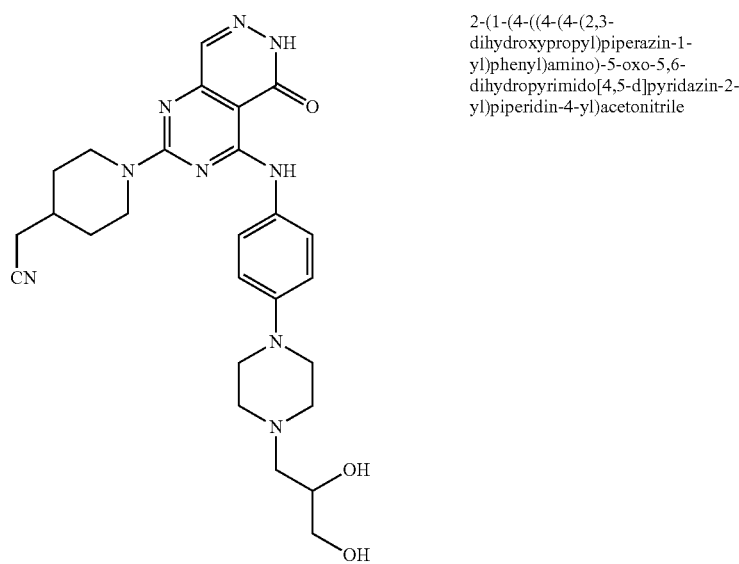 274 | 2-(1-(4-((4-(4-(2,3-dihydroxypropyl)piperazin-1-yl)phenyl)amino)-5-oxo-5,6-dihydropyrimido[4,5-d]pyridazin-2-yl)piperidin-4-yl)acetonitrile |
| 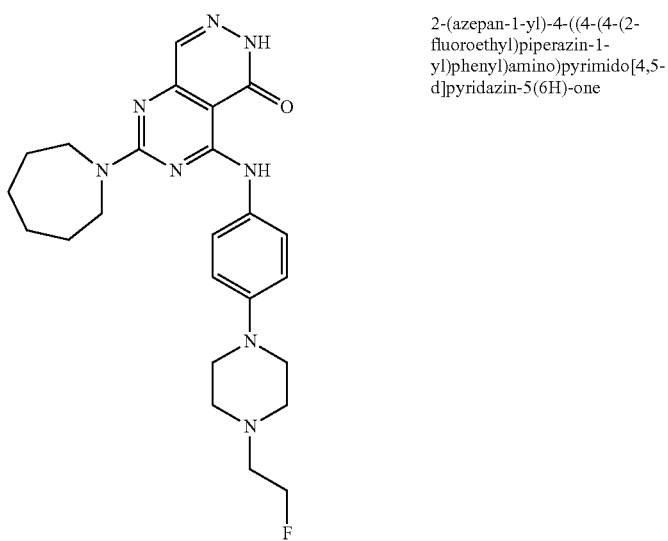 275 | 2-(azepan-1-yl)-4-((4-(4-(2-fluoroethyl)piperazin-1-yl)phenyl)amino)pyrimido[4,5-d]pyridazin-5(6H)-one |

TABLE 1-continued
| Structure | IUPAC Name |
|---|---|
| 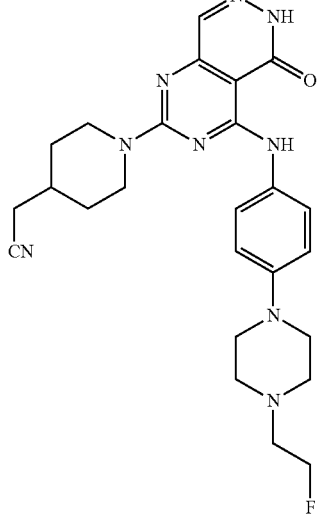 | 2-(1-(4-((4-(4-(2-fluoroethyl)piperazin-1-yl)phenyl)amino)-5-oxo-5,6-dihydropyrimido[4,5-d]pyridazin-2-yl)piperidin-4-yl)acetonitrile |
| 276 | |
| 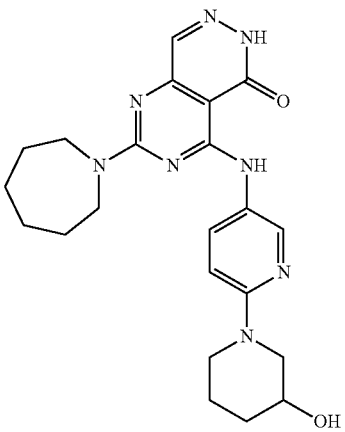 | 2-(azepan-1-yl)-4-((6-(3-hydroxypiperidin-1-yl)pyridin-3-yl)amino)pyrimido[4,5-d]pyridazin-5(6H)-one |
| 277 | |
| 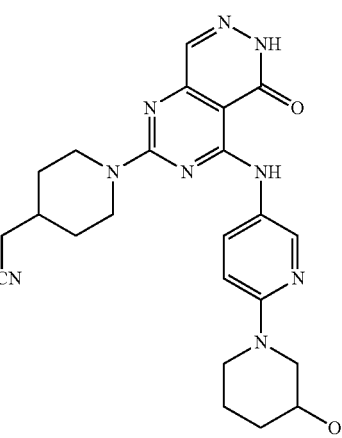 | 2-(1-(4-((6-(3-hydroxypiperidin-1-yl)pyridin-3-yl)amino)-5-oxo-5,6-dihydropyrimido[4,5-d]pyridazin-2-yl)piperidin-4-yl)acetonitrile |
| 278 | |

TABLE 1-continued
| Structure | IUPAC Name |
|---|---|
| 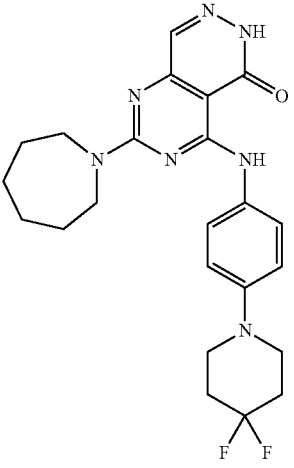 279 | 2-(azepan-1-yl)-4-((4-(4,4-difluoropiperidin-1-yl)phenyl)amino)pyrimido[4,5-d]pyridazin-5(6H)-one |
| 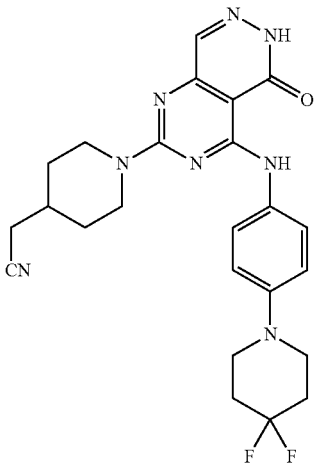 280 | 2-(1-(4-((4-(4,4-difluoropiperidin-1-yl)phenyl)amino)-5-oxo-5,6-dihydropyrimido[4,5-d]pyridazin-2-yl)piperidin-4-yl)acetonitrile |
| 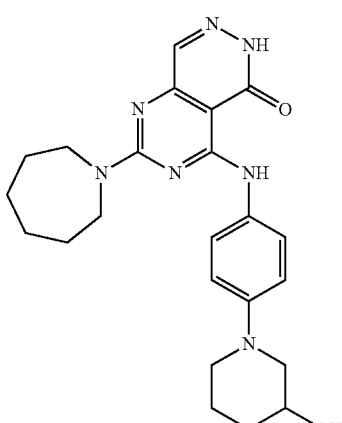 281 | 2-(azepan-1-yl)-4-((4-(3-hydroxypiperidin-1-yl)phenyl)amino)pyrimido[4,5-d]pyridazin-5(6H)-one |

TABLE 1-continued
| Structure | IUPAC Name |
|---|---|
| 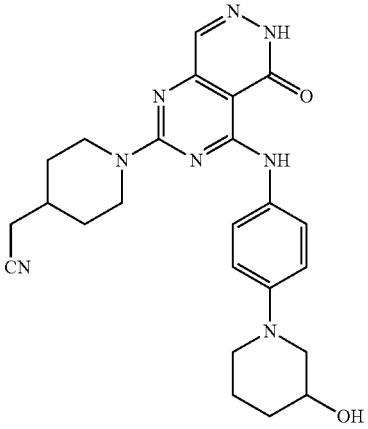 282 | 2-(1-(4-((4-(3-hydroxypiperidin-1-yl)phenyl)amino)-5-oxo-5,6-dihydropyrimido[4,5-d]pyridazin-2-yl)piperidin-4-yl)acetonitrile |
| 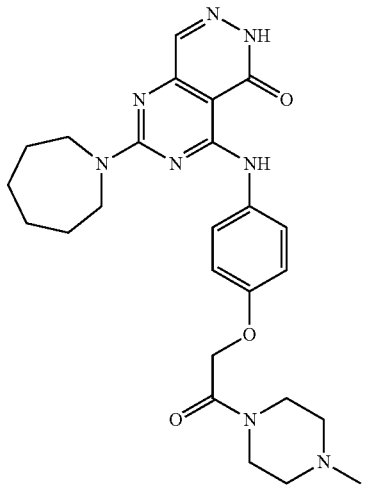 283 | 2-(azepan-1-yl)-4-((4-(2-(4-methylpiperazin-1-yl)-2-oxoethoxy)phenyl)amino)pyrimido[4,5-d]pyridazin-5(6H)-one |
| 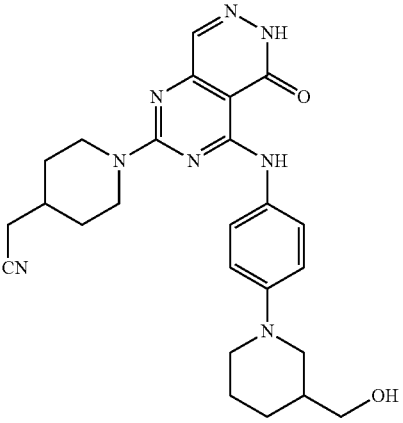 284 | 2-(1-(4-((4-(3-(hydroxymethyl)piperidin-1-yl)phenyl)amino)-5-oxo-5,6-dihydropyrimido[4,5-d]pyridazin-2-yl)piperidin-4-yl)acetonitrile |

TABLE 1-continued
| Structure | IUPAC Name |
|---|---|
| 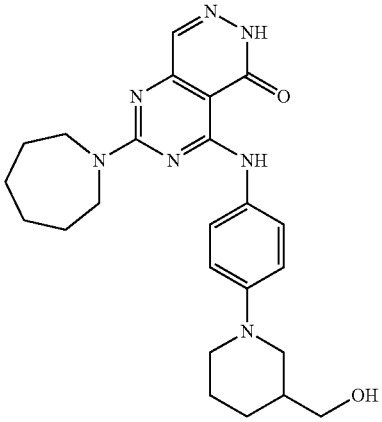 285 | 2-(azepan-1-yl)-4-((4-(3-(hydroxymethyl)piperidin-1-yl)phenyl)amino)pyrimido[4,5-d]pyridazin-5(6H)-one |
| 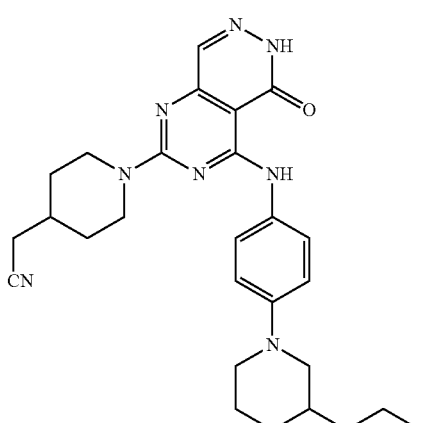 286 | 2-(1-(4-((4-(3-(2-hydroxyethyl)piperidin-1-yl)phenyl)amino)-5-oxo-5,6-dihydropyrimido[4,5-d]pyridazin-2-yl)piperidin-4-yl)acetonitrile |
| 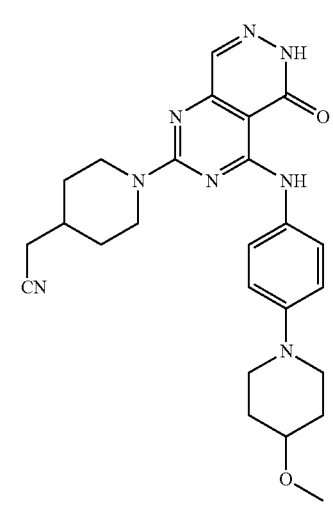 287 | 2-(1-(4-((4-(4-methoxypiperidin-1-yl)phenyl)amino)-5-oxo-5,6-dihydropyrimido[4,5-d]pyridazin-2-yl)piperidin-4-yl)acetonitrile |

TABLE 1-continued
| Structure | IUPAC Name |
|---|---|
| 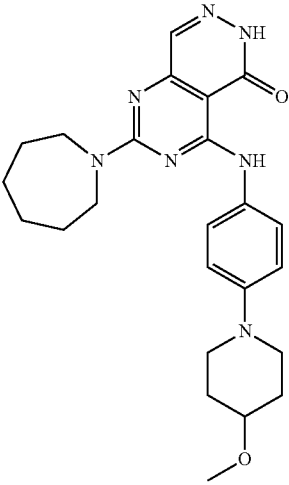 288 | 2-(azepan-1-yl)-4-((4-(4-methoxypiperidin-1-yl)phenyl)amino)pyrimido[4,5-d]pyridazin-5(6H)-one |
| 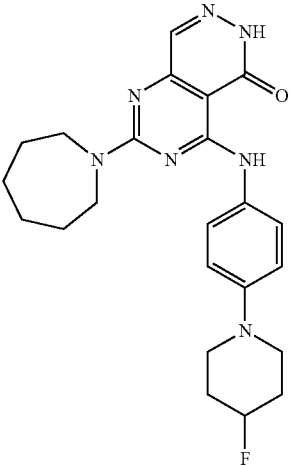 289 | 2-(azepan-1-yl)-4-((4-(4-fluoropiperidin-1-yl)phenyl)amino)pyrimido[4,5-d]pyridazin-5(6H)-one |
| 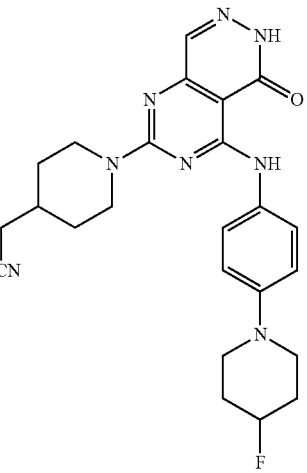 290 | 2-(1-(4-((4-(4-fluoropiperidin-1-yl)phenyl)amino)-5-oxo-5,6-dihydropyrimido[4,5-d]pyridazin-2-yl)piperidin-4-yl)acetonitrile |

TABLE 1-continued
| Structure | IUPAC Name |
|---|---|
| 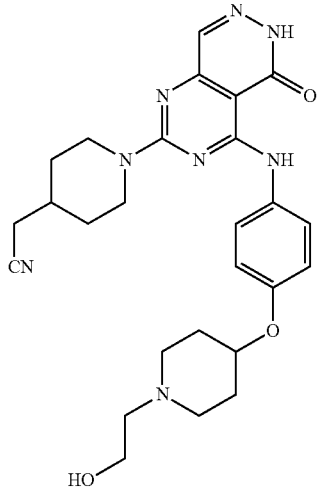 291 | 2-(1-(4-((4-((1-(2-hydroxyethyl)piperidin-4-yl)oxy)phenyl)amino)-5-oxo-5,6-dihydropyrimido[4,5-d]pyridazin-2-yl)piperidin-4-yl)acetonitrile |
| 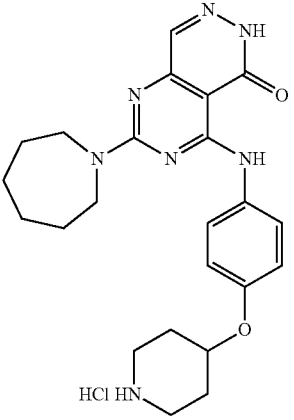 292 | 2-(azepan-1-yl)-4-((4-(piperidin-4-yloxy)phenyl)amino)pyrimido[4,5-d]pyridazin-5(6H)-one hydrochloride |
| 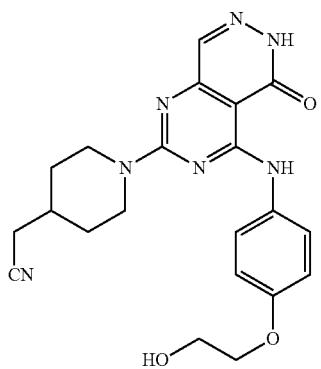 293 | 2-(1-(4-((4-(2-hydroxyethoxy)phenyl)amino)-5-oxo-5,6-dihydropyrimido[4,5-d]pyridazin-2-yl)piperidin-4-yl)acetonitrile |

TABLE 1-continued
| Structure | IUPAC Name |
|---|---|
| 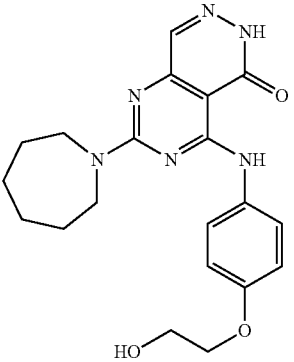 294 | 2-(azepan-1-yl)-4-((4-(2-hydroxyethoxy)phenyl)amino)pyrimido[4,5-d]pyridazin-5(6H)-one |
| 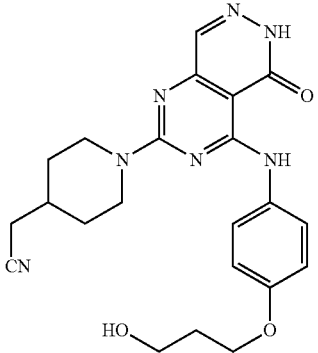 295 | 2-(1-(4-((4-(3-hydroxypropoxy)phenyl)amino)-5-oxo-5,6-dihydropyrimido[4,5-d]pyridazin-2-yl)piperidin-4-yl)acetonitrile |
| 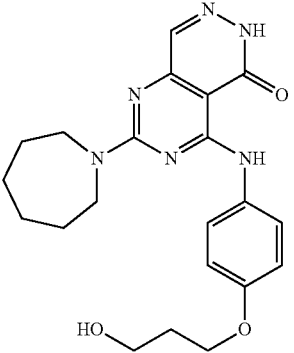 296 | 2-(azepan-1-yl)-4-((4-(3-hydroxypropoxy)phenyl)amino)pyrimido[4,5-d]pyridazin-5(6H)-one |

TABLE 1-continued
| Structure | IUPAC Name |
|---|---|
| 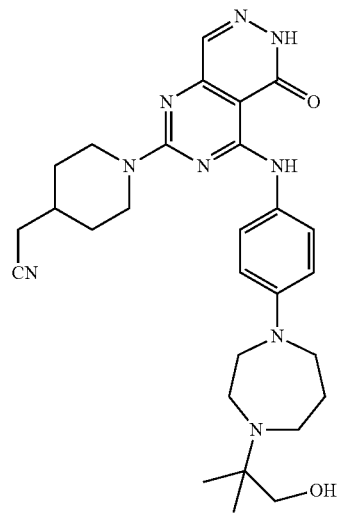 297 | 2-(1-(4-((4-(4-(1-hydroxy-2-methylpropan-2-yl)-1,4-diazepan-1-yl)phenyl)amino)-5-oxo-5,6-dihydropyrimido[4,5-d]pyridazin-2-yl)piperidin-4-yl)acetonitrile |
| 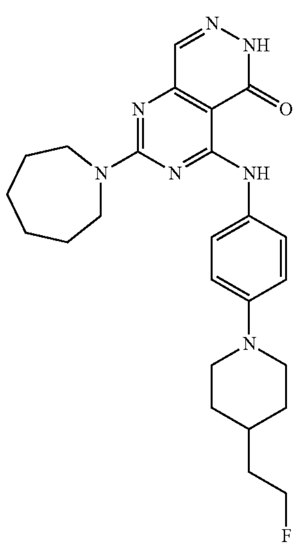 | 2-(azepan-1-yl)-4-((4-(4-(2-fluoroethyl)piperidin-1-yl)phenyl)amino)pyrimido[4,5-d]pyridazin-5(6H)-one |
| 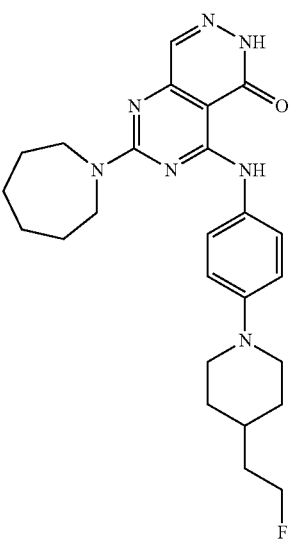 298 |  |

TABLE 1-continued
| Structure | IUPAC Name |
|---|---|
| 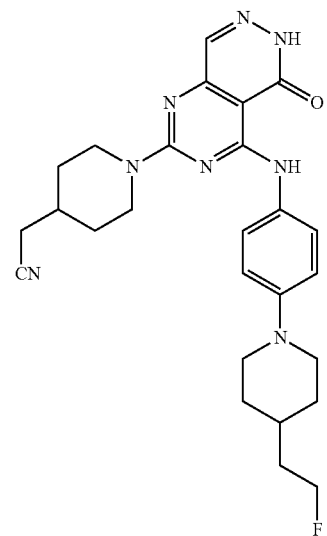 299 | 2-(1-(4-((4-(4-(2-fluoroethyl)piperidin-1-yl)phenyl)amino)-5-oxo-5,6-dihydropyrimido[4,5-d]pyridazin-2-yl)piperidin-4-yl)acetonitrile |
| 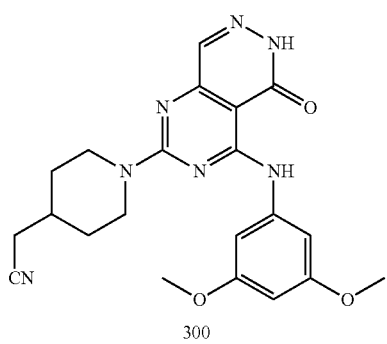 [SMILES: COc1cc(Nc2nc(N3CCC(CC#N)CC3)nc3cn[nH]c(=O)c23)cc(OC)c1] 300 | 2-(1-(4-((3,5-dimethoxyphenyl)amino)-5-oxo-5,6-dihydropyrimido[4,5-d]pyridazin-2-yl)piperidin-4-yl)acetonitrile |
| 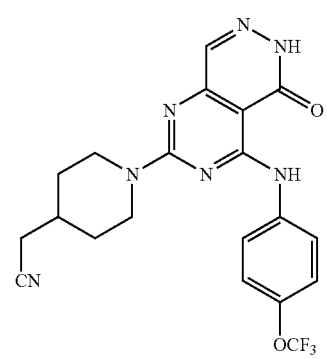 301 | 2-(1-(5-oxo-4-((4-(trifluoromethoxy)phenyl)amino)-5,6-dihydropyrimido[4,5-d]pyridazin-2-yl)piperidin-4-yl)acetonitrile |

TABLE 1-continued
| Structure | IUPAC Name |
|---|---|
| 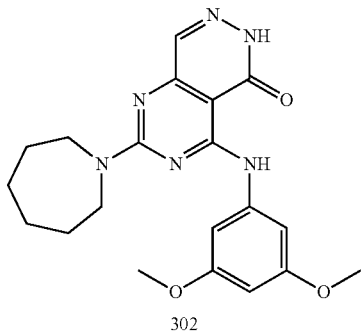 [SMILES: COc1cc(Nc2nc(N3CCCCCC3)nc3cn[nH]c(=O)c23)cc(OC)c1] 302 | 2-(azepan-1-yl)-4-((3,5-dimethoxyphenyl)amino)pyrimido[4,5-d]pyridazin-5(6H)-one |
| 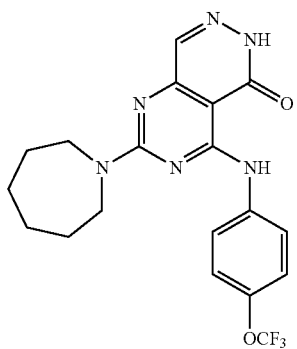 303 | 2-(azepan-1-yl)-4-((4-(trifluoromethoxy)phenyl)amino)pyrimido[4,5-d]pyridazin-5(6H)-one |
| 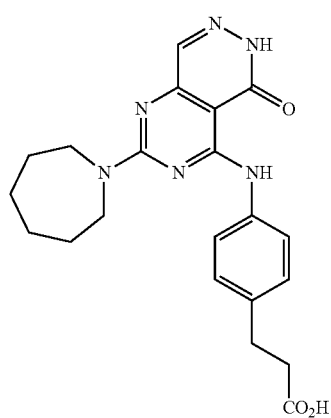 304 | 3-(4-((2-(azepan-1-yl)-5-oxo-5,6-dihydropyrimido[4,5-d]pyridazin-4-yl)amino)phenyl)propanoic acid |

TABLE 1-continued
| Structure | IUPAC Name |
|---|---|
| 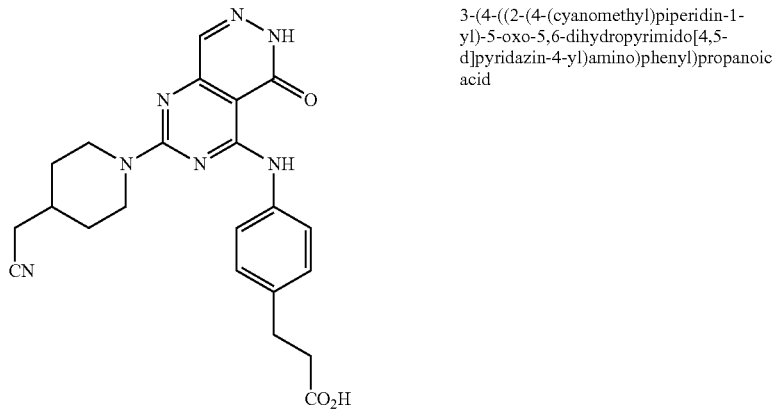<br>305 | 3-(4-((2-(4-(cyanomethyl)piperidin-1-yl)-5-oxo-5,6-dihydropyrimido[4,5-d]pyridazin-4-yl)amino)phenyl)propanoic acid |
| 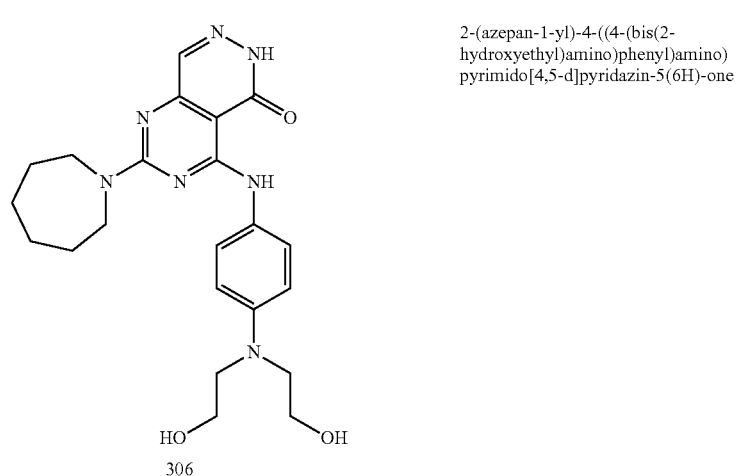<br>306 | 2-(azepan-1-yl)-4-((4-(bis(2-hydroxyethyl)amino)phenyl)amino)pyrimido[4,5-d]pyridazin-5(6H)-one |
| 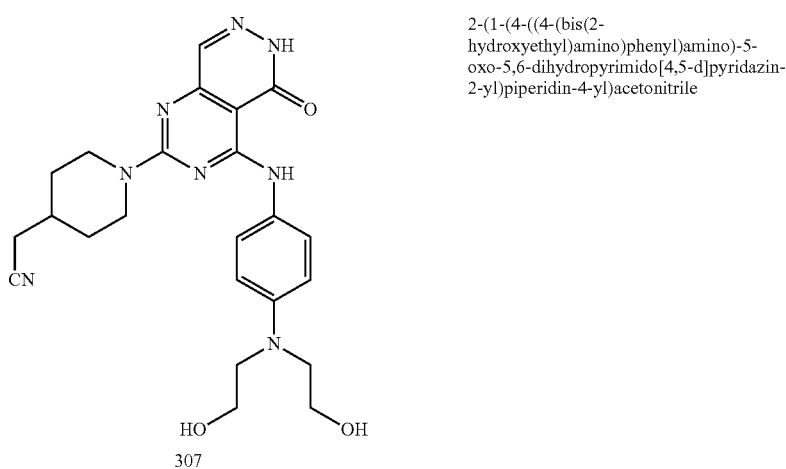<br>307 | 2-(1-(4-((4-(bis(2-hydroxyethyl)amino)phenyl)amino)-5-oxo-5,6-dihydropyrimido[4,5-d]pyridazin-2-yl)piperidin-4-yl)acetonitrile |

TABLE 1-continued

| Structure | IUPAC Name |
| --- | --- |
| 308 | 2-(azepan-1-yl)-4-((4-(3-hydroxypropyl)phenyl)amino)pyrimido[4,5-d]pyridazin-5(6H)-one |
| 309 | 2-(1-(4-((4-(3-hydroxypropyl)phenyl)amino)-5-oxo-5,6-dihydropyrimido[4,5-d]pyridazin-2-yl)piperidin-4-yl)acetonitrile |
| 310 | 2-(azepan-1-yl)-4-((3-(hydroxymethyl)phenyl)amino)pyrimido[4,5-d]pyridazin-5(6H)-one |
| 311 | 2-(1-(4-((3-(hydroxymethyl)phenyl)amino)-5-oxo-5,6-dihydropyrimido[4,5-d]pyridazin-2-yl)piperidin-4-yl)acetonitrile |

TABLE 1-continued
| Structure | IUPAC Name |
|---|---|
| 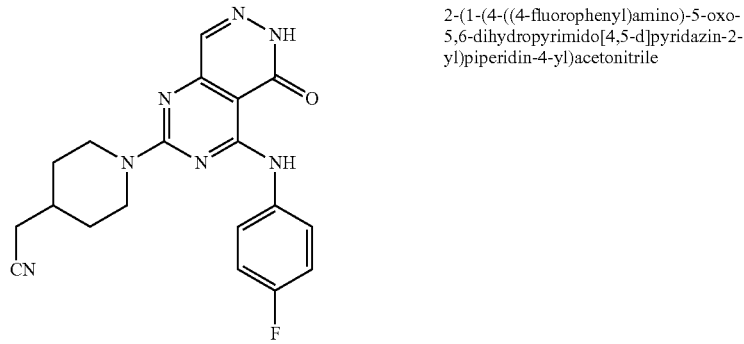 312 | 2-(1-(4-((4-fluorophenyl)amino)-5-oxo-5,6-dihydropyrimido[4,5-d]pyridazin-2-yl)piperidin-4-yl)acetonitrile |
| 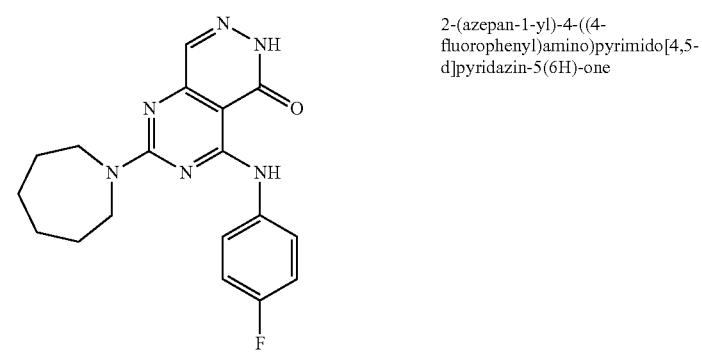 313 | 2-(azepan-1-yl)-4-((4-fluorophenyl)amino)pyrimido[4,5-d]pyridazin-5(6H)-one |
| 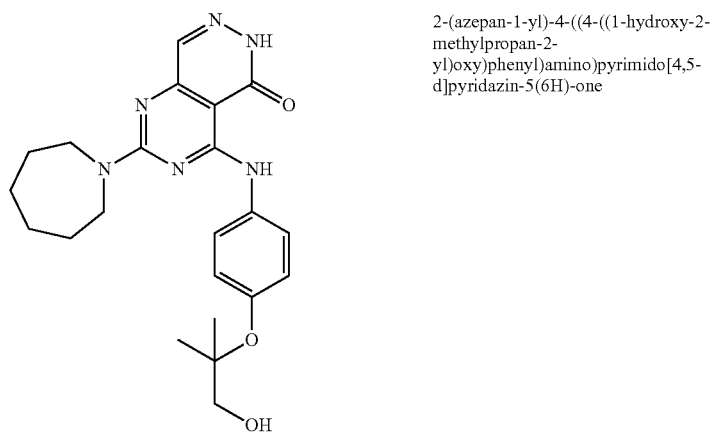 314 | 2-(azepan-1-yl)-4-((4-((1-hydroxy-2-methylpropan-2-yl)oxy)phenyl)amino)pyrimido[4,5-d]pyridazin-5(6H)-one |

TABLE 1-continued
| Structure | IUPAC Name |
|---|---|
| 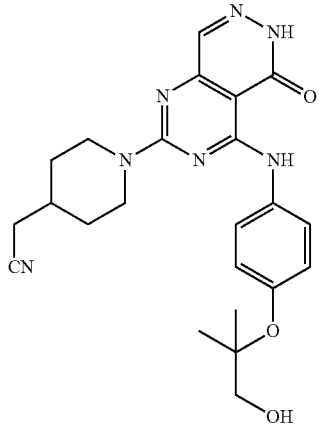 315 | 2-(1-(4-((4-((1-hydroxy-2-methylpropan-2-yl)oxy)phenyl)amino)-5-oxo-5,6-dihydropyrimido[4,5-d]pyridazin-2-yl)piperidin-4-yl)acetonitrile |
| 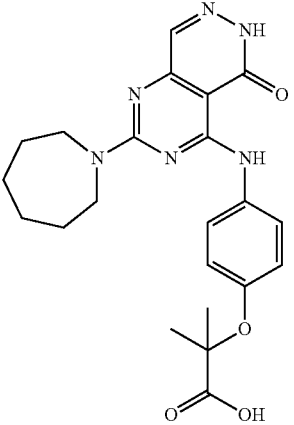 316 | 2-(4-((2-(azepan-1-yl)-5-oxo-5,6-dihydropyrimido[4,5-d]pyridazin-4-yl)amino)phenoxy)-2-methylpropanoic acid |
| 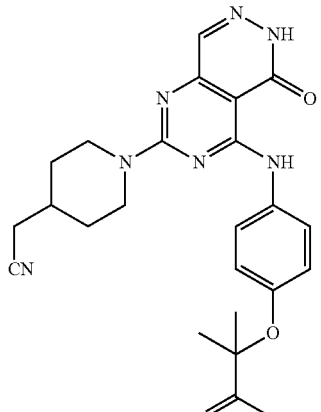 317 | 2-(4-((2-(4-(cyanomethyl)piperidin-1-yl)-5-oxo-5,6-dihydropyrimido[4,5-d]pyridazin-4-yl)amino)phenoxy)-2-methylpropanoic acid |

TABLE 1-continued

| Structure | IUPAC Name |
|---|---|
| 318 | 2-(azepan-1-yl)-4-((3,4-dimethoxyphenyl)amino)pyrimido[4,5-d]pyridazin-5(6H)-one |
| 319 | 2-(1-(4-((3,4-dimethoxyphenyl)amino)-5-oxo-5,6-dihydropyrimido[4,5-d]pyridazin-2-yl)piperidin-4-yl)acetonitrile |
| 320 | 2-(azepan-1-yl)-4-((3-methoxyphenyl)amino)pyrimido[4,5-d]pyridazin-5(6H)-one |
| 321 | 2-(1-(4-((3-methoxyphenyl)amino)-5-oxo-5,6-dihydropyrimido[4,5-d]pyridazin-2-yl)piperidin-4-yl)acetonitrile |

TABLE 1-continued
| Structure | IUPAC Name |
|---|---|
| 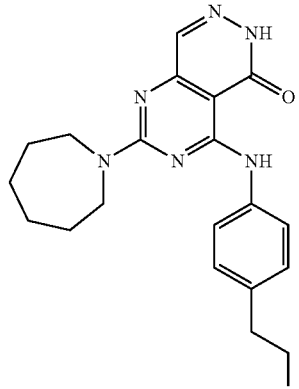 322 | 2-(azepan-1-yl)-4-((4-(2-hydroxyethyl)phenyl)amino)pyrimido[4,5-d]pyridazin-5(6H)-one |
| 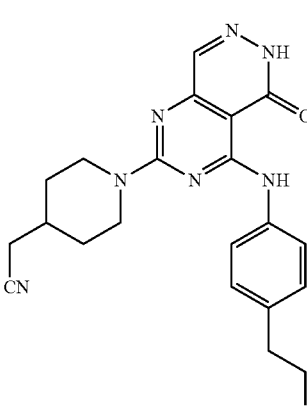 323 | 2-(1-(4-((4-(2-hydroxyethyl)phenyl)amino)-5-oxo-5,6-dihydropyrimido[4,5-d]pyridazin-2-yl)piperidin-4-yl)acetonitrile |
| 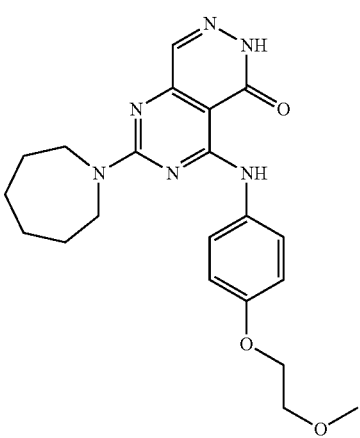 324 | 2-(azepan-1-yl)-4-((4-(2-methoxyethoxy)phenyl)amino)pyrimido[4,5-d]pyridazin-5(6H)-one |

TABLE 1-continued
| Structure | IUPAC Name |
|---|---|
| 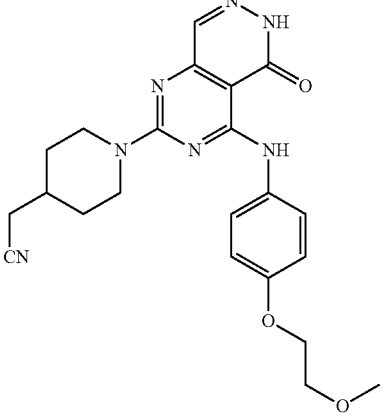 325 | 2-(1-(4-((4-(2-methoxyethoxy)phenyl)amino)-5-oxo-5,6-dihydropyrimido[4,5-d]pyridazin-2-yl)piperidin-4-yl)acetonitrile |
| 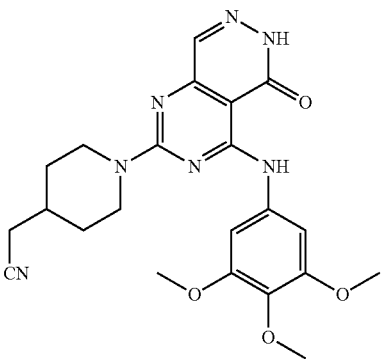 326 | 2-(1-(5-oxo-4-((3,4,5-trimethoxyphenyl)amino)-5,6-dihydropyrimido[4,5-d]pyridazin-yl)piperidin-4-yl)acetonitrile |
| 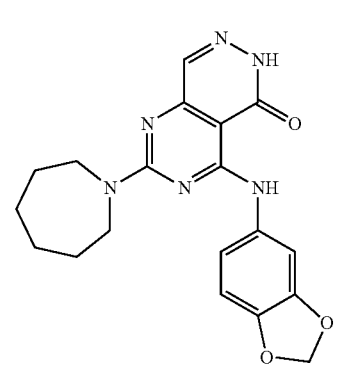 327 | 2-(azepan-1-yl)-4-(benzo[d][1,3]dioxol-5-ylamino)pyrimido[4,5-d]pyridazin-5(6H)-one |

TABLE 1-continued
| Structure | IUPAC Name |
|---|---|
| 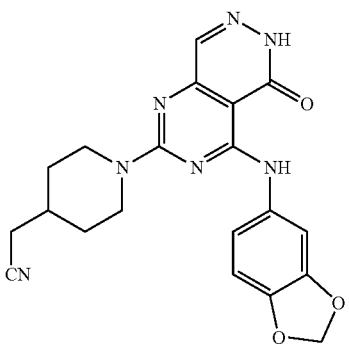 328 | 2-(1-(4-(benzo[d][1,3]dioxol-5-ylamino)-5-oxo-5,6-dihydropyrimido[4,5-d]pyridazin-2-yl)piperidin-4-yl)acetonitrile |
| 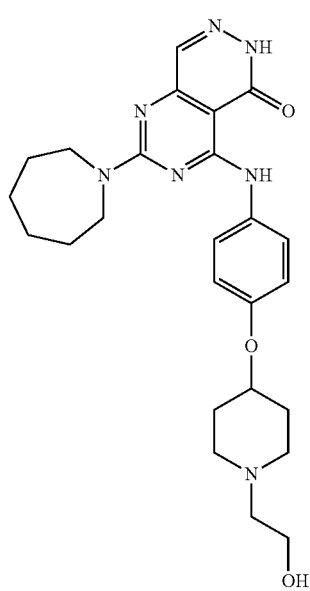 329 | 2-(azepan-1-yl)-4-((4-((1-(2-hydroxyethyl)piperidin-4-yl)oxy)phenyl)amino)pyrimido[4,5-d]pyridazin-5(6H)-one |
| 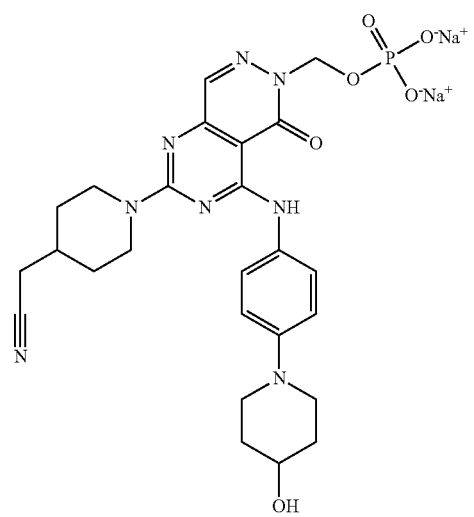 330 | sodium (2-(4-(cyanomethyl)piperidin-1-yl)-4-((4-(4-hydroxypiperidin-1-yl)phenyl)amino)-5-oxopyrimido[4,5-d]pyridazin-6(5H)-yl)methyl phosphate |

TABLE 1-continued
| Structure | IUPAC Name |
|---|---|
| 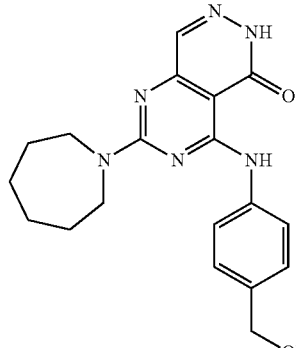 331 | 2-(azepan-1-yl)-4-((4-(hydroxymethyl)phenyl)amino)pyrimido[4,5-d]pyridazin-5(6H)-one |
| 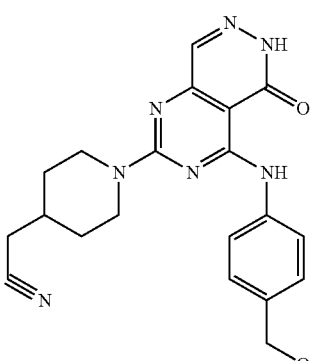 332 | 2-(1-(4-((4-(hydroxymethyl)phenyl)amino)-5-oxo-5,6-dihydropyrimido[4,5-d]pyridazin-2-yl)piperidin-4-yl)acetonitrile |
| 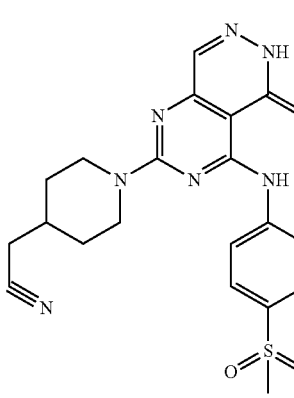 333 | 2-(1-(4-((4-(methylsulfonyl)phenyl)amino)-5-oxo-5,6-dihydropyrimido[4,5-d]pyridazin-2-yl)piperidin-4-yl)acetonitrile |

TABLE 1-continued
| Structure | IUPAC Name |
|---|---|
| 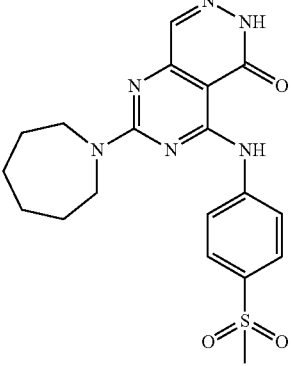 334 | 2-(azepan-1-yl)-4-((4-(methylsulfonyl)phenyl)amino)pyrimido[4,5-d]pyridazin-5(6H)-one |
| 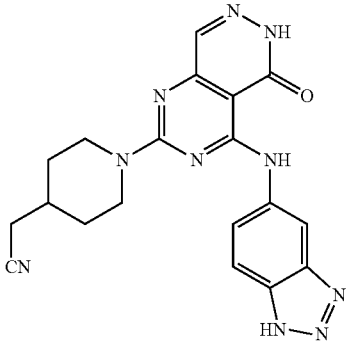 335 | 2-(1-(4-((1H-benzo[d][1,2,3]triazol-5-yl)amino)-5-oxo-5,6-dihydropyrimido[4,5-d]pyridazin-2-yl)piperidin-4-yl)acetonitrile |
| 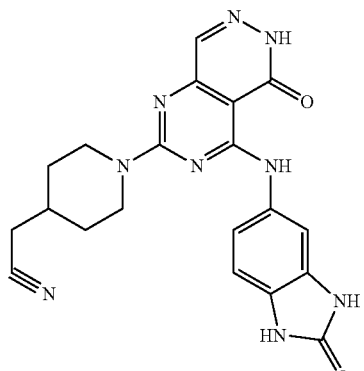 336 | 2-(1-(5-oxo-4-((2-oxo-2,3-dihydro-1H-benzo[d]imidazol-5-yl)amino)-5,6-dihydropyrimido[4,5-d]pyridazin-2-yl)piperidin-4-yl)acetonitrile |

TABLE 1-continued

| Structure | IUPAC Name |
|---|---|
| 337 | 2-(1-(4-((4-(3-fluoropropyl)phenyl)amino)-5-oxo-5,6-dihydropyrimido[4,5-d]pyridazin-2-yl)piperidin-4-yl)acetonitrile |
| 338 | 2-(1-(4-((4-(difluoromethoxy)phenyl)amino)-5-oxo-5,6-dihydropyrimido[4,5-d]pyridazin-2-yl)piperidin-4-yl)acetonitrile |
| 339 | 4-((1H-benzo[d][1,2,3]triazol-5-yl)amino)-2-(azepan-1-yl)pyrimido[4,5-d]pyridazin-5(6H)-one |

Methods of preparing compounds of Formula (I), as well as methods of preparing specific compounds set forth in Table 1, are disclosed in U.S. Pat. No. 8,729,079 B2.

To practice the inventive methods, the compound of formula (I) may be appropriately formulated into a desired dosage form, alone (neat) or optionally with other pharmaceutically inert or inactive ingredients. It may be used alone or in a composition suitable for in vitro applications. In one embodiment, the pharmaceutically inert or inactive ingredient includes one or more pharmaceutically acceptable carriers or excipients. The present invention also contemplates combining the compound of Formula (I) with one or more therapeutic agents, e.g., anti-cancer agents (e.g., in the same dosage form or in the same treatment regimen). In a further embodiment, a compound of Formula (I) may be combined with one or more inert/inactive ingredients and one or more therapeutic agents.

The pharmaceutical compositions of the invention contain an amount of a compound of Formula (I) that is effective for treating cancer in a subject, or inhibiting growth and proliferation of cancer cells (in vivo or in vitro) or inhibiting tumor growth (which may be referred to collectively as an "anti-cancer effect"). Specifically, the dosage of the compound of Formula (I) to achieve a therapeutic effect (as described herein) may depend on factors such as the formulation, pharmacological potency of the drug, age, weight and sex of the patient, condition being treated, severity of the patient's symptoms, specific compound of Formula (I), and route of delivery. Dosages may be adjusted depending, for example, on the response pattern of the patient. It is also contemplated that the treatment and dosage of the compound of Formula (I) may be administered in unit dosage form and that one skilled in the art would adjust the unit dosage form accordingly to reflect the relative level of activity. The decision as to the particular dosage to be employed (and the number of times to be administered per day) is within the discretion of the ordinarily-skilled physician, and may be varied by titration of the dosage to the particular circumstances to produce the desired therapeutic effect. The effective amount of the compound of formula (I) to achieve an anti-cancer effect in a patient may range from about 1 to about 1000 mg daily dose, and in some embodiments from about 5 to about 500 mg daily dose, and in some other embodiments, from about 10 to about 100 mg daily dose.

The therapeutically effective amounts may be provided on regular schedule, i.e., on a less than daily, daily, weekly, monthly, or yearly basis or on an irregular schedule with varying administration days, weeks, months, etc. Alternatively, the therapeutically effective amount to be administered may vary. In one embodiment, the therapeutically effective amount for the first dose may be higher than the therapeutically effective amount for one or more of the subsequent doses. In another embodiment, the therapeutically effective amount for the first dose may be lower than the therapeutically effective amount for one or more of the subsequent doses. Equivalent dosages may be administered over various time periods including, for example, about every 2 hours, about every 6 hours, about every 8 hours, about every 12 hours, about every 24 hours, about every 36 hours, about every 48 hours, about every 72 hours, about every week, about every 2 weeks, about every 3 weeks, about every month, about every 2 months, about every 3 months and about every 6 months. The number and frequency of dosages corresponding to a completed course of anti-cancer therapy will be determined according to the judgment of a health-care practitioner. The therapeutically effective amounts described herein refer to total amounts administered for a given time period such that if more than one compound of Formula (I) is administered, the therapeutically effective amounts correspond to the total amount administered.

The compound of Formula (I) may be administered by any medically acceptable route, taking into consideration the specific cancerous condition for which it has been selected. The compounds of Formula (I) may be delivered orally, by injection (including intravascularly, e.g., intravenously or intra-arterially), inhalation (intranasally and intratracheally), ocularly, transdermally (via simple passive diffusion formulations or via facilitated delivery using, for example, iontophoresis, microporation with microneedles, radio-frequency ablation or the like), intravascularly, subcutaneously, intramuscularly, sublingually, intracranially, epidurally, rectally, and vaginally, among other routes. In some embodiments, the compound of Formula (I) may be administered by injection, orally or topically.

The compound of Formula (I) may be administered alone, i.e., neat. It may also be administered as a formulation that also contains a pharmaceutically acceptable carrier and/or excipient (collectively referred to as a "carrier". The amount of the pharmaceutical carrier is determined by factors that may include the solubility and chemical nature of the compound of Formula (I), chosen route of administration, and standard pharmacological practice. The carriers may be in dry (solid) or liquid form. Liquid pharmaceutical compositions are typically sterile solutions or suspensions. When liquid carriers are utilized for parenteral administration, they are desirably sterile liquids. Liquid carriers are typically utilized in preparing solutions, suspensions, emulsions, syrups and elixirs. A variety of suitable liquid carriers is known and may be readily selected by one of skill in the art. Such carriers may include, e.g., dimethylsulfoxide (DMSO), saline, buffered saline, cyclodextrin, hydroxypropylcyclodextrin (HPβCD), n-dodecyl-β-D-maltoside (DDM) and mixtures thereof. In one embodiment, the compound of Formula (I) is dissolved a liquid carrier. In another embodiment, the compound of Formula (I) is suspended in a liquid carrier. One of skill in the art of formulations would be able to select a suitable liquid carrier, depending on the route of administration. The compound of Formula (I) may alternatively be formulated in a solid carrier of which a variety of solid carriers and excipients are known to those of skill in the art. In one embodiment, the composition may be compacted into a unit dose form, i.e., tablet or caplet. In another embodiment, the composition may be added to unit dose form, i.e., a capsule. In a further embodiment, the composition may be formulated for administration as a powder. The solid carrier may perform a variety of functions, i.e., may perform the functions of two or more of the excipients described below. For example, a solid carrier may also act as a flavoring agent, diluent, lubricant, solubilizer, suspending agent, filler, glidant, compression aid, binder, disintegrant, or encapsulating material.

Further examples of carriers include adjuvants, antioxidants, binders, buffers, coatings, coloring agents, compression aids, emulsifiers (e.g., polyoxyethylene fatty acid esters), emollients, encapsulating materials, fillers, granulating agents, metal chelators, osmo-regulators, pH adjustors (e.g., sodium hydroxide), preservatives, sorbents, stabilizing agents, suspending agents, syrups, penetration enhancers (e.g., hydroxypolyethoxydodecane, DMSO, DMAC, DDM, etc.) and thickening agents (e.g., carboxypolymethylene or hydroxypropylmethylcellulose) and other viscosity regulators. See, for example, the excipients described in the "Handbook of Pharmaceutical Excipients", $5^{th}$ Edition, Eds.: Rowe, Sheskey, and Owen, APhA Publications (Washington, D.C.), Dec. 14, 2005.

The compound of formula (I) may be formulated to achieve a modified-release. "Modified-release" as used herein refers to delivery of a compound of Formula (I) which is controlled, for example over a period of time, e.g., at least about 8 hours (e.g., extended delivery) to at least about 12 hours (e.g., sustained delivery). Otherwise, the formulations of the present invention may permit immediate release (e.g., therapeutic levels achieved in under about 1 hour, or in less than about 2 hours).

The inventive methods may entail administering to a subject or contacting cancer cells or a tumor in need thereof a therapeutically effective amount of a compound of formula (I). As used herein, the term "cancer" refers to or describes the physiological condition in subjects in which a population of cells is characterized by unregulated cell growth. As used herein, the term "subject" refers to any animal (e.g., a mammal), including, for example, humans, non-human primates (e.g., monkeys, chimpanzees, baboons and gorillas), domestic animals (e.g., dogs and cats), rodents (e.g., mice, rats and guinea pigs), livestock (e.g., cows and swine), equines and the like, which is to be the recipient of a particular treatment or protocol described herein. Typically, the terms "subject" and "patient" are used interchangeably herein in reference to a subject that is a human subject. In one embodiment, the mammal to be treated is human. In some embodiments, the cancer patient (e.g., human cancer patient) has not been diagnosed with inflammation associated with or as a side effect of the cancer.

As used herein, the terms "treat" and "treatment" refer to therapeutic treatment, including prophylactic or preventative measures, wherein the object is to prevent or slow down (lessen) an undesired physiological change associated with cancer. Beneficial or desired clinical results of the treating may include inhibition of growth and proliferation of cancer cells or inhibition of tumor growth. Such results may also include diminishment of the extent of a disease or condition, stabilization of a disease or condition (i.e., where the disease or condition does not worsen), delay or slowing of the progression of a disease or condition, amelioration or palliation of the disease or condition, and remission (whether partial or total) of the disease or condition, whether detectable or undetectable. Such results may further include prolonging survival as compared to expected survival if not receiving treatment. Those in need of treatment include those already with the disease or condition as well as those prone to having the disease or condition or those in which the disease or condition is to be prevented. By "contacting", it is meant administering to a cancer subject or otherwise bringing a compound of formula (I) into contact with a tumor or a cancer cell (e.g., which cancer cell may be in vivo or in vitro) such that it can exert its intended effect.

Any of the methods provided herein may be used to treat cancer, cancer cells or tumors at any stage of development. Such stages include an advanced stage, a locally advanced stage, early stage cancer, progressive cancer, cancer in remission, relapsed cancer, and cancer that has proven refractory to other treatment (such as FDA-approved treatment). Accordingly, therapy may be "first-line", i.e., as an initial treatment in patients who have undergone no prior anti-cancer treatment regimens, either alone or in combination with other treatments; or "second-line", as a treatment in patients who have undergone a prior anti-cancer treatment regimen, either alone or in combination with other treatments; or as "third-line", "fourth-line", etc. treatments, either alone or in combination with other treatments. Therapy may also be given to patients who have had previous treatments which have been partially successful but are intolerant to the particular treatment. Therapy may also be given as an adjuvant treatment, i.e., to prevent reoccurrence of cancer in patients with no currently detectable disease or after surgical removal of tumor.

Cancers, cancer cells and tumors treatable in accordance with the methods of the present invention may include, by way of example, primary tumors and secondary or metastatic tumors (including those metastasized from lung, breast, or prostate), as well as recurrent or refractory tumors. Recurrent tumors encompass tumors that appear to be inhibited by treatment with such agents, but recur up to five years, sometimes up to ten years or longer after treatment is discontinued. Refractory tumors are tumors that have failed to respond or are resistant to treatment with one or more conventional therapies for the particular tumor type. Refractory tumors include those that are hormone-refractory (e.g., androgen-independent prostate cancer; or hormone-refractory breast cancer, such as breast cancer that is refractory to tamoxifen); those that are refractory to treatment with one or more chemotherapeutic agents; those that are refractory to radiation; and those that are refractory to combinations of chemotherapy and radiation, chemotherapy and hormone therapy, or hormone therapy and radiation. By way of specific example, in some embodiments, the inventive methods, e.g., using ASN002, are directed to treating hematological cancer patients (e.g., leukemia and lymphoma patients) who are refractory to treatment with FDA-approved ibrutinib.

Representative types of cancers, cancer cells and tumors treatable in accordance with the methods of the present invention include carcinomas, sarcomas, benign and malignant tumors, and malignancies. Adult tumors/cancers and pediatric tumors/cancers are included. The cancers may be vascularized, or not yet substantially vascularized, or non-vascularized tumors. Thus, the cancers may be characterized by non-solid tumors, e.g., hematopoietic cancers such as leukemias and lymphomas (Hodgkins and non-Hodgkins) or solid tumors.

Representative examples of cancers characterized by solid tumors which may be treated in accordance with the methods of the present invention include breast (including HER2+ and metastatic), colorectal, colon, renal, rectal, pancreatic, prostate, stomach, gastrointestinal, gastric, stomach, esophageal, bile duct, lung (including small cell and non-small cell lung tumors, adenocarcinoma of the lung and squamous carcinoma of the lung), liver, lymphoma, epidermoid tumors, squamous tumors such as head and neck tumors, epithelial squamous cell cancer, thyroid, cervical, ovarian, neuroendocrine tumors of the digestive system, neuroendocrine tumors, pheochromacytomas, cancer of the peritoneum, hepatocellular cancer, hepatoblastoma, HPCR, glioblastoma, bladder cancer, hepatoma, endometrial or uterine carcinoma, salivary gland carcinoma, kidney or renal cancer, bone cancer, soft tissue sarcoma (including embryonal and alveolar rhabdomyosarcoma, GIST, alveolar soft part sarcoma and clear cell sarcoma), cholangiocarcinoma, bile cancer, gallbladder carcinoma, myeloma, vulval cancer, hepatic carcinoma, anal carcinoma, penile carcinoma, retinal, androgen-dependent tumors, androgen-independent tumors, Kaposi's sarcoma, synovial sarcoma, vasoactive intestinal peptide secreting tumor, CNS neoplasms, neuroblastomas, capillary hemangioblastomas, meningiomas, and cerebral metastases, melanoma, rhabdomyosarcoma, glioblastoma, including glioblastoma multiforme, EMB, RMS, ALV, medulloblastoma, ependymoma, Wilm's cancer, Ewing's cancer, osteosarcoma, PNT, rhabdoid, rhabdomyosarcoma, retinoblastoma, adrenal cortical cancer, adrenal cancer, and leiomyosarcoma.

Representative examples of hematologic malignancies amenable to treatment in accordance with the present invention include lymphomas, multiple myelomas, and leukemias.

In some embodiments, the hematologic malignancy is leukemia or lymphoma. Leukemias treatable in accordance with the present invention include lymphocytic leukemias and chronic myeloid (myelogenous) leukemias. Specific examples include acute lymphocytic leukemia (ALL), acute myeloid leukemia (AML) (e.g., HEL), chronic lymphocytic leukemia (CLL), and chronic myelogenous leukemia (CML). Other examples include T-cell acute lymphoblastic leukemia (T-ALL) and B-cell acute lymphoblastic leukemia (B-ALL).

In some embodiments, the hematologic malignancy is lymphoma (e.g., malignant neoplasms of lymphoid and reticuloendothelial tissues). Examples of lymphomas treatable in accordance with the present invention include Burkitt's lymphoma, Hodgkins' lymphoma, non-Hodgkins' lymphomas, lymphocytic lymphomas such as small lymphocytic lymphoma (SLL), myelodysplastic syndrome (MDS), myeloproliferative disease (MPD), indolent non-Hodgkin's lymphoma (iNHL), refractory iNHL, mantle cell lymphoma (MCL), follicular lymphoma (FL), Waldestrom's macroglobulinemia (WM), T-cell lymphoma, B-cell lymphoma, diffuse large B-cell lymphoma (DLBCL), lymphoplasmacytic lymphoma (LPL), and marginal zone lymphoma (MZL).

The compound of formula (I) may be administered alone (monotherapy), in the form of a conjugate (e.g., chemically bonded to another moiety that targets cancer cells) or in combination with one or more therapeutically effective active agents (e.g., anti-cancer agents) or treatments (combination therapy). The other therapeutically effective agent, which is different from the compound of formula (I), may be incorporated into the same composition as the compound of formula (I), or may be administered as a separate composition. The other therapeutically effective agent or treatment may be administered prior to, during and/or after the administration of the compound of formula (I). The other therapeutically effective agent may be administered to augment the therapeutic effect of the compound of formula (I), or to diminish the negative side effects of the compound of formula (I).

Other anti-cancer therapeutically effective agents/treatments include surgery, radiation chemotherapeutic agents, cytokines, chemokines and biological agents such as antibodies and enzymes.

When the anti-neoplastic agent is radiation, the source of the radiation can be either external (external beam radiation therapy—EBRT) or internal (brachytherapy—BT) to the patient being treated. The dose of anti-neoplastic agent administered depends on numerous factors, including, for example, the type of agent, the type and severity of tumor being treated and the route of administration of the agent. It should be emphasized, however, that the present invention is not limited to any particular dose. Radiation may also be used in conjunction with other antineoplastic agents.

Examples of chemotherapeutic agents (which are typically small molecules) include topoisomerase inhibitors (e.g., inhibitors of topoisomerase I or topoisomerase II. Topoisomerase I inhibitors such as irinotecan (CPT-II), aminocamptothecin, camptothecin, DX-8951f, and topotecan. Topoisomerase II inhibitors include etoposide (VP-16), and teniposide (VM-26)), cyclophosphamide, Thiotepa, bysulfan, melphalan, dacarbazine, cytosine arabinoside, cyclophosphamide, actinomycin-D, methotrexate, gemcitabine, oxyplatin, fluorouracil (5-FU), leucourin (LU), cisplatin, irinotecan (CPT-II), paclitaxel, docetaxel, vinblastine, epothilone, carboplatin, pegylated adriamycin, anthracyclines (e.g., daunomycin and doxorubicin), vindesine, neocarzinostatin, cis-platinum, chlorambucil, cytosine arabinoside, 5-fluorouridine, ibrutinib, and calicheamicin.

The present invention may now be described in accordance with the following, non-limiting working examples.

WORKING EXAMPLES

Example 1

ASN002 Exhibits Anti-Tumor Activity in Ibrutinib-Resistant Lymphoma Cells

This activity of ASN002 was assessed using a diffuse large B-cell lymphoma (DLBCL) cell line, Pfeiffer ("Parental"); and an ibrutinib-resistant variant of the same cell line ("Ibrutinib-R"), which was developed by growing the cells in the presence of increasing concentrations of ibrutinib. Pools of ibrutinib-resistant cells were tested in this study. The drug idelalisib (which was approved by the FDA in July 2015 for the treatment of B-cell blood cancers) was used for comparison as a reference compound. The data are set forth in Table A ($IC_{50}$ is the half maximal inhibitory concentration). They show that ASN002 was significantly more potent in inhibiting tumor cell proliferation than either ibrutinib or idelalisib, in the Pfeiffer cell line and, in particular, the ibrutinib-resistant cell line.

TABLE A

| | Cell Proliferation $IC_{50}$ (μM) | |
|---|---|---|
| Compound | Parental | Ibrutinib-R |
| ASN002 | 0.08 | 0.32 |
| Ibrutinib | 0.27 | 4.5 |
| Idelalisib | 0.13 | >10 |

Example 2

The anti-cancer activity of ASN002 was also evaluated in many solid tumor cell lines. $IC_{50}$ values for the antiproliferative activity of ASN002 in these cell lines are set forth in TABLE B.

TABLE B

| Cell Line | Tumor Type | $IC_{50}$ (uM) |
|---|---|---|
| HT1376 | Bladder | 0.09 |
| LoVo | Colon | 0.15 |
| HepG2 | Liver | 0.24 |
| HT29 | Colon | 0.30 |
| Caki1 | Kidney | 0.33 |
| TCCSUP | Bladder | 0.34 |
| H1581 | Lung | 0.38 |
| MFM-223 | Breast | 0.40 |
| CAOV3 | Ovary | 0.42 |
| 5637 | Bladder | 0.42 |
| ZR75 | Breast | 0.42 |
| HCT116 | Colon | 0.43 |
| T24 | Bladder | 0.44 |
| SCaBER | Bladder | 0.45 |
| A549 | Lung | 0.46 |
| MDAMB361 | Breast | 0.49 |
| C33A | Cervical | 0.50 |
| HT1197 | Bladder | 0.54 |
| SW480 | Colon | 0.60 |
| MCF7 | Breast | 0.60 |
| Colo205 | Colon | 0.61 |
| A375 | Melanoma | 0.61 |
| Hec1A | Endometrial | 0.66 |
| BxPC3 | Pancreas | 0.66 |
| SKOV3 | Ovarian | 0.73 |
| HeLa | Cervical | 0.77 |
| MDA-MB-231 | Breast | 0.77 |
| HUG1N | Gasrtic | 0.81 |
| AsPC1 | Pancreas | 0.84 |
| H1975 | Lung | 0.85 |
| CFPac1 | Pancreas | 0.85 |
| KE39 | Gastric | 0.86 |
| MKN1 | Gastric | 0.88 |
| MFE296 | Endometrial | 0.88 |
| H460 | Lung | 0.91 |
| DU145 | Prostate | 0.99 |
| SKMEL2 | Melanoma | 1.03 |
| LNCaP | Prostate | 1.07 |
| MDAMB468 | Breast | 1.46 |
| SW1990 | Pancreas | 1.62 |
| HCC1806 | Breast | 1.63 |
| MDAMB453 | Breast | 1.74 |
| EAhy296 | Endothelial | 1.80 |
| PC3 | Prostate | 1.98 |
| BT20 | Breast | 2.13 |
| UMUC3 | Bladder | 2.28 |
| J82 | Bladder | 2.75 |

TABLE B-continued

| Cell Line | Tumor Type | IC$_{50}$ (uM) |
|---|---|---|
| MIAPACA2 | Pancreas | 2.77 |
| BT474 | Breast | >10 |
| H1299 | Lung | >10 |
| HCC1937 | Breast | >10 |
| HCC1954 | Breast | >10 |
| JEG3 | Placenta | >10 |
| SKHEP1 | Endothelial | >10 |
| SKMEL28 | Melanoma | >10 |
| SW780 | Bladder | >10 |
| U87MG | Glioblastoma | >10 |
| Y79 | Retiblastoma | >10 |

All patent publications and non-patent publications are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of treating a cancer subject, comprising administering to a cancer subject in need thereof, a therapeutically effective amount of a compound 2-(1-(4-((4-(4-hydroxypiperidin-1-yl)phenyl)amino)-5-oxo-5,6-dihydropyrimido[4,5-d]pyridazin-2-yl)piperidin-4-yl)acetonitrile, or a pharmaceutically acceptable salt or ester thereof, wherein:
the cancer subject has a recurrent or refractory cancer;
the cancer is a hematopoietic cancer; and
the cancer is refractory to Ibrutinib.

2. The method of claim 1, wherein the compound is a salt of an acid and the acid is selected from the group consisting of acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, trifluoroacetic, and camphorsulfonic.

3. The method of claim 1, wherein the hematopoietic cancer is lymphoma.

4. The method of claim 3, wherein the lymphoma is diffuse large B-cell lymphoma.

5. The method of claim 3, wherein the lymphoma is mantle cell lymphoma.

6. The method of claim 3, wherein the lymphoma is follicular lymphoma.

7. The method of claim 1, wherein the hematopoietic cancer is leukemia.

8. The method of claim 7, wherein the leukemia is acute myeloid leukemia (AML).

9. The method of claim 8, wherein the AML is human erythroleukemia.

10. The method of claim 1, wherein the hematopoietic cancer is multiple myeloma.

11. The method of claim 1, wherein the cancer subject is a mammal.

12. The method of claim 11, wherein the mammal is human.

13. The method of claim 1, wherein the compound is administered orally.

14. The method of claim 1, wherein the compound is administered parenterally.

15. The method of claim 14, wherein the compound is administered via injection.

16. The method of claim 1, wherein the compound is formulated in a dosage form further comprising a pharmaceutically acceptable carrier.

17. The method of claim 1, wherein the cancer subject has undergone a prior anti-cancer treatment regimen.

* * * * *